United States Patent
Wang et al.

(10) Patent No.: US 12,195,554 B2
(45) Date of Patent: Jan. 14, 2025

(54) ANTI-POLYSIALIC ACID ANTIBODIES AND USES THEREOF

(71) Applicant: MEMORIAL SLOAN KETTERING CANCER CENTER, New York, NY (US)

(72) Inventors: Linlin Wang, New York, NY (US); Zhihao Wu, New York, NY (US); Mahiuddin Ahmed, New York, NY (US); Sarah M. Taldone, New York, NY (US); Steven M. Larson, New York, NY (US); Nai-Kong V. Cheung, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1009 days.

(21) Appl. No.: 16/980,354

(22) PCT Filed: Mar. 13, 2019

(86) PCT No.: PCT/US2019/022037
§ 371 (c)(1),
(2) Date: Sep. 11, 2020

(87) PCT Pub. No.: WO2019/178218
PCT Pub. Date: Sep. 19, 2019

(65) Prior Publication Data
US 2021/0047436 A1    Feb. 18, 2021

Related U.S. Application Data

(60) Provisional application No. 62/643,141, filed on Mar. 14, 2018.

(51) Int. Cl.
| | | |
|---|---|---|
| *C07K 16/44* | (2006.01) | |
| *A61K 45/06* | (2006.01) | |
| *A61K 47/68* | (2017.01) | |
| *A61P 35/00* | (2006.01) | |

(52) U.S. Cl.
CPC .......... *C07K 16/44* (2013.01); *A61K 47/6835* (2017.08); *A61P 35/00* (2018.01); *A61K 45/06* (2013.01)

(58) Field of Classification Search
CPC .................. C07K 16/44; C07K 2317/24; C07K 2317/31; A61K 47/6835; A61K 45/06; A61K 2039/505; A61K 51/0482; A61P 35/00
See application file for complete search history.

(56) References Cited

U.S. PATENT DOCUMENTS

| | | |
|---|---|---|
| 2005/0118183 A1 | 6/2005 | Hoffee et al. |
| 2010/0036091 A1 | 2/2010 | Robinson et al. |
| 2017/0029526 A1 | 2/2017 | Yu et al. |
| 2017/0360953 A1 | 12/2017 | Grawunder et al. |

FOREIGN PATENT DOCUMENTS

| | | | | |
|---|---|---|---|---|
| CN | 107759700 A | 3/2018 | | |
| WO | WO-2004020579 A2 | * 3/2004 | ............. | C07K 16/00 |
| WO | WO-2016187220 A2 | * 11/2016 | ............. | A61K 38/05 |
| WO | WO-2017/178653 A1 | 10/2017 | | |

OTHER PUBLICATIONS

Kussie et al., A Single Engineered Amino Acid Substitution Changes Antibody Fine Specificity, 1994, Journal of Immunology, pp. 146-152 (Year: 1994).*
Rudikoff et al., Single amino acid substitution altering antigen-binding specificity, 1982, PNAS, vol. 79, pp. 1979-1983 (Year: 1982).*
Vajdos et al., Comprehensive Functional Maps of the Antigen-binding Site of an Anti-ErbB2 Antibody Obtained with Shotgun Scanning Mutagenesis, 2002, Journal of Molecular Biology, vol. 320, pp. 415-428 (Year: 2002).*
Brown et al., Tolerance to Single, but Not Multiple, Amino Acid Replacements in Antibody VH CDR2, 1996, Journal of Immunology, vol. 156, pp. 3285-3291 (Year: 1996).*
Nagae et al., Crystal Structure of Anti-polysialic Acid Antibody Single Chain Fv Fragment Complexed with Octasialic Acid, 2013, The Journal of Biological Chemistry, vol. 288, No. 47, pp. 33784-33796; instant PTO-892 (Year: 2013).*
Biologics International Corp, Chimeric Antibody, 2019, retrieved from: https://www.biologicscorp.com/chimeric-antibody/ (Year: 2019).*
Orcutt et al., Biodistribution and Clearance of Small Molecule Hapten Chelates for Pretargeted Radioimmunotherapy, 2011, Molecule Imaging Biology, vol. 13, Issue 2, pp. 1-16 (Year: 2011).*
Wang et al., IgG Fc Engineering to Modulate Antibody Effector Functions, 2018, Protein Cell, vol. 9, Issue 1, pp. 63-73 (Year: 2018).*
Tanaka et al., Prognostic Significance of Polysialic Acid Expression in Resected Non-Small Cell Lung Cancer, 2001, Cancer Research, vol. 61, pp. 1666-1670 (Year: 2001).*
Cosaert et al., Platinum drugs in the treatment of non-small-cell lung cancer, 2002, British Journal of Cancer, vol. 87, pp. 825-833 (Year: 2002).*
International Search Report on PCT/US2019/022037 DTD Jul. 19, 2019, 6 pages.
Karen J. Colley et al: "Polysialic acid: Biosynthesis, novel functions and applications", Critical Reviews in Biochemistry and Molecular Biology, vol. 49, No. 6, Nov. 1, 2014 (Nov. 1, 2014), pp. 498-532.

(Continued)

*Primary Examiner* — Jeffrey Stucker
*Assistant Examiner* — Brittney E Donoghue
(74) *Attorney, Agent, or Firm* — Foley & Lardner LLP

(57) ABSTRACT

The present disclosure relates generally to immunoglobulin-related compositions (e.g., antibodies or antigen binding fragments thereof) that can bind to and neutralize the activity of polysialic acid. The antibodies of the present technology are useful in methods for detecting and treating a polysialic acid-associated cancer in a subject in need thereof.

20 Claims, 79 Drawing Sheets
Specification includes a Sequence Listing.

(56) References Cited

OTHER PUBLICATIONS

Lindsay M. Steirer et al: "An Antibody to De-N-Acetyl Sialic Acid Containing-Polysialic Acid Identifies an Intracellular Antigen and Induces Apoptosis in Human Cancer Cell Lines", PLOS One, vol. 6, No. 11, Nov. 9, 2011 (Nov. 9, 2011), p. e27249.

Watzlawik Jens O et al: "A human anti-polysialic acid antibody as a potential treatment to improve function in multiple sclerosis patients.", Journal of Nature and Science Aug. 2015, [Online] vol. 1, No. 8, Aug. 1, 2015 (Aug. 1, 2015).

\* cited by examiner

Figure 1(A)

| Tumor Type | Cell Line | RSV | polySia |
|---|---|---|---|
| neuroblastoma | IMR32 | 5 | 3993 |
| neuroblastoma | BE(1)N | 5 | 2550 |
| neuroblastoma | NGP | 5 | 1585 |
| small cell lung cancer | HTB-180 NCI-H345 | 5 | 1116 |
| neuroblastoma | BE(2)C | 5 | 1067 |
| neuroblastoma | BE(2)N | 6 | 1035 |
| small cell lung cancer | NCI H847 | 5 | 996 |
| neuroblastoma | LS | 5 | 958 |
| neuroblastoma | LAN-5 | 5 | 879 |
| small cell lung cancer | NCI-N417 | 5 | 822 |
| acute myeloid leukemia | M-07E | 5 | 781 |
| neuroblastoma | BE(2)M17 | 5 | 770 |
| neuroblastoma | BE(2)S | 6 | 651 |
| acute myeloid leukemia | MOLM-13 | 5 | 644 |
| neuroblastoma | 66N | 5 | 609 |
| neuroblastoma | NB1691 | 5 | 449 |
| melanoma | M14 LUC | 5 | 429 |
| small cell lung cancer | NCI-H524 | 5 | 408 |
| small cell lung cancer | DMS 79 | 5 | 387 |
| neuroblastoma | NB5 | 5 | 348 |
| neuroblastoma | LAN-6 | 5 | 339 |
| chondrosarcoma | CH2879 | 5 | 314 |
| neuroblastoma | 6S | 5 | 292 |
| neuroblastoma | LAN-1 | 5 | 289 |
| acute myeloid leukemia | EOL-1 | 6 | 275 |
| small cell lung cancer | NCI-H2106 | 5 | 262 |
| small cell lung cancer | NCI N417 | 5 | 244 |
| leukemia, biphenotypic B myelomonocytic | MV-4-11 | 5 | 228 |
| small cell lung cancer | NCI-H128 | 6 | 221 |
| small cell lung cancer | NCI-H847 | 5 | 151 |
| breast cancer | JIMT-1 | 5 | 132 |
| osteosarcoma | CRL-1427 LUC GFP | 5 | 130 |
| osteosarcoma | 143B | 5 | 129 |
| mesothelioma | MESC 10 | 6 | 89 |
| small cell lung cancer | NCI H524 | 5 | 68 |
| neuroblastoma | KCN-R LUC | 5 | 63 |
| small cell lung cancer | DMS 454 | 5 | 52 |
| malignant melanoma | CRL-1424 G-361 | 5 | 46 |
| malignant melanoma | G-361 | 5 | 42 |
| T cell leukemia | CML-T1 | 5 | 40 |
| small cell lung cancer | NCI-H146 | 5 | 38 |
| small cell lung cancer | NCI-H526 | 5 | 34 |
| non-small cell lung cancer | LX22 CLWT | 5 | 33 |

Figure 1(B)

| Tumor Type | Cell Line | RSV | polySia |
|---|---|---|---|
| pancreas | CRL-2172 SW 1990 | 5 | 33 |
| (EBV)-transformed B-lymphoblastoid cell line | IM-9 | 10 | 30 |
| (EBV)-transformed B-lymphoblastoid cell line | COG-V-486 BLCL | 6 | 30 |
| chronic myeloid leukemia | K562 A2 | 5 | 26 |
| acute lymphocytic leukemia | MOLT-4 | 5 | 24 |
| nasopharyngeal carcinoma | C 666-1 | 5 | 24 |
| small cell lung cancer | NCI H1963 | 5 | 20 |

Figure 2

| # | SCLC PDX | polySia staining (IHC) |
|---|---|---|
| 1 | LX110 | 2-3 |
| 2 | LX102 | 2 |
| 3 | LX33B | 3 |
| 4 | Lu148 | 3-4 |
| 5 | LX44 | 3 |
| 6 | LX92 | 3 |
| 7 | LX48 | 2 |
| 8 | Lu73 | 2-3 |
| 9 | Lu149 | 2-3 |
| 10 | LX101 | 3-4 |
| 11 | LX47 | 3-4 |
| 12 | LX108 | 3-4 |
| 13 | LX22 | 0 |
| 14 | LX88 | 3 |

Figure 8(A)

| Sample | $k_a$ (1/Ms) | $k_d$ (1/s) | $K_D$ (M) |
|---|---|---|---|
| DS54 | 2.43E+06 | 2.29E-03 | 9.42E-10 |
| DS45 | 1.35E+06 | 1.49E-03 | 1.10E-09 |
| DS47 | 4.82E+05 | 5.98E-04 | 1.24E-09 |
| P35 H1L2 D31R | 2.11E+08 | 5.05E-01 | 2.39E-09 |
| DS55 | 6.09E+05 | 1.55E-03 | 2.55E-09 |
| DS53 | 3.44E+05 | 9.47E-04 | 2.75E-09 |
| P35 H1L2 (parental) | 8.65E+05 | 3.91E-03 | 4.52E-09 |
| DS51 | 4.09E+05 | 2.15E-03 | 5.26E-09 |

Figure 8(B)

| Clones (Direct Screen) | HC | | | | | | | | | | LC | | | | | | | | |
|---|---|---|---|---|---|---|---|---|---|---|---|---|---|---|---|---|---|---|---|
| | 12 | 19 | 28 | 31 | 36 | 38 | 50 | 63 | 92 | 115 | 9 | 24 | 53 | 54 | 64 | 65 | 75 | 99 | 105 |
| | V | K | T | D | W | K | W | K | A | V | L | R | I | Y | P | D | D | V | Q |
| DS45 | | | | G | | | S | | | | | | | | | | | | |
| DS47 | | | | N | | M | R | | | | | | | | | | | | |
| DS51 | | | | G | | | C | | | | | | | | | | | | |
| DS53 | | | | | | M | R | | | | | | | | | | | | |
| DS54 | | | | N | | | R | | | | | | | | | | | | |
| DS55 | | | | N | | | C | | | | | | | | | | | | |
| D31R | | | | R | | | | | | | | | | | | | | | |

Figure 9(A)

| Sample | $k_a$ (1/Ms) | $k_d$ (1/s) | $K_D$ (M) |
|---|---|---|---|
| KS34 | 1.56E+06 | 2.42E-03 | 1.55E-09 |
| P35 H1L2 D31R | 2.11E+08 | 5.05E-01 | 2.39E-09 |
| KS10 | 2.53E+05 | 7.26E-04 | 2.87E-09 |
| KS2 | 2.08E+05 | 6.27E-04 | 3.02E-09 |
| KS21 | 2.89E+05 | 8.74E-04 | 3.03E-09 |
| KS26 | 2.25E+05 | 7.93E-04 | 3.52E-09 |
| KS30 | 4.53E+05 | 1.71E-03 | 3.77E-09 |
| KS23 | 1.90E+05 | 7.96E-04 | 4.18E-09 |
| P35 H1L2 (parental) | 8.65E+05 | 3.91E-03 | 4.52E-09 |

Figure 9(B)

| Clones (Kinetic Screen) | HC | | | | | | | LC | | | | | | | | | | | | |
|---|---|---|---|---|---|---|---|---|---|---|---|---|---|---|---|---|---|---|---|---|
| | 26 | 36 | 50 | 65 | 76 | 80 | 91 | 19 | 29 | 34 | 35 | 47 | 62 | 65 | 67 | 81 | 85 | 86 | 90 | 99 | 102 |
| | G | W | W | K | A | Y | T | A | L | G | N | Q | G | D | F | S | A | E | V | V | T |
| KS2 | | | | E | | H | | | | | | | | C | | T | | | | | T |
| KS10 | | | C | | | | | | | | | | | C | | | | | | | |
| KS21 | | C | | | | | | | | | K | | | C | | | | | | | |
| KS23 | A | | | | | | | | | | | | | C | | | | | | | |
| KS26 | | | | | | | | | | | K | | | | | | | K | | | |
| KS30 | | | | | | | | | | V | | | | C | | | | | | E | |
| KS34 | | | | | V | N | | | | | | | | C | Y | | | | | | |

| EC50 (ug/ml) | M14 LUC | IMR-32 | SKNSH |
|---|---|---|---|
| BC137 KS2 | 0.58 | | |
| BC137 KS34 | 0.18 | | |
| BC137 DS47 | 0.02 | 0.07 | 0.04 |
| BC137 DS54 | 0.05 | 0.06 | 0.08 |
| BC137 DS47 D31R | 0.06 | 0.05 | 0.09 |
| BC137 DS54 D31R | 0.12 | | |
| WT | 0.45 | 0.26 | ~0.4 |

Figure 14(A)

| Clone | % human germline content in VH |
|---|---|
| m735 VH | 69.4 |
| P35 H1 | 75.5 |
| P35 H2 | 80.6 |
| HP35 H1 | 86.7 |
| HP35 H2 | 87.8 |
| HP35 H3 | 86.7 |
| HP35 H4 | 87.8 |
| HP35 H5 | 86.7 |
| HP35 H6 | 86.7 |
| HP35 H7 | 86.7 |
| HP35 H8 | 86.7 |

Figure 14(B)

| Clone | % human germline content in VL |
|---|---|
| m735 VL | 83.0 |
| P35 L1 | 86.0 |
| P35 L2 | 88.0 |
| HP35 L1 | 92.0 |
| HP35 L2 | 92.0 |
| HP35 L3 | 92.0 |

Figure 15(A)

Chimeric P35

*Heavy chain* (SEQ ID NO: 23)

QIQLQQSGPELVRPGASVKISCKASGYTFT<u>DYYIH</u>WVKQRPGEGLEWIG<u>WIYPGSGNTKYN
EKFKG</u>KATLTVDTSSSTAYMQLSSLTSEDSAVYFCAR<u>GGKFAMDY</u>WGQGTSVTVSSASTK
GPSVFPLAPSSKSTSGGTAALGCLVKDYFPEPVTVSWNSGALTSGVHTFPAVLQSSGLYSLS
SVVTVPSSSLGTQTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCS
VMHEALHNHYTQKSLSLSPGK

Figure 15(B)

Chimeric P35

*Light chain* (SEQ ID NO: 24)

DVVMTQTPLSLPVSLGDQASISC<u>RSSQSLVHSNGNTYLY</u>WYLQKPGQSPKPLIYR<u>VSNRFS</u>
GVPDRFSGSGSGTDFTLKISRVEAEDLGVYFC<u>FQGTHVPYT</u>FGGGTRLEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

Figure 16(A)

Humanized P35 H1 heavy chain

*Amino acid:* (SEQ ID NO: 25)
QIQLQQSGPEVVKPGASVKISCKASGYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

*Nucleotide:* (SEQ ID NO: 92)
CAGATCCAGCTGCAGCAGTCTGGACCCGAGGTCGTGAAGCCTGGCGCCTCCGTGAAGA
TCTCCTGCAAGGCCTCCGGCTACACCTTCACCGACTACTACATCCACTGGGTCAAGCAG
CGGCCAGGCCAGGGCCTGGAATGGATCGGCTGGATCTATCCCGGCTCCGGCAACACCA
AGTACAACGAGAAGTTCAAGGGCAAGGCCACCCTGACCGTGGACACCTCTGCCTCCAC
CGCCTACATGGAACTGTCCTCCCTGACCTCCGAGGATACCGCCGTGTACTTCTGTGCCA
GAGGCGGCAAGTTCGCCATGGACTATTGGGGCCAGGGCACCCTCGTGACCGTGTCTAG
CGCTTCTACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCCGTCCTACAG
TCCTCAGGACTCTACTCCCTCAGCAGCGTGGTGACCGTGCCCTCCAGCAGCTTGGGCAC
CCAGACCTACATCTGCAACGTGAATCACAAGCCCAGCAACACCAAGGTGGACAAGAG
AGTTGAGCCCAAATCTTGTGACAAAACTCACACATGCCCACCGTGCCCAGCACCTGAA
CTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGC
GGGAGGAGCAGTACAACAGCACGTACCGTGTGGTCAGCGTCCTCACCGTCCTGCACCA
GGACTGGCTGAATGGCAAGGAGTACAAGTGCAAGGTCTCCAACAAAGCCCTCCCAGCC
CCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGG
TCAAAGGCTTCTATCCCAGCGACATCGCCGTGGAGTGGGAGAGCAATGGGCAGCCGGA
GAACAACTACAAGACCACGCCTCCCGTGCTGGACTCCGACGGCTCCTTCTTCCTCTACA
GCAAGCTCACCGTGGACAAGAGCAGGTGGCAGCAGGGGAACGTCTTCTCATGCTCCGT
GATGCATGAGGCTCTGCACAACCACTACACGCAGAAGAGCCTCTCCCTGTCTCCGGGT
AAATGA

Figure 16(B)

Humanized P35 H2 heavy chain

*Amino acid:* (SEQ ID NO: 26)
QIQLVQSGPEVVKPGASVKISCKASGYTFT<u>DYYIH</u>WVRQAPGQGLEWIG<u>WIYPGSGNTKY
NEKFKG</u>RATLTVDTSASTAYMELSSLRSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

*Nucleotide:* (SEQ ID NO: 93)
CAGATCCAGCTGGTGCAGTCTGGACCCGAGGTCGTGAAGCCTGGCGCCTCCGTGAAGA
TCTCCTGCAAGGCCTCCGGCTACACCTTCACCGACTACTACATCCACTGGGTGCGACAG
GCCCCTGGACAGGGCCTGGAATGGATCGGCTGGATCTACCCTGGCTCCGGCAACACCA
AGTACAACGAGAAGTTCAAGGGCAGAGCCACCCTGACCGTGGACACCTCTGCCTCCAC
CGCCTACATGGAACTGTCCTCCCTGCGGAGCGAGGATACCGCCGTGTACTTCTGTGCCA
GAGGCGGCAAGTTCGCCATGGACTATTGGGGCCAGGGCACCCTCGTGACCGTGTCTAG
CGCTTCTACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCCGTCCTACAG
TCCTCAGGACTCTACTCCCTCAGCAGCGTGGTGACCGTGCCCTCCAGCAGCTTGGGCAC
CCAGACCTACATCTGCAACGTGAATCACAAGCCCAGCAACACCAAGGTGGACAAGAG
AGTTGAGCCCAAATCTTGTGACAAAACTCACACATGCCCACCGTGCCCAGCACCTGAA
CTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGC
GGGAGGAGCAGTACAACAGCACGTACCGTGTGGTCAGCGTCCTCACCGTCCTGCACCA
GGACTGGCTGAATGGCAAGGAGTACAAGTGCAAGGTCTCCAACAAAGCCCTCCCAGCC
CCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGG
TCAAAGGCTTCTATCCCAGCGACATCGCCGTGGAGTGGGAGAGCAATGGGCAGCCGGA
GAACAACTACAAGACCACGCCTCCCGTGCTGGACTCCGACGGCTCCTTCTTCCTCTACA
GCAAGCTCACCGTGGACAAGAGCAGGTGGCAGCAGGGGAACGTCTTCTCATGCTCCGT
GATGCATGAGGCTCTGCACAACCACTACACGCAGAAGAGCCTCTCCCTGTCTCCGGGT
AAATGA

Figure 17(A)

Humanized P35 L1 light chain

*Amino acid:* (SEQ ID NO: 27)
DVVMTQSPLSLPVTLGDQASISCRSSQSLVHSNGNTYLYWYLQKPGQSPKPLIYRVSNRFS
GVPDRFSGSGSGTDFTLKISRVEAEDVGVYFCFQGTHVPYTFGGGTRLEIKRTVAAPSVFIF
PPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

*Nucleotide:* (SEQ ID NO: 94)
GACGTCGTGATGACACAGTCCCCTCTGTCCCTGCCTGTGACCCTGGGCGATCAGGCCTC
CATCTCCTGCAGATCCTCCCAGTCCCTGGTGCACTCCAACGGCAACACCTACCTGTACT
GGTATCTGCAGAAGCCCGGCCAGTCCCCCAAGCCCCTGATCTACAGAGTGTCCAACCG
GTTCTCCGGCGTGCCCGACAGATTCTCCGGCTCTGGCTCTGGCACCGACTTCACCCTGA
AGATCTCCCGGGTGGAAGCCGAGGACGTGGGCGTGTACTTCTGTTTTCAAGGCACCCA
CGTGCCCTACACCTTCGGCGGAGGCACCCGGCTGGAAATCAAGAGAACCGTGGCCGCT
CCCTCCGTGTTCATCTTCCCACCTTCCGACGAGCAGCTGAAGTCCGGCACCGCTTCTGT
CGTGTGCCTGCTGAACAACTTCTACCCCGCGAGGCCAAGGTGCAGTGGAAGGTGGAC
AACGCCCTGCAGTCCGGCAACTCCCAGGAATCCGTGACCGAGCAGGACTCCAAGGACA
GCACCTACTCCCTGTCCTCCACCCTGACCCTGTCCAAGGCCGACTACGAGAAGCACAA
GGTGTACGCCTGCGAAGTGACCCACCAGGGCCTGTCTAGCCCCGTGACCAAGTCTTTC
AACCGGGGCGAGTGCTAG

Figure 17(B)

Humanized P35 L2 light chain

*Amino acid:* (SEQ ID NO: 28)
DVVMTQSPLSLPVTLGQPASISC<u>RSSQSLVHSNGNTYLY</u>WYLQKPGQSPKPLIY<u>RVSNRFSG</u>
VPDRFSGSGSGTDFTLKISRVEAEDVGVYFC<u>FQGTHVPYT</u>FGQGTRLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

*Nucleotide:* (SEQ ID NO: 95)
GACGTCGTGATGACACAGTCCCCTCTGTCCCTGCCTGTGACCCTGGGACAGCCTGCCTC
CATCTCCTGCAGATCCTCCCAGTCCCTGGTGCACTCCAACGGCAACACCTACCTGTACT
GGTATCTGCAGAAGCCCGGCCAGTCCCCCAAGCCCCTGATCTACAGAGTGTCCAACCG
GTTCTCCGGCGTGCCCGACAGATTCTCCGGCTCTGGCTCTGGCACCGACTTCACCCTGA
AGATCTCCCGGGTGGAAGCCGAGGACGTGGGCGTGTACTTCTGTTTTCAAGGCACCCA
CGTGCCCTACACCTTCGGCCAGGGCACCCGGCTGGAAATCAAGAGAACCGTGGCCGCT
CCCTCCGTGTTCATCTTCCCACCTTCCGACGAGCAGCTGAAGTCCGGCACCGCTTCTGT
CGTGTGCCTGCTGAACAACTTCTACCCCGCGAGGCCAAGGTGCAGTGGAAGGTGGAC
AACGCCCTGCAGTCCGGCAACTCCCAGGAATCCGTGACCGAGCAGGACTCCAAGGACA
GCACCTACTCCCTGTCCTCCACCCTGACCCTGTCCAAGGCCGACTACGAGAAGCACAA
GGTGTACGCCTGCGAAGTGACCCACCAGGGCCTGTCTAGCCCCGTGACCAAGTCTTTC
AACCGGGGCGAGTGCTAG

Figure 18(A)

Humanized P35 H1L2 IgG1

*Heavy chain* (SEQ ID NO: 25)

QIQLQQSGPEVVKPGASVKISCKASGYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 18(B)

Humanized P35 H1L2 IgG1

*Light chain* (SEQ ID NO: 28)

DVVMTQSPLSLPVTLGQPASISC<u>RSSQSLVHSNGNTYLY</u>WYLQKPGQSPKPLIY<u>RVSNRF</u>SG
VPDRFSGSGSGTDFTLKISRVEAEDVGVYFC<u>FQGTHVPYT</u>FGQGTRLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Figure 19

Humanized P35 H1 heavy chain with D31R mutation (SEQ ID NO: 29)

QIQLQQSGPEVVKPGASVKISCKASGYTFT<u>RYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 20

Direct Screen clone 45 (DS45) VH (SEQ ID NO: 30)

QIQLQQSGPEVVKPGASVKISCKASGYTFT<u>GYYIH</u>WVKQRPGQGLEWIG<u>SIYPGSGNTKYN
EKFKG</u>KATLTVDTSASTAYMELSSLTSEDTAVYFCAR<u>GGKFAMDY</u>WGQGTLVTVSS

Figure 21

Direct Screen clone 47 (DS47) VH (SEQ ID NO: 31)

QIQLQQSGPEVVKPGASVKISCKASGYTFT<u>NYYIH</u>WVMQRPGQGLEWIG<u>RIYPGSGNTKY
NEKFKG</u>KATLTVDTSASTAYMELSSLTSEDTAVYFCAR<u>GGKFAMDY</u>WGQGTLVTVSS

Figure 22

Direct Screen clone 51 (DS51) VH (SEQ ID NO: 32)

QIQLQQSGPEVVKPGASVKISCKASGYTFT<u>GYYIH</u>WVKQRPGQGLEWIG<u>CIYPGSGNTKYN</u>
<u>EKFKG</u>KATLTVDTSASTAYMELSSLTSEDTAVYFCAR<u>GGKFAMDY</u>WGQGTLVTVSS

Figure 23

Direct Screen clone 53 (DS53) VH (SEQ ID NO: 33)

QIQLQQSGPEVVKPGASVKISCKASGYTFT<u>DYYIH</u>WVMQRPGQGLEWIG<u>RIYPGSGNTKY
NEKFKG</u>KATLTVDTSASTAYMELSSLTSEDTAVYFCAR<u>GGKFAMDY</u>WGQGTLVTVSS

Figure 24

Direct Screen clone 54 (DS54) VH (SEQ ID NO: 34)

QIQLQQSGPEVVKPGASVKISCKASGYTFT<u>NYYIH</u>WVKQRPGQGLEWIG<u>RIYPGSGNTKYN
EKFKG</u>KATLTVDTSASTAYMELSSLTSEDTAVYFCAR<u>GGKFAMDY</u>WGQGTLVTVSS

Figure 25

Direct Screen clone 55 (DS55) VH (SEQ ID NO: 35)

QIQLQQSGPEVVKPGASVKISCKASGYTFT<u>NYYIH</u>WVKQRPGQGLEWIG<u>CIYPGSGNTKYN
EKFKG</u>KATLTVDTSASTAYMELSSLTSEDTAVYFCAR<u>GGKFAMDY</u>WGQGTLVTVSS

Figure 26(A)

Kinetic Screen clone 2 (KS2) VH (SEQ ID NO: 36)

QIQLQQSGPEVVKPGASVKISCKASGYTFT<u>DYYIH</u>WVKQRPGQGLEWIG<u>WIYPGSGNTKYNEKFEG</u>KATLTVDTSASTAHMELSSLTSEDTAVYFCAR<u>GGKFAMDY</u>WGQGTLVTVSS

Figure 26(B)

Kinetic Screen clone 2 (KS2) VL (SEQ ID NO: 37)

DVVMTQSPLSLPVTLGQPASISC<u>RSSQSLVHSNGNTYLY</u>WYLQKPGQSPKPLIY<u>RVSNRFSG</u>VPCRFSGSGSGTDFTLKISRVETEDVGVYFC<u>FQGTHVPYI</u>FGQGTRLEIKR

Figure 27(A)

Kinetic Screen clone 10 (KS10) VH (SEQ ID NO: 38)

QIQLQQSGPEVVKPGASVKISCKASGYTFT<u>DYYIH</u>WVKQRPGQGLEWIG<u>CIYPGSGNTKYN
EKFKG</u>KATLTVDTSASTAYMELSSLTSEDTAVYFCAR<u>GGKFAMDY</u>WGQGTLVTVSS

Figure 27(B)

Kinetic Screen clone 10 (KS10) VL (SEQ ID NO: 39)

DVVMTQSPLSLPVTLGQPASISC<u>RSSQSLVHSNGNTYLY</u>WYLQKPGQSPKPLIY<u>RVSNRFS</u>C
VPDRFSGSGSGTDFTLKISRVEAEDVGVYFC<u>FQGTHVPYT</u>FGQGTRLEIKR

Figure 28(A)

Kinetic Screen clone 21 (KS21) VH (SEQ ID NO: 40)

QIQLQQSGPEVVKPGASVKISCKASGYTFT<u>DYYIH</u>CVKQRPGQGLEWIG<u>WIYPGSGNTKYN
EKFKG</u>KATLTVDTSASTAYMELSSLTSEDTAVYFCAR<u>GGKFAMDY</u>WGQGTLVTVSS

Figure 28(B)

Kinetic Screen clone 21 (KS21) VL (SEQ ID NO: 41)

DVVMTQSPLSLPVTLGQPASISC<u>RSSQSLVHSNGKTYLY</u>WYLQKPGQSPKPLIY<u>RVSNRFS</u>C
VPDRFSGSGSGTDFTLKISRVEAEDVGVYFC<u>FQGTHVPYT</u>FGQGTRLEIKR

Figure 29(A)

Kinetic Screen clone 23 (KS23) VH (SEQ ID NO: 42)

QIQLQQSGPEVVKPGASVKISCKASAYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSS

Figure 29(B)

Kinetic Screen clone 23 (KS23) VL (SEQ ID NO: 43)

DVVMTQSPLSLPVTLGQPASISC<u>RSSQSLVHSNGNTYLY</u>WYLQKPGQSPKPLIY<u>RVSNRFSG</u>
VPCRFSGSGSGTDFTLKISRVEAEDVGVYFC<u>FQGTHVPYT</u>FGQGTRLEIKR

Figure 30

Kinetic Screen clone 26 (KS26) VL (SEQ ID NO: 44)

DVVMTQSPLSLPVTLGQPASISC<u>RSSQSLVHSNGNTYLY</u>WYLQKPGKSPKPLIY<u>RVSNRFSG</u>
VPDRFSGSGSGTDFTLKISRVEAKDVGVYFC<u>FQGTHVPYT</u>FGQGTRLEIKR

Figure 31

Kinetic Screen clone 30 (KS30) VL (SEQ ID NO: 45)

DVVMTQSPLSLPVTLGQPVSISC<u>RSSQSLVHSNGNTYLY</u>WYLQKPGQSPKPLIY<u>RVSNRFSG</u>VPCRFSGSGSGTDFTLKISRVEAEDVGVYFC<u>FQGTHEPYT</u>FGQGTRLEIKR

Figure 32(A)

Kinetic Screen clone 34 (KS34) VH (SEQ ID NO: 46)

QIQLQQSGPEVVKPGASVKISCKASGYTFT<u>DYYIH</u>WVKQRPGQGLEWIG<u>WIYPGSGNTKYNEKFKG</u>KATLTVDTSVSTAYMELSSLTSEDNAVYFCAR<u>GGKFAMDY</u>WGQGTLVTVSS

Figure 32(B)

Kinetic Screen clone 34 (KS34) VL (SEQ ID NO: 47)

DVVMTQSPLSLPVTLGQPASISC<u>RSSQSLVHSNGNTYLY</u>WYLQKPGQSPKPLIY<u>RVSNRFSG</u>VPCRYSGSGSGTDFTLKISRVEAEDVGVYFC<u>FQGTHVPYT</u>FGQGTRLEIKR

Figure 33(A)

BC137 (polySia x CD3 BsAb) *Heavy chain*
*Amino acid:* (SEQ ID NO: 48)
QIQLQQSGPEVVKPGASVKISCKASGYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCAVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 33(B)

BC137 (polySia x CD3 BsAb) *Heavy chain*
*Nucleotide:* (SEQ ID NO: 96)
CAGATCCAGCTGCAGCAGTCTGGACCCGAGGTCGTGAAGCCTGGCGCCTCCGTGAAGA
TCTCCTGCAAGGCCTCCGGCTACACCTTCACCGACTACTACATCCACTGGGTCAAGCAG
CGGCCAGGCCAGGGCCTGGAATGGATCGGCTGGATCTATCCCGGCTCCGGCAACACCA
AGTACAACGAGAAGTTCAAGGGCAAGGCCACCCTGACCGTGGACACCTCTGCCTCCAC
CGCCTACATGGAACTGTCCTCCCTGACCTCCGAGGATACCGCCGTGTACTTCTGTGCCA
GAGGCGGCAAGTTCGCCATGGACTATTGGGGCCAGGGCACCCTCGTGACCGTGTCTAG
CGCTTCTACCAAGGGCCCCTCTGTGTTTCCTCTGGCCCCTCCAGCAAGTCCACCTCTG
GTGGAACAGCCGCCCTGGGCTGCCTCGTGAAGGACTACTTTCCCGAGCCCGTGACCGT
GTCCTGGAACTCTGGCGCTCTGACCTCTGGCGTGCACACCTTCCCTGCTGTGCTGCAGT
CTAGCGGCCTGTACTCCCTGTCCTCCGTCGTGACAGTGCCCTCCAGCTCTCTGGGCACC
CAGACCTACATCTGCAACGTGAACCACAAGCCCTCCAATACCAAGGTGGACAAGCGGG
TGGAACCCAAGTCCTGCGACAAGACCCACACCTGTCCCCCTTGTCCTGCCCCTGAACTG
CTGGGCGGACCTTCCGTGTTCCTGTTCCCCCCAAAGCCCAAGGACACCCTGATGATCTC
CCGGACCCCCGAAGTGACCTGCGTGGTGGTGGATGTGTCCCACGAGGACCCTGAAGTG
AAGTTCAATTGGTACGTGGACGGCGTGGAAGTGCACAACGCCAAGACCAAGCCTAGA
GAGGAACAGTACGCCTCCACCTACCGGGTGGTGTCCGTGCTGACAGTGCTGCACCAGG
ACTGGCTGAACGGCAAAGAGTACAAGTGCGCCGTGTCCAACAAGGCCCTGCCTGCCCC
CATCGAAAAGACCATCTCCAAGGCCAAGGGCCAGCCCCGGGAACCCCAGGTGTACAC
ACTGCCCCCTAGCAGGGACGAGCTGACCAAGAACCAGGTGTCCCTGACCTGTCTCGTG
AAAGGCTTCTACCCCTCCGATATCGCCGTGGAATGGGAGTCCAACGGCCAGCCTGAGA
ACAACTACAAGACCACCCCCCCTGTGCTGGACTCCGACGGCTCATTCTTCCTGTACAGC
AAGCTGACCGTGGACAAGTCCCGGTGGCAGCAGGGCAACGTGTTCTCCTGCTCCGTGA
TGCACGAGGCCCTGCACAACCACTACACCCAGAAGTCCCTGTCCCTGAGCCCCGGCAA
ATGA

Figure 33(C)

BC137 (polySia x CD3 BsAb) *Light chain* - humanized P35 L2 – linker – huOKT3scFv
*Amino acid:* (SEQ ID NO: 49)
DVVMTQSPLSLPVTLGQPASISC<u>RSSQSLVHSNGNTYLY</u>WYLQKPGQSPKPLIY<u>RVSNRFSG</u>
VPDRFSGSGSGTDFTLKISRVEAEDVGVYFC<u>FQGTHVPYT</u>FGQGTRLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGECTS<u>GGGGSGGGGSGGGGS</u>QVQLVQSG
GGVVQPGRSLRLSCKASGYTFTRYTMHWVRQAPGKCLEWIGYINPSRGYTNYNQKFKDR
FTISRDNSKNTAFLQMDSLRPEDTGVYFCARYYDDHYSLDYWGQGTPVTVSS<u>GGGGSGGG
GSGGGGSGGGGSGGGGSGGGGS</u>DIQMTQSPSSLSASVGDRVTITCSASSSVSYMNWYQQT
PGKAPKRWIYDTSKLASGVPSRFSGSGSGTDYTFTISSLQPEDIATYYCQQWSSNPFTFGCG
TKLQITR

Figure 33(D)

BC137 (polySia x CD3 BsAb) *Light chain* - humanized P35 L2 – linker – huOKT3scFv
*Nucleotide:* (SEQ ID NO: 97)
GACGTCGTGATGACACAGTCCCCTCTGTCCCTGCCTGTGACCCTGGGACAGCCTGCCTC
CATCTCCTGCAGATCCTCCCAGTCCCTGGTGCACTCCAACGGCAACACCTACCTGTACT
GGTATCTGCAGAAGCCCGGCCAGTCCCCCAAGCCCCTGATCTACAGAGTGTCCAACCG
GTTCTCCGGCGTGCCCGACAGATTCTCCGGCTCTGGCTCTGGCACCGACTTCACCCTGA
AGATCTCCCGGGTGGAAGCCGAGGACGTGGGCGTGTACTTCTGTTTTCAAGGCACCCA
CGTGCCCTACACCTTCGGCCAGGGCACCCGGCTGGAAATCAAGAGAACCGTGGCCGCT
CCCTCCGTGTTCATCTTCCCACCTTCCGACGAGCAGCTGAAGTCCGGCACCGCTTCTGT
CGTGTGCCTGCTGAACAACTTCTACCCCGCGAGGCCAAGGTGCAGTGGAAGGTGGAC
AACGCCCTGCAGTCCGGCAACTCCCAGGAATCCGTGACCGAGCAGGACTCCAAGGACA
GCACCTACTCCCTGTCCTCCACCCTGACCCTGTCCAAGGCCGACTACGAGAAGCACAA
GGTGTACGCCTGCGAAGTGACCCACCAGGGCCTGTCTAGCCCCGTGACCAAGTCTTTC
AACCGGGGCGAGTGCACTAGTGGCGGCGGAGGATCTGGCGGAGGTGGAAGCGGAGGG
GGAGGATCTCAGGTGCAGCTGGTGCAGAGCGGAGGCGGAGTGGTGCAGCCTGGCAGA
TCCCTGAGACTGTCCTGCAAGGCCTCCGGCTACACCTTCACCCGGTACACCATGCACTG
GGTGCGACAGGCCCCTGGCAAGTGCCTGGAATGGATCGGCTACATCAACCCCTCCCGG
GGCTACACCAACTACAACCAGAAGTTCAAGGACCGGTTCACCATCTCCCGGGACAACT
CCAAGAACACCGCCTTTCTGCAGATGGACTCCCTGCGGCCTGAGGATACCGGCGTGTA
CTTCTGCGCCCGGTACTACGACGACCACTACTCCCTGGACTACTGGGGCCAGGGAACC
CCTGTGACAGTGTCATCTGGTGGCGGAGGAAGTGGGGGAGGCGGATCAGGTGGTGGTG
GATCAGGCGGGGGAGGTTCAGGGGGTGGCGGTTCTGGGGGAGGGGGCTCTGATATTCA
GATGACTCAGAGCCCTTCCAGCCTGAGCGCCTCCGTGGGAGATCGCGTGACAATTACC
TGCTCTGCCTCCTCCTCCGTGTCTTACATGAATTGGTATCAGCAGACCCCTGGGAAGGC
TCCTAAGCGGTGGATCTACGACACCTCCAAGCTGGCCTCTGGCGTGCCCAGCAGGTTTT
CTGGCTCCGGCAGCGGCACAGATTATACCTTCACCATCAGCTCCCTGCAGCCAGAAGA
TATCGCTACCTATTATTGTCAGCAGTGGTCCTCCAACCCTTTCACCTTCGGCTGCGGCA
CAAAGCTGCAGATCACAAGATAG

Figure 34(A)

BC137-2 *Light chain*
*Amino acid:* (SEQ ID NO: 50)
DVVMTQSPLSLPVTLGQPASISC<u>RSSQSLVHSNGNTYLY</u>WYLQKPGQSPKPLIYR<u>VSNRFSG</u>
VPDRFSGSGSGTDFTLKISRVEAEDVGVYFC<u>FQGTHVPYT</u>FGQGTRLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGECTS<u>GGGGSGGGGSGGGGS</u>QVQLVQSG
GGVVQPGRSLRLSCKASGYTFTRYTMHWVRQAPGK<u>G</u>LEWIGYINPSRGYTNYNQKFKDR
FTISRDNSKNTAFLQMDSLRPEDTGVYFCARYYDDHYSLDYWGQGTPVTVSS<u>GGGGSGGG
GSGGGGSGGGGSGGGGSGGGGS</u>DIQMTQSPSSLSASVGDRVTITCSASSSVSYMNWYQQT
PGKAPKRWIYDTSKLASGVPSRFSGSGSGTDYTFTISSLQPEDIATYYCQQWSSNPFTFGQG
TKLQITR

Figure 34(B)

BC137-2 *Light chain*
*Nucleotide:* (SEQ ID NO: 98)
GACGTCGTGATGACACAGTCCCCTCTGTCCCTGCCTGTGACCCTGGGACAGCCTGCCTC
CATCTCCTGCAGATCCTCCCAGTCCCTGGTGCACTCCAACGGCAACACCTACCTGTACT
GGTATCTGCAGAAGCCCGGCCAGTCCCCCAAGCCCCTGATCTACAGAGTGTCCAACCG
GTTCTCCGGCGTGCCCGACAGATTCTCCGGCTCTGGCTCTGGCACCGACTTCACCCTGA
AGATCTCCCGGGTGGAAGCCGAGGACGTGGGCGTGTACTTCTGTTTTCAAGGCACCCA
CGTGCCCTACACCTTCGGCCAGGGCACCCGGCTGGAAATCAAGAGAACCGTGGCCGCT
CCCTCCGTGTTCATCTTCCCACCTTCCGACGAGCAGCTGAAGTCCGGCACCGCTTCTGT
CGTGTGCCTGCTGAACAACTTCTACCCCGCGAGGCCAAGGTGCAGTGGAAGGTGGAC
AACGCCCTGCAGTCCGGCAACTCCCAGGAATCCGTGACCGAGCAGGACTCCAAGGACA
GCACCTACTCCCTGTCCTCCACCCTGACCCTGTCCAAGGCCGACTACGAGAAGCACAA
GGTGTACGCCTGCGAAGTGACCCACCAGGGCCTGTCTAGCCCCGTGACCAAGTCTTTC
AACCGGGGCGAGTGCACTAGTGGCGGCGGAGGATCTGGCGGAGGTGGAAGTGGGGGA
GGCGGATCTCAGGTGCAGCTGGTGCAGAGTGGTGGCGGAGTGGTGCAGCCTGGCAGAT
CCCTGAGACTGTCTTGCAAGGCCAGCGGCTACACCTTCACCCGGTACACCATGCACTG
GGTGCGACAGGCCCCTGGCAAGGGCCTGGAATGGATCGGCTACATCAACCCCTCCCGG
GGCTACACCAACTACAACCAGAAGTTCAAGGACCGGTTCACCATCAGCCGGGACAACT
CCAAGAACACCGCCTTTCTGCAGATGGACTCCCTGCGGCCTGAGGATACCGGCGTGTA
CTTTTGCGCCCGGTACTACGACGACCACTACAGCCTGGACTACTGGGGCCAGGGAACC
CCTGTGACAGTGTCTAGCGGAGGGGGAGGTTCAGGTGGCGGTGGATCAGGGGGCGGA
GGAAGTGGCGGGGGAGGTAGTGGTGGTGGTGGAAGCGGAGGTGGCGGCTCCGATATC
CAGATGACCCAGTCCCCCTCCAGCCTGTCTGCCTCTGTGGGAGACAGAGTGACAATTA
CATGCTCCGCCAGCTCCAGCGTGTCCTACATGAATTGGTATCAGCAGACCCCTGGCAA
GGCTCCCAAGCGGTGGATCTACGACACCTCCAAGCTGGCCTCCGGCGTGCCCTCCAGA
TTTTCTGGCAGCGGCTCCGGCACAGACTATACCTTTACAATCAGCTCCCTGCAGCCCGA
AGATATCGCCACCTACTACTGCCAGCAGTGGTCCTCCAACCCCTTCACCTTCGGCCAGG
GCACAAAGCTGCAGATCACCAGATAGTCTAGA

Figure 35(A)

BC137 KS2 heavy chain
*Amino acid:* (SEQ ID NO: 51)
QIQLQQSGPEVVKPGASVKISCKASGYTFT<u>DYYIH</u>WVKQRPGQGLEWIG<u>WIYPGSGNTKY
NEKFEG</u>KATLTVDTSASTAHMELSSLTSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCAVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 35(B)

BC137 KS2 heavy chain
*Nucleotide:* (SEQ ID NO: 99)
CAGATCCAGCTGCAGCAGTCTGGACCCGAGGTCGTGAAGCCTGGCGCCTCCGTGAAGA
TCTCCTGCAAGGCCTCCGGCTACACCTTCACCGACTACTACATCCACTGGGTCAAGCAG
CGGCCAGGCCAGGGCCTGGAATGGATCGGCTGGATCTATCCCGGCTCCGGCAACACCA
AGTACAACGAGAAGTTCGAGGGCAAGGCCACCCTGACCGTGGACACCTCTGCCTCCAC
CGCCCACATGGAACTGTCCTCCCTGACCTCCGAGGATACCGCCGTGTACTTCTGTGCCA
GAGGCGGCAAGTTCGCCATGGACTATTGGGGCCAGGGCACCCTCGTGACCGTGTCTAG
CGCCTCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCCGTCCTACAG
TCCTCAGGACTCTACTCCCTCAGCAGCGTGGTGACAGTGCCCTCCAGCTCTCTGGGCAC
CCAGACCTACATCTGCAACGTGAACCACAAGCCCTCCAATACCAAGGTGGACAAGCGG
GTGGAACCCAAGTCCTGCGACAAGACCCACACCTGTCCCCCTTGTCCTGCCCCTGAACT
GCTGGGCGGACCTTCCGTGTTCCTGTTCCCCCCAAAGCCCAAGGACACCCTGATGATCT
CCCGGACCCCCGAAGTGACCTGCGTGGTGGTGGATGTGTCCCACGAGGACCCTGAAGT
GAAGTTCAATTGGTACGTGGACGGCGTGGAAGTGCACAACGCCAAGACCAAGCCTAG
AGAGGAACAGTACGCCTCCACCTACCGGGTGGTGTCCGTGCTGACAGTGCTGCACCAG
GACTGGCTGAACGGCAAAGAGTACAAGTGCGCCGTGTCCAACAAGGCCCTGCCTGCCC
CCATCGAAAAGACCATCTCCAAGGCCAAGGGCCAGCCCCGGGAACCCCAGGTGTACAC
ACTGCCCCCTAGCAGGGACGAGCTGACCAAGAACCAGGTGTCCCTGACCTGTCTCGTG
AAAGGCTTCTACCCCTCCGATATCGCCGTGGAATGGGAGTCCAACGGCCAGCCTGAGA
ACAACTACAAGACCACCCCCCTGTGCTGGACTCCGACGGCTCATTCTTCCTGTACAGC
AAGCTGACCGTGGACAAGTCCCGGTGGCAGCAGGGCAACGTGTTCTCCTGCTCCGTGA
TGCACGAGGCCCTGCACAACCACTACACCCAGAAGTCCCTGTCCCTGAGCCCCGGCAA
ATGA

Figure 35(C)

BC137 KS2 light chain
*Amino acid:* (SEQ ID NO: 52)
DVVMTQSPLSLPVTLGQPASISC<u>RSSQSLVHSNGNTYLY</u>WYLQKPGQSPKPLIY<u>RVSNRFSG</u>
VPCRFSGSGSGTDFTLKISRVETEDVGVYFC<u>FQGTHVPYI</u>FGQGTRLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGECTS<u>GGGGSGGGGSGGGGS</u>QVQLVQSG
GGVVQPGRSLRLSCKASGYTFTRYTMHWVRQAPGKCLEWIGYINPSRGYTNYNQKFKDR
FTISRDNSKNTAFLQMDSLRPEDTGVYFCARYYDDHYSLDYWGQGTPVTVSS<u>GGGGSGGG
GSGGGGSGGGGSGGGGSGGGGS</u>DIQMTQSPSSLSASVGDRVTITCSASSSVSYMNWYQQT
PGKAPKRWIYDTSKLASGVPSRFSGSGSGTDYTFTISSLQPEDIATYYCQQWSSNPFTFGCG
TKLQITR

Figure 35(D)

BC137 KS2 light chain
*Nucleotide:* (SEQ ID NO: 100)
GACGTCGTGATGACACAGTCCCCTCTGTCCCTGCCTGTGACCCTGGGACAGCCTGCCTC
CATCTCCTGCAGATCCTCCCAGTCCCTGGTGCACTCCAACGGCAACACCTACCTGTACT
GGTATCTGCAGAAGCCCGGCCAGTCCCCCAAGCCCCTGATCTACAGAGTGTCCAACCG
GTTCTCCGGCGTGCCCTGCAGATTCTCCGGCTCTGGCTCTGGCACCGACTTCACCCTGA
AGATCTCCCGGGTGGAAACCGAGGACGTGGGCGTGTACTTCTGTTTTCAAGGCACCCA
CGTGCCCTACATCTTCGGCCAGGGCACCCGGCTGGAAATCAAGCGGACCGTGGCCGCT
CCCTCCGTGTTCATCTTCCCACCTTCCGACGAGCAGCTGAAGTCCGGCACCGCTTCTGT
CGTGTGCCTGCTGAACAACTTCTACCCCGCGAGGCCAAGGTGCAGTGGAAGGTGGAC
AACGCCCTGCAGTCCGGCAACTCCCAGGAATCCGTGACCGAGCAGGACTCCAAGGACA
GCACCTACTCCCTGTCCTCCACCCTGACCCTGTCCAAGGCCGACTACGAGAAGCACAA
GGTGTACGCCTGCGAAGTGACCCACCAGGGCCTGTCTAGCCCCGTGACCAAGTCTTTC
AACCGGGGCGAGTGCACTAGTGGCGGCGGAGGATCTGGCGGAGGTGGAAGCGGAGGG
GGAGGATCTCAGGTGCAGCTGGTGCAGAGCGGAGGCGGAGTGGTGCAGCCTGGCAGA
TCCCTGAGACTGTCCTGCAAGGCCTCCGGCTACACCTTCACCCGGTACACCATGCACTG
GGTGCGACAGGCCCCTGGCAAGTGCCTGGAATGGATCGGCTACATCAACCCCTCCCGG
GGCTACACCAACTACAACCAGAAGTTCAAGGACCGGTTCACCATCTCCCGGGACAACT
CCAAGAACACCGCCTTTCTGCAGATGGACTCCCTGCGGCCTGAGGATACCGGCGTGTA
CTTCTGCGCCCGGTACTACGACGACCACTACTCCCTGGACTACTGGGGCCAGGGAACC
CTGTGACAGTGTCATCTGGTGGCGGAGGAAGTGGGGGAGGCGGATCAGGTGGTGGTG
GATCAGGCGGGGGAGGTTCAGGGGGTGGCGGTTCTGGGGGAGGGGGCTCTGATATTCA
GATGACTCAGAGCCCTTCCAGCCTGAGCGCCTCCGTGGGAGATCGCGTGACAATTACC
TGCTCTGCCTCCTCCTCCGTGTCTTACATGAATTGGTATCAGCAGACCCCTGGGAAGGC
TCCTAAGCGGTGGATCTACGACACCTCCAAGCTGGCCTCTGGCGTGCCCAGCAGGTTTT
CTGGCTCCGGCAGCGGCACAGATTATACCTTCACCATCAGCTCCCTGCAGCCAGAAGA
TATCGCTACCTATTATTGTCAGCAGTGGTCCTCCAACCCTTTCACCTTCGGCTGCGGCA
CAAAGCTGCAGATCACAAGATAG

Figure 36(A)

BC137 KS34 heavy chain
*Amino acid:* (SEQ ID NO: 53)
QIQLQQSGPEVVKPGASVKISCKASGYTFT<u>DYYIH</u>WVKQRPGQGLEWIG<u>WIYPGSGNTKY
NEKFKG</u>KATLTVDTSVSTAYMELSSLTSEDNAVYFCARG<u>GKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCAVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 36(B)

BC137 KS34 heavy chain
*Nucleotide:* (SEQ ID NO: 101)
CAGATCCAGCTGCAGCAGTCTGGACCCGAGGTCGTGAAGCCTGGCGCCTCCGTGAAGA
TCTCCTGCAAGGCCTCCGGCTACACCTTCACCGACTACTACATCCACTGGGTCAAGCAG
CGGCCAGGCCAGGGCCTGGAATGGATCGGCTGGATCTATCCCGGCTCCGGCAACACCA
AGTACAACGAGAAGTTCAAGGGCAAGGCCACCCTGACCGTGGACACCTCTGTCTCCAC
CGCCTACATGGAACTGTCCTCCCTGACCTCCGAGGATAACGCCGTGTACTTCTGTGCCA
GAGGCGGCAAGTTCGCCATGGACTATTGGGGCCAGGGCACCCTCGTGACCGTGTCTAG
CGCCTCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCCGTCCTACAG
TCCTCAGGACTCTACTCCCTCAGCAGCGTGGTGACAGTGCCCTCCAGCTCTCTGGGCAC
CCAGACCTACATCTGCAACGTGAACCACAAGCCCTCCAATACCAAGGTGGACAAGCGG
GTGGAACCCAAGTCCTGCGACAAGACCCACACCTGTCCCCCTTGTCCTGCCCCTGAACT
GCTGGGCGGACCTTCCGTGTTCCTGTTCCCCCCAAAGCCCAAGGACACCCTGATGATCT
CCCGGACCCCCGAAGTGACCTGCGTGGTGGTGGATGTGTCCCACGAGGACCCTGAAGT
GAAGTTCAATTGGTACGTGGACGGCGTGGAAGTGCACAACGCCAAGACCAAGCCTAG
AGAGGAACAGTACGCCTCCACCTACCGGGTGGTGTCCGTGCTGACAGTGCTGCACCAG
GACTGGCTGAACGGCAAAGAGTACAAGTGCGCCGTGTCCAACAAGGCCCTGCCTGCCC
CCATCGAAAAGACCATCTCCAAGGCCAAGGGCCAGCCCCGGGAACCCCAGGTGTACAC
ACTGCCCCCTAGCAGGGACGAGCTGACCAAGAACCAGGTGTCCCTGACCTGTCTCGTG
AAAGGCTTCTACCCCTCCGATATCGCCGTGGAATGGGAGTCCAACGGCCAGCCTGAGA
ACAACTACAAGACCACCCCCCCTGTGCTGGACTCCGACGGCTCATTCTTCCTGTACAGC
AAGCTGACCGTGGACAAGTCCCGGTGGCAGCAGGGCAACGTGTTCTCCTGCTCCGTGA
TGCACGAGGCCCTGCACAACCACTACACCCAGAAGTCCCTGTCCCTGAGCCCCGGCAA
ATGA

Figure 36(C)

BC137 KS34 light chain
*Amino acid:* (SEQ ID NO: 54)
DVVMTQSPLSLPVTLGQPASISC<u>RSSQSLVHSNGNTYLY</u>WYLQKPGQSPKPLIY<u>RVSNRFSG</u>
VPCRYSGSGSGTDFTLKISRVEAEDVGVYFC<u>FQGTHVPYT</u>FGQGTRLEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGECTS<u>GGGGSGGGGSGGGGS</u>QVQLVQS
GGGVVQPGRSLRLSCKASGYTFTRYTMHWVRQAPGKCLEWIGYINPSRGYTNYNQKFKD
RFTISRDNSKNTAFLQMDSLRPEDTGVYFCARYYDDHYSLDYWGQGTPVTVSS<u>GGGGSGG</u>
<u>GGSGGGGSGGGGSGGGGSGGGGS</u>DIQMTQSPSSLSASVGDRVTITCSASSSVSYMNWYQQ
TPGKAPKRWIYDTSKLASGVPSRFSGSGSGTDYTFTISSLQPEDIATYYCQQWSSNPFTFGC
GTKLQITR

Figure 36(D)

BC137 KS34 light chain
*Nucleotide:* (SEQ ID NO: 102)
GACGTCGTGATGACACAGTCCCCTCTGTCCCTGCCTGTGACCCTGGGACAGCCTGCCTC
CATCTCCTGCAGATCCTCCCAGTCCCTGGTGCACTCCAACGGCAACACCTACCTGTACT
GGTATCTGCAGAAGCCCGGCCAGTCCCCCAAGCCCCTGATCTACAGAGTGTCCAACCG
GTTCTCCGGCGTGCCCTGCAGATACTCCGGCTCTGGCTCTGGCACCGACTTCACCCTGA
AGATCTCCCGGGTGGAAGCCGAGGACGTGGGCGTGTACTTCTGTTTTCAAGGCACCCA
CGTGCCCTACACCTTCGGCCAGGGCACCCGGCTGGAAATCAAGCGGACCGTGGCCGCT
CCCTCCGTGTTCATCTTCCCACCTTCCGACGAGCAGCTGAAGTCCGGCACCGCTTCTGT
CGTGTGCCTGCTGAACAACTTCTACCCCGCGAGGCCAAGGTGCAGTGGAAGGTGGAC
AACGCCCTGCAGTCCGGCAACTCCCAGGAATCCGTGACCGAGCAGGACTCCAAGGACA
GCACCTACTCCCTGTCCTCCACCCTGACCCTGTCCAAGGCCGACTACGAGAAGCACAA
GGTGTACGCCTGCGAAGTGACCCACCAGGGCCTGTCTAGCCCCGTGACCAAGTCTTTC
AACCGGGGCGAGTGCACTAGTGGCGGCGGAGGATCTGGCGGAGGTGGAAGCGGAGGG
GGAGGATCTCAGGTGCAGCTGGTGCAGAGCGGAGGCGGAGTGGTGCAGCCTGGCAGA
TCCCTGAGACTGTCCTGCAAGGCCTCCGGCTACACCTTCACCCGGTACACCATGCACTG
GGTGCGACAGGCCCCTGGCAAGTGCCTGGAATGGATCGGCTACATCAACCCCTCCCGG
GGCTACACCAACTACAACCAGAAGTTCAAGGACCGGTTCACCATCTCCCGGGACAACT
CCAAGAACACCGCCTTTCTGCAGATGGACTCCCTGCGGCCTGAGGATACCGGCGTGTA
CTTCTGCGCCCGGTACTACGACGACCACTACTCCCTGGACTACTGGGGCCAGGGAACC
CCTGTGACAGTGTCATCTGGTGGCGGAGGAAGTGGGGGAGGCGGATCAGGTGGTGGTG
GATCAGGCGGGGGAGGTTCAGGGGGTGGCGGTTCTGGGGAGGGGGCTCTGATATTCA
GATGACTCAGAGCCCTTCCAGCCTGAGCGCCTCCGTGGGAGATCGCGTGACAATTACC
TGCTCTGCCTCCTCCTCCGTGTCTTACATGAATTGGTATCAGCAGACCCCTGGGAAGGC
TCCTAAGCGGTGGATCTACGACACCTCCAAGCTGGCCTCTGGCGTGCCCAGCAGGTTTT
CTGGCTCCGGCAGCGGCACAGATTATACCTTCACCATCAGCTCCCTGCAGCCAGAAGA
TATCGCTACCTATTATTGTCAGCAGTGGTCCTCCAACCCTTTCACCTTCGGCTGCGGCA
CAAAGCTGCAGATCACAAGATAG

Figure 37(A)

BC137 DS47 heavy chain
*Amino acid:* (SEQ ID NO: 55)
QIQLQQSGPEVVKPGASVKISCKASGYTFT<u>NYYIH</u>WVMQRPGQGLEWIG<u>RIYPGSGNTKY
NEKFKG</u>KATLTVDTSASTAYMELSSLTSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCAVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 37(B)

BC137 DS47 heavy chain
*Nucleotide:* (SEQ ID NO: 103)
CCGCCACCGGCCCAGATCCAGCTGCAGCAGTCTGGACCCGAGGTCGTGAAGCCTGGCG
CCTCCGTGAAGATCTCCTGCAAGGCCTCCGGCTACACCTTCACCAACTACTACATCCAC
TGGGTCATGCAGCGGCCAGGCCAGGGCCTGGAATGGATCGGCCGGATCTATCCCGGCT
CCGGCAACACCAAGTACAACGAGAAGTTCAAGGGCAAGGCCACCCTGACCGTGGACA
CCTCTGCCTCCACCGCCTACATGGAACTGTCCTCCCTGACCTCCGAGGATACCGCCGTG
TACTTCTGTGCCAGAGGCGGCAAGTTCGCCATGGACTATTGGGGCCAGGGCACCCTCG
TGACCGTGTCTAGCGCCTCCACCAAGGGCCCATCGGTCTTCCCCCTGGCACCCTCCTCC
AAGAGCACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTGCACACCTTCCC
GGCCGTCCTACAGTCCTCAGGACTCTACTCCCTCAGCAGCGTGGTGACAGTGCCCTCCA
GCTCTCTGGGCACCCAGACCTACATCTGCAACGTGAACCACAAGCCCTCCAATACCAA
GGTGGACAAGCGGGTGGAACCCAAGTCCTGCGACAAGACCCACACCTGTCCCCCTTGT
CCTGCCCCTGAACTGCTGGGCGGACCTTCCGTGTTCCTGTTCCCCCCAAAGCCCAAGGA
CACCCTGATGATCTCCCGGACCCCCGAAGTGACCTGCGTGGTGGTGGATGTGTCCCAC
GAGGACCCTGAAGTGAAGTTCAATTGGTACGTGGACGGCGTGGAAGTGCACAACGCCA
AGACCAAGCCTAGAGAGGAACAGTACGCCTCCACCTACCGGGTGGTGTCCGTGCTGAC
AGTGCTGCACCAGGACTGGCTGAACGGCAAAGAGTACAAGTGCGCCGTGTCCAACAA
GGCCCTGCCTGCCCCATCGAAAAGACCATCTCCAAGGCCAAGGGCCAGCCCCGGGAA
CCCCAGGTGTACACACTGCCCCCTAGCAGGGACGAGCTGACCAAGAACCAGGTGTCCC
TGACCTGTCTCGTGAAAGGCTTCTACCCCTCCGATATCGCCGTGGAATGGGAGTCCAAC
GGCCAGCCTGAGAACAACTACAAGACCACCCCCCCTGTGCTGGACTCCGACGGCTCAT
TCTTCCTGTACAGCAAGCTGACCGTGGACAAGTCCCGGTGGCAGCAGGGCAACGTGTT
CTCCTGCTCCGTGATGCACGAGGCCCTGCACAACCACTACACCCAGAAGTCCCTGTCCC
TGAGCCCCGGCAAATGA

Figure 38(A)

BC137 DS54 heavy chain
*Amino acid:* (SEQ ID NO: 56)
QIQLQQSGPEVVKPGASVKISCKASGYTFT<u>NYYIH</u>WVKQRPGQGLEWIG<u>RIYPGSGNTKYN
EKFKG</u>KATLTVDTSASTAYMELSSLTSEDTAVYFCAR<u>GGKFAMDY</u>WGQGTLVTVSSAST
KGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPREEQYASTYRVV
SVLTVLHQDWLNGKEYKCAVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSC
SVMHEALHNHYTQKSLSLSPGK

Figure 38(B)

BC137 DS54 heavy chain
*Nucleotide:* (SEQ ID NO: 104)
CAGATCCAGCTGCAGCAGTCTGGACCCGAGGTCGTGAAGCCTGGCGCCTCCGTTAAGA
TCTCCTGCAAGGCCTCCGGCTACACCTTCACCAACTACTACATCCACTGGGTCAAGCAG
CGGCCAGGCCAAGGCCTGGAATGGATCGGCCGGATCTATCCCGGCTCCGGCAACACCA
AGTACAACGAGAAGTTCAAGGGCAAGGCCACCCTGACCGTGGACACCTCTGCCTCCAC
CGCCTACATGGAACTGTCCTCCCTGACCTCCGAGGATACCGCCGTGTACTTCTGTGCCA
GAGGCGGCAAGTTCGCCATGGACTATTGGGGCCAGGGCACCCTCGTGACCGTGTCTAG
CGCCTCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCCGTCCTACAG
TCCTCAGGACTCTACTCCCTCAGCAGCGTGGTGACAGTGCCCTCCAGCTCTCTGGGCAC
CCAGACCTACATCTGCAACGTGAACCACAAGCCCTCCAATACCAAGGTGGACAAGCGG
GTGGAACCCAAGTCCTGCGACAAGACCCACACCTGTCCCCCTTGTCCTGCCCCTGAACT
GCTGGGCGGACCTTCCGTGTTCCTGTTCCCCCCAAAGCCCAAGGACACCCTGATGATCT
CCCGGACCCCCGAAGTGACCTGCGTGGTGGTGGATGTGTCCCACGAGGACCCTGAAGT
GAAGTTCAATTGGTACGTGGACGGCGTGGAAGTGCACAACGCCAAGACCAAGCCTAG
AGAGGAACAGTACGCCTCCACCTACCGGGTGGTGTCCGTGCTGACAGTGCTGCACCAG
GACTGGCTGAACGGCAAAGAGTACAAGTGCGCCGTGTCCAACAAGGCCCTGCCTGCCC
CCATCGAAAAGACCATCTCCAAGGCCAAGGGCCAGCCCCGGGAACCCCAGGTGTACAC
ACTGCCCCCTAGCAGGGACGAGCTGACCAAGAACCAGGTGTCCCTGACCTGTCTCGTG
AAAGGCTTCTACCCCTCCGATATCGCCGTGGAATGGGAGTCCAACGGCCAGCCTGAGA
ACAACTACAAGACCACCCCCCCTGTGCTGGACTCCGACGGCTCATTCTTCCTGTACAGC
AAGCTGACCGTGGACAAGTCCCGGTGGCAGCAGGGCAACGTGTTCTCCTGCTCCGTGA
TGCACGAGGCCCTGCACAACCACTACACCCAGAAGTCCCTGTCCCTGAGCCCCGGCAA
ATGA

Figure 39(A)

BC137 DS47 D31R heavy chain
*Amino acid:* (SEQ ID NO: 57)
QIQLQQSGPEVVKPGASVKISCKASGYTFTRYYIHWVMQRPGQGLEWIGRIYPGSGNTKY
NEKFKGKATLTVDTSASTAYMELSSLTSEDTAVYFCARGGKFAMDYWGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCAVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 39(B)

BC137 DS47 D31R heavy chain
*Nucleotide:* (SEQ ID NO: 105)
CAGATCCAGCTGCAGCAGTCTGGACCCGAGGTCGTGAAGCCTGGCGCCTCCGTGAAGA
TCTCCTGCAAGGCCTCCGGCTACACCTTCACCCGGTACTACATCCACTGGGTCATGCAG
CGGCCAGGCCAGGGCCTGGAATGGATCGGCCGGATCTATCCCGGCTCCGGCAACACCA
AGTACAACGAGAAGTTCAAGGGCAAGGCCACCCTGACCGTGGACACCTCTGCCTCCAC
CGCCTACATGGAACTGTCCTCCCTGACCTCCGAGGATACCGCCGTGTACTTCTGTGCCA
GAGGCGGCAAGTTCGCCATGGACTATTGGGGCCAGGGCACCCTCGTGACCGTGTCTAG
CGCCTCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCCGTCCTACAG
TCCTCAGGACTCTACTCCCTCAGCAGCGTGGTGACAGTGCCCTCCAGCTCTCTGGGCAC
CCAGACCTACATCTGCAACGTGAACCACAAGCCCTCCAATACCAAGGTGGACAAGCGG
GTGGAACCCAAGTCCTGCGACAAGACCCACACCTGTCCCCCTTGTCCTGCCCCTGAACT
GCTGGGCGGACCTTCCGTGTTCCTGTTCCCCCCAAAGCCCAAGGACACCCTGATGATCT
CCCGGACCCCCGAAGTGACCTGCGTGGTGGTGGATGTGTCCCACGAGGACCCTGAAGT
GAAGTTCAATTGGTACGTGGACGGCGTGGAAGTGCACAACGCCAAGACCAAGCCTAG
AGAGGAACAGTACGCCTCCACCTACCGGGTGGTGTCCGTGCTGACAGTGCTGCACCAG
GACTGGCTGAACGGCAAAGAGTACAAGTGCGCCGTGTCCAACAAGGCCCTGCCTGCCC
CCATCGAAAAGACCATCTCCAAGGCCAAGGGCCAGCCCCGGGAACCCCAGGTGTACAC
ACTGCCCCCTAGCAGGGACGAGCTGACCAAGAACCAGGTGTCCCTGACCTGTCTCGTG
AAAGGCTTCTACCCCTCCGATATCGCCGTGGAATGGGAGTCCAACGGCCAGCCTGAGA
ACAACTACAAGACCACCCCCCCTGTGCTGGACTCCGACGGCTCATTCTTCCTGTACAGC
AAGCTGACCGTGGACAAGTCCCGGTGGCAGCAGGGCAACGTGTTCTCCTGCTCCGTGA
TGCACGAGGCCCTGCACAACCACTACACCCAGAAGTCCCTGTCCCTGAGCCCCGGCAA
ATGA

Figure 40(A)

BC137 DS54 D31R heavy chain
*Amino acid:* (SEQ ID NO: 58)
QIQLQQSGPEVVKPGASVKISCKASGYTFT<u>RYYIH</u>WVKQRPGQGLEWIG<u>RIYPGSGNTKYN
EKFKG</u>KATLTVDTSASTAYMELSSLTSEDTAVYFCAR<u>GGKFAMDY</u>WGQGTLVTVSSAST
KGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPREEQYASTYRVV
SVLTVLHQDWLNGKEYKCAVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSC
SVMHEALHNHYTQKSLSLSPGK

Figure 40(B)

BC137 DS54 D31R heavy chain
*Nucleotide:* (SEQ ID NO: 106)
CAGATCCAGCTGCAGCAGTCTGGACCCGAGGTCGTGAAGCCTGGCGCCTCCGTTAAGA
TCTCCTGCAAGGCCTCCGGCTACACCTTCACCCGGTACTACATCCACTGGGTCAAGCAG
CGGCCAGGCCAAGGCCTGGAATGGATCGGCCGGATCTATCCCGGCTCCGGCAACACCA
AGTACAACGAGAAGTTCAAGGGCAAGGCCACCCTGACCGTGGACACCTCTGCCTCCAC
CGCCTACATGGAACTGTCCTCCCTGACCTCCGAGGATACCGCCGTGTACTTCTGTGCCA
GAGGCGGCAAGTTCGCCATGGACTATTGGGGCCAGGGCACCCTCGTGACCGTGTCTAG
CGCCTCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCCGTCCTACAG
TCCTCAGGACTCTACTCCCTCAGCAGCGTGGTGACAGTGCCCTCCAGCTCTCTGGGCAC
CCAGACCTACATCTGCAACGTGAACCACAAGCCCTCCAATACCAAGGTGGACAAGCGG
GTGGAACCCAAGTCCTGCGACAAGACCCACACCTGTCCCCCTTGTCCTGCCCCTGAACT
GCTGGGCGGACCTTCCGTGTTCCTGTTCCCCCCAAAGCCCAAGGACACCCTGATGATCT
CCCGGACCCCCGAAGTGACCTGCGTGGTGGTGGATGTGTCCCACGAGGACCCTGAAGT
GAAGTTCAATTGGTACGTGGACGGCGTGGAAGTGCACAACGCCAAGACCAAGCCTAG
AGAGGAACAGTACGCCTCCACCTACCGGGTGGTGTCCGTGCTGACAGTGCTGCACCAG
GACTGGCTGAACGGCAAAGAGTACAAGTGCGCCGTGTCCAACAAGGCCCTGCCTGCCC
CCATCGAAAAGACCATCTCCAAGGCCAAGGGCCAGCCCCGGGAACCCCAGGTGTACAC
ACTGCCCCCTAGCAGGGACGAGCTGACCAAGAACCAGGTGTCCCTGACCTGTCTCGTG
AAAGGCTTCTACCCCTCCGATATCGCCGTGGAATGGGAGTCCAACGGCCAGCCTGAGA
ACAACTACAAGACCACCCCCCTGTGCTGGACTCCGACGGCTCATTCTTCCTGTACAGC
AAGCTGACCGTGGACAAGTCCCGGTGGCAGCAGGGCAACGTGTTCTCCTGCTCCGTGA
TGCACGAGGCCCTGCACAACCACTACACCCAGAAGTCCCTGTCCCTGAGCCCCGGCAA
ATGA

Figure 41(A)

BC163 (polySia x DOTA bsAb)
*Heavy chain*
*Amino acid:* (SEQ ID NO: 59)
QIQLQQSGPEVVKPGASVKISCKASGYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCAVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 41(B)

BC163 (polySia x DOTA bsAb)
*Heavy chain*
*Nucleotide:* (SEQ ID NO: 107)
CAGATCCAGCTGCAGCAGTCTGGACCCGAGGTCGTGAAGCCTGGCGCCTCCGTGAAGA
TCTCCTGCAAGGCCTCCGGCTACACCTTCACCGACTACTACATCCACTGGGTCAAGCAG
CGGCCAGGCCAGGGCCTGGAATGGATCGGCTGGATCTATCCCGGCTCCGGCAACACCA
AGTACAACGAGAAGTTCAAGGGCAAGGCCACCCTGACCGTGGACACCTCTGCCTCCAC
CGCCTACATGGAACTGTCCTCCCTGACCTCCGAGGATACCGCCGTGTACTTCTGTGCCA
GAGGCGGCAAGTTCGCCATGGACTATGGGGCCAGGGCACCCTCGTGACCGTGTCTAG
CGCTTCTACCAAGGGCCCCTCTGTGTTTCCTCTGGCCCCCTCCAGCAAGTCCACCTCTG
GTGGAACAGCCGCCCTGGGCTGCCTCGTGAAGGACTACTTTCCCGAGCCCGTGACCGT
GTCCTGGAACTCTGGCGCTCTGACCTCTGGCGTGCACACCTTCCCTGCTGTGCTGCAGT
CTAGCGGCCTGTACTCCCTGTCCTCCGTCGTGACAGTGCCCTCCAGCTCTCTGGGCACC
CAGACCTACATCTGCAACGTGAACCACAAGCCCTCCAATACCAAGGTGGACAAGCGGG
TGGAACCCAAGTCCTGCGACAAGACCCACACCTGTCCCCCTTGTCCTGCCCCTGAACTG
CTGGGCGGACCTTCCGTGTTCCTGTTCCCCCCAAAGCCCAAGGACACCCTGATGATCTC
CCGGACCCCCGAAGTGACCTGCGTGGTGGTGGATGTGTCCCACGAGGACCCTGAAGTG
AAGTTCAATTGGTACGTGGACGGCGTGGAAGTGCACAACGCCAAGACCAAGCCTAGA
GAGGAACAGTACGCCTCCACCTACCGGGTGGTGTCCGTGCTGACAGTGCTGCACCAGG
ACTGGCTGAACGGCAAAGAGTACAAGTGCGCCGTGTCCAACAAGGCCCTGCCTGCCCC
CATCGAAAAGACCATCTCCAAGGCCAAGGGCCAGCCCCGGGAACCCCAGGTGTACAC
ACTGCCCCCTAGCAGGGACGAGCTGACCAAGAACCAGGTGTCCCTGACCTGTCTCGTG
AAAGGCTTCTACCCCTCCGATATCGCCGTGGAATGGGAGTCCAACGGCCAGCCTGAGA
ACAACTACAAGACCACCCCCCTGTGCTGGACTCCGACGGCTCATTCTTCCTGTACAGC
AAGCTGACCGTGGACAAGTCCCGGTGGCAGCAGGGCAACGTGTTCTCCTGCTCCGTGA
TGCACGAGGCCCTGCACAACCACTACACCCAGAAGTCCCTGTCCCTGAGCCCCGGCAA
ATGA

Figure 41(C)

BC163 (polySia x DOTA bsAb)
*Light chain - humanized P35 L2 – linker – huC825scFv*
*Amino acid:* (SEQ ID NO: 60)
DVVMTQSPLSLPVTLGQPASISC<u>RSSQSLVHSNGNTYLY</u>WYLQKPGQSPKPLIY<u>RVSNRFSG</u>
VPDRFSGSGSGTDFTLKISRVEAEDVGVYFC<u>FQGTHVPYT</u>FGQGTRLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGECTS<u>GGGGSGGGGSGGGGS</u>HVQLVESG
GGLVQPGGSLRLSCAASGFSLTDYGVHWVRQAPGKGLEWLGVIWSGGGTAYNTALISRFT
ISRDNSKNTLYLQMNSLRAEDTAVYYCARRGSYPYNYFDAWGCGTLVTVSS<u>GGGGSGGG
GSGGGGSGGGGSGGGGSGGGGS</u>QAVVTQEPSLTVSPGGTVTLTCGSSTGAVTASNYANW
VQQKPGQCPRGLIGGHNNRPPGVPARFSGSLLGGKAALTLLGAQPEDEAEYYCALWYSDH
WVIGGGTKLTVLG

Figure 41(D)

BC163 (polySia x DOTA bsAb)
*Light chain - humanized P35 L2 – linker – huC825scFv*
*Nucleotide:* (SEQ ID NO: 108)
GACGTCGTGATGACACAGTCCCCTCTGTCCCTGCCTGTGACCCTGGGACAGCCTGCCTC
CATCTCCTGCAGATCCTCCCAGTCCCTGGTGCACTCCAACGGCAACACCTACCTGTACT
GGTATCTGCAGAAGCCCGGCCAGTCCCCCAAGCCCCTGATCTACAGAGTGTCCAACCG
GTTCTCCGGCGTGCCCGACAGATTCTCCGGCTCTGGCTCTGGCACCGACTTCACCCTGA
AGATCTCCCGGGTGGAAGCCGAGGACGTGGGCGTGTACTTCTGTTTTCAAGGCACCCA
CGTGCCCTACACCTTCGGCCAGGGCACCCGGCTGGAAATCAAGAGAACCGTGGCCGCT
CCCTCCGTGTTCATCTTCCCACCTTCCGACGAGCAGCTGAAGTCCGGCACCGCTTCTGT
CGTGTGCCTGCTGAACAACTTCTACCCCGCGAGGCCAAGGTGCAGTGGAAGGTGGAC
AACGCCCTGCAGTCCGGCAACTCCCAGGAATCCGTGACCGAGCAGGACTCCAAGGACA
GCACCTACTCCCTGTCCTCCACCCTGACCCTGTCCAAGGCCGACTACGAGAAGCACAA
GGTGTACGCCTGCGAAGTGACCCACCAGGGCCTGTCTAGCCCCGTGACCAAGTCTTTC
AACCGGGGCGAGTGCACTAGTGGCGGCGGAGGATCTGGCGGAGGTGGAAGTGGGGGA
GGCGGATCTCATGTGCAGCTGGTGGAAAGCGGAGGCGGCCTGGTGCAGCCTGGGGGAT
CTCTGAGACTGTCTTGTGCCGCCAGCGGCTTCTCCCTGACCGATTATGGCGTGCACTGG
GTGCGACAGGCCCCTGGCAAAGGACTGGAATGGCTGGGAGTGATTTGGAGTGGCGGA
GGCACCGCCTACAACACCGCCCTGATCTCCCGGTTCACCATCAGCCGGGACAACTCCA
AGAACACCCTGTACCTGCAGATGAACTCCCTGCGGGCCGAGGACACCGCTGTGTACTA
CTGCGCCAGACGGGGCTCCTACCCCTACAACTACTTCGACGCTTGGGGCTGCGGCACC
CTCGTGACAGTGTCTAGCGGAGGGGGAGGTTCTGGGGGCGGAGGTTCAGGTGGTGGTG
GTTCCGGGGGTGGTGGCTCTGGTGGCGGTGGTTCTGGCGGTGGCGGATCTCAGGCTGT
CGTGACCCAGGAACCCAGCCTGACTGTGTCTCCTGGCGGAACCGTGACCCTGACCTGC
GGATCTTCTACCGGCGCTGTGACCGCCAGCAACTACGCCAATTGGGTGCAGCAGAAAC
CTGGACAGTGCCCTAGAGGCCTGATCGGCGGCCACAACAACAGACCTCCAGGCGTGCC
AGCCCGGTTCTCTGGATCTCTGCTGGGCGGAAAGGCCGCTCTGACACTGCTGGGTGCTC
AGCCTGAGGACGAGGCCGAGTACTACTGTGCCCTGTGGTACTCCGACCACTGGGTCAT
CGGAGGCGGGACCAAGCTGACCGTGCTGGGATAGT

Figure 42

Direct Screen 45 (DS45) ScFv (SEQ ID NO: 61)

QIQLQQSGPEVVKPGASVKISCKASGYTFT<u>GYYIH</u>WVKQRPGQGLEWIG<u>SIYPGSGNTKYN
EKFKG</u>KATLTVDTSASTAYMELSSLTSEDTAVYFCAR<u>GGKFAMDY</u>WGQGTLVTVSS<u>GGG
GSGGGGSGGGGS</u>DVVMTQSPLSLPVTLGQPASISCRSSQSLVHSNGNTYLYWYLQKPGQSP
KPLIYRVSNRFSGVPDRFSGSGSGTDFTLKISRVEAEDVGVYFCFQGTHVPYTFGQGTRLEI
KR

Figure 43

Direct Screen 47 (DS47) ScFv (SEQ ID NO: 62)

QIQLQQSGPEVVKPGASVKISCKASGYTFT<u>NYYIH</u>WVMQRPGQGLEWIG<u>RIYPGSGNTKY
NEKFKG</u>KATLTVDTSASTAYMELSSLTSEDTAVYFCAR<u>GGKFAMDY</u>WGQGTLVTVSS<u>GG
GGSGGGGSGGGGS</u>DVVMTQSPLSLPVTLGQPASISCRSSQSLVHSNGNTYLYWYLQKPGQ
SPKPLIYRVSNRFSGVPDRFSGSGSGTDFTLKISRVEAEDVGVYFCFQGTHVPYTFGQGTRL
EIKR

Figure 44

Direct Screen 51 (DS51) ScFv (SEQ ID NO: 63)

QIQLQQSGPEVVKPGASVKISCKASGYTFT<u>GYYIH</u>WVKQRPGQGLEWIG<u>CIYPGSGNTKYN
EKFKG</u>KATLTVDTSASTAYMELSSLTSEDTAVYFCAR<u>GGKFAMDY</u>WGQGTLVTVSS<u>GGG
GSGGGGSGGGGS</u>DVVMTQSPLSLPVTLGQPASISCRSSQSLVHSNGNTYLYWYLQKPGQSP
KPLIYRVSNRFSGVPDRFSGSGSGTDFTLKISRVEAEDVGVYFCFQGTHVPYTFGQGTRLEI
KR

Figure 45

Direct Screen 53 (DS53) ScFv (SEQ ID NO: 64)

QIQLQQSGPEVVKPGASVKISCKASGYTFT<u>DYYIH</u>WVMQRPGQGLEWIG<u>RIYPGSGNTKY
NEKFKG</u>KATLTVDTSASTAYMELSSLTSEDTAVYFCAR<u>GGKFAMDY</u>WGQGTLVTVSS<u>GG
GGSGGGGSGGGGS</u>DVVMTQSPLSLPVTLGQPASISCRSSQSLVHSNGNTYLYWYLQKPGQ
SPKPLIYRVSNRFSGVPDRFSGSGSGTDFTLKISRVEAEDVGVYFCFQGTHVPYTFGQGTRL
EIKR

Figure 46

Direct Screen 54 (DS54) ScFv (SEQ ID NO: 65)

QIQLQQSGPEVVKPGASVKISCKASGYTFT<u>NYYIH</u>WVKQRPGQGLEWIG<u>RIYPGSGNTKYN
EKFKG</u>KATLTVDTSASTAYMELSSLTSEDTAVYFCAR<u>GGKFAMDY</u>WGQGTLVTVSS<u>GGG
GSGGGGSGGGGS</u>DVVMTQSPLSLPVTLGQPASISCRSSQSLVHSNGNTYLYWYLQKPGQSP
KPLIYRVSNRFSGVPDRFSGSGSGTDFTLKISRVEAEDVGVYFCFQGTHVPYTFGQGTRLEI
KR

Figure 47

Direct Screen 55 (DS55) ScFv (SEQ ID NO: 66)

QIQLQQSGPEVVKPGASVKISCKASGYTFT<u>NYYIH</u>WVKQRPGQGLEWIG<u>CIYPGSGNTKYN
EKFKG</u>KATLTVDTSASTAYMELSSLTSEDTAVYFCAR<u>GGKFAMDY</u>WGQGTLVTVSS<u>GGG
GSGGGGSGGGGS</u>DVVMTQSPLSLPVTLGQPASISCRSSQSLVHSNGNTYLYWYLQKPGQSP
KPLIYRVSNRFSGVPDRFSGSGSGTDFTLKISRVEAEDVGVYFCFQGTHVPYTFGQGTRLEI
KR

Figure 48

Kinetic Screen 2 (KS2) ScFv (SEQ ID NO: 67)

QIQLQQSGPEVVKPGASVKISCKASGYTFT<u>DYYIH</u>WVKQRPGQGLEWIG<u>WIYPGSGNTKY
NEKFEG</u>KATLTVDTSASTAHMELSSLTSEDTAVYFCAR<u>GGKFAMDY</u>WGQGTLVTVSS<u>GG
GGSGGGGSGGGGS</u>DVVMTQSPLSLPVTLGQPASISCRSSQSLVHSNGNTYLYWYLQKPGQ
SPKPLIYRVSNRFSGVPCRFSGSGSGTDFTLKISRVETEDVGVYFCFQGTHVPYIFGQGTRLE
IKR

Figure 49

Kinetic Screen 10 (KS10) ScFv (SEQ ID NO: 68)

QIQLQQSGPEVVKPGASVKISCKASGYTFT<u>DYYIH</u>WVKQRPGQGLEWIG<u>CIYPGSGNTKYN
EKFKG</u>KATLTVDTSASTAYMELSSLTSEDTAVYFCAR<u>GGKFAMDY</u>WGQGTLVTVSS<u>GGG
GSGGGGSGGGGS</u>DVVMTQSPLSLPVTLGQPASISC<u>RSSQSLVHSNGNTYLY</u>WYLQKPGQSP
KPLIY<u>RVSNRFS</u>CVPDRFSGSGSGTDFTLKISRVEAEDVGVYFC<u>FQGTHVPYT</u>FGQGTRLEI
KR

Figure 50

Kinetic Screen 21 (KS21) ScFv (SEQ ID NO: 69)

QIQLQQSGPEVVKPGASVKISCKASGYTFT<u>DYYIH</u>CVKQRPGQGLEWIG<u>WIYPGSGNTKYN
EKFKG</u>KATLTVDTSASTAYMELSSLTSEDTAVYFCAR<u>GGKFAMDY</u>WGQGTLVTVSS<u>GGG
GSGGGGSGGGGS</u>DVVMTQSPLSLPVTLGQPASISC<u>RSSQSLVHSNGKTYLY</u>WYLQKPGQS
PKPLIY<u>RVSNRFS</u>CVPDRFSGSGSGTDFTLKISRVEAEDVGVYFC<u>FQGTHVPYT</u>FGQGTRLEI
KR

Figure 51

Kinetic Screen 23 (KS23) ScFv (SEQ ID NO: 70)

QIQLQQSGPEVVKPGASVKISCKASAYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSS<u>GG
GGS</u>GGGGSGGGGSDVVMTQSPLSLPVTLGQPASISC<u>RSSQSLVHSNGNTYLY</u>WYLQKPGQ
SPKPLIY<u>RVSNRFS</u>GVPCRFSGSGSGTDFTLKISRVEAEDVGVYFC<u>FQGTHVPYT</u>FGQGTRL
EIKR

Figure 52

Kinetic Screen 26 (KS26) ScFv (SEQ ID NO: 71)

QIQLQQSGPEVVKPGASVKISCKASGYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSS<u>GG
GGSGGGGSGGGGS</u>DVVMTQSPLSLPVTLGQPASISC<u>RSSQSLVHSNGNTYLY</u>WYLQKPGK
SPKPLIY<u>RVSNRFS</u>GVPDRFSGSGSGTDFTLKISRVEAKDVGVYFC<u>FQGTHVPYT</u>FGQGTRL
EIKR

Figure 53

Kinetic Screen 30 (KS30) ScFv (SEQ ID NO: 72)

QIQLQQSGPEVVKPGASVKISCKASGYTFT<u>DYYIH</u>WVKQRPGQGLEWIG<u>WIYPGSGNTKY
NEKFKG</u>KATLTVDTSASTAYMELSSLTSEDTAVYFCAR<u>GGKFAMDY</u>WGQGTLVTVSS<u>GG
GGSGGGGSGGGGS</u>DVVMTQSPLSLPVTLGQPVSISC<u>RSSQSLVHSNGNTYLY</u>WYLQKPGQ
SPKPLIY<u>RVSNRFS</u>GVPCRFSGSGSGTDFTLKISRVEAEDVGVYFC<u>FQGTHFPYT</u>FGQGTRL
EIKR

Figure 54

Kinetic Screen (KS34) ScFv (SEQ ID NO: 73)

QIQLQQSGPEVVKPGASVKISCKASGYTFT<u>DYYIH</u>WVKQRPGQGLEWIG<u>WIYPGSGNTKY
NEKFKG</u>KATLTVDTSVSTAYMELSSLTSEDNAVYFCAR<u>GGKFAMDY</u>WGQGTLVTVSS<u>GG
GGSGGGGSGGGGS</u>DVVMTQSPLSLPVTLGQPASISC<u>RSSQSLVHSNGNTYLY</u>WYLQKPGQ
SPKPLIY<u>RVSNRFS</u>GVPCRYSGSGSGTDFTLKISRVEAEDVGVYFC<u>FQGTHVPYT</u>FGQGTRL
EIKR

Figure 55

Re-humanized HP35 HC1 heavy chain (SEQ ID NO: 74)

QIQLQQSGAEVKKPGASVKVSCKASGYTFT<u>DYYIH</u>WVKQAPGQRLEWIG<u>WIYPGSGNTKY
NQKFQG</u>RVTLTVDTSASTAYMELSSLRSEDTAVYYCAR<u>GGKFAMD</u>YWGQGTSVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 56

Re-humanized HP35 HC2 heavy chain (SEQ ID NO: 75)

QVQLQQSGAEVKKPGASVKISCKASGYTFT<u>DYYIH</u>WVRQAPGQRLEWMG<u>WIYPGSGNTK
YSQKFQG</u>RATLTVDTSASTAYMELSSLRSEDTAVYFCAR<u>GGKFAMDY</u>WGQGTSVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNV
FSCSVMHEALHNHYTQKSLSLSPGK

Figure 57

Re-humanized HP35 HC3 heavy chain (SEQ ID NO: 76)

QIQLQQSGPEVVKPGASVKISCKASGYTFT<u>DYYIH</u>WVRQAPGQRLEWMG<u>WIYPGSGNTKY
SEKFQG</u>RVTITRDTSASTAYMELSSLRSEDTAVYFCAR<u>GGKFAMDY</u>WGQGTSVTVSSAST
KGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSC
SVMHEALHNHYTQKSLSLSPGK

Figure 58

Re-humanized HP35 HC4 heavy chain (SEQ ID NO: 77)

QVQLVQSGPEVKKPGASVKISCKASGYTFT<u>DYYIH</u>WVRQAPGQRLEWIG<u>WIYPGSGNTKY
SQKFQG</u>KATITVDTSASTAYMELSSLRSEDTAVYYCAR<u>GGKFAMDY</u>WGQGTSVTVSSAST
KGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSC
SVMHEALHNHYTQKSLSLSPGK

Figure 59

Re-humanized HP35 HC5 heavy chain (SEQ ID NO: 78)

QIQLVQSGAEVKKPGASVKVSCKASGYTFT<u>DYYIH</u>WVRQAPGQGLEWIG<u>WIYPGSGNTKY
SQKFKG</u>RATLTRDTSASTAYMELSSLRSEDTAVYFCAR<u>GGKFAMDY</u>WGQGTSVTVSSAST
KGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSC
SVMHEALHNHYTQKSLSLSPGK

Figure 60

Re-humanized HP35 HC6 heavy chain (SEQ ID NO: 79)

QIQLQQSGAEVKKPGASVKISCKASGYTFT<u>DYYIH</u>WVRQAPGQRLEWIG<u>WIYPGSGNTKY
SQKFQG</u>RATLTVDTSASTAYMELSSLRSEDTAVYYCAR<u>GGKFAMDY</u>WGQGTSVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 61

Re-humanized HP35 HC7 heavy chain (SEQ ID NO: 80)

QIQLQQSGAEVKKPGASVKVSCKASGYTFT<u>DYYIH</u>WVRQAPGQRLEWMG<u>WIYPGSGNTK
YNEKFKG</u>RATITVDTSASTAYMELSSLRSEDTAVYYCAR<u>GGKFAMDY</u>WGQGTSVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 62

Re-humanized HP35 HC8 heavy chain (SEQ ID NO: 81)

QVQLVQSGAEVKKPGASVKISCKASGYTFT<u>DYYIH</u>WVRQAPGQRLEWIG<u>WIYPGSGNTKY
NEKFKG</u>RVTLTVDTSASTAYMELSSLRSEDTAVYYCAR<u>GGKFAMDY</u>WGQGTSVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFS
CSVMHEALHNHYTQKSLSLSPGK

Figure 63

Re-humanized HP35 LC1 light chain (SEQ ID NO: 82)

DVVMTQSPLSLPVTLGQPASISC<u>RSSQSLVHSNGNTYLY</u>WYQQRPGQSPRRLIY<u>RVSNRFS</u>
GVPDRFSGSGSGTDFTLKISRVEAEDVGVYFC<u>FQGTHVPYT</u>FGGGTRLEIKRTVAAPSVFIF
PPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

Figure 64

Re-humanized HP35 LC2 light chain (SEQ ID NO: 83)

DVVMTQSPLSLPVTLGQPASISC<u>RSSQSLVHSNGNTYLY</u>WYQQRPGQSPRPLIY<u>RVSNRFSG</u>
VPDRFSGSGSGTDFTLKISRVEAEDVGVYYC<u>FQGTHVPYT</u>FGGGTRLEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

Figure 65

Re-humanized HP35 LC3 light chain (SEQ ID NO: 84)

DVVMTQSPLSLPVTLGQPASISC<u>RSSQSLVHSNGNTYLY</u>WFQQRPGQSPRPLIY<u>RVSNRFSG</u>
VPDRFSGSGSGTDFTLKISRVEAEDVGVYFC<u>FQGTHVPYT</u>FGGGTRLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Figure 68

| Sample | MFI | Binding Affinity | Stability |
|---|---|---|---|
| HP35_chimeric | | | |
| HP35_LC1+HC1 | | | |
| HP35_LC1+HC2 | | | |
| HP35_LC1+HC3 | | | |
| HP35_LC1+HC4 | | | |
| HP35_LC1+HC5 | | | |
| HP35_LC1+HC6 | | | |
| HP35_LC1+HC7 | | | |
| HP35_LC1+HC8 | | | |
| HP35_LC2+HC1 | | | |
| HP35_LC2+HC2 | | | |
| HP35_LC2+HC3 | | | |
| HP35_LC2+HC4 | | | |
| HP35_LC2+HC5 | | | |
| HP35_LC2+HC6 | | | |
| HP35_LC2+HC7 | | | |
| HP35_LC2+HC8 | | | |
| HP35_LC3+HC1 | | | |
| HP35_LC3+HC2 | | | |
| HP35_LC3+HC3 | | | |
| HP35_LC3+HC4 | | | |
| HP35_LC3+HC5 | | | |
| HP35_LC3+HC6 | | | |
| HP35_LC3+HC7 | | | |
| HP35_LC3+HC8 | | | |

ANTI-POLYSIALIC ACID ANTIBODIES AND USES THEREOF

CROSS-REFERENCE TO RELATED APPLICATIONS

This application is a U.S. National Stage Application of PCT/US2019/022037, filed on Mar. 13, 2019, which claims the benefit of and priority to U.S. provisional Patent Application No. 62/643,141, filed on Mar. 14, 2018, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 3, 2018, is named 115872-0474_SL.TXT and is 227,731 bytes in size.

TECHNICAL FIELD

The present technology relates generally to the preparation of immunoglobulin-related compositions (e.g., antibodies or antigen binding fragments thereof) that specifically bind polysialic acid and uses of the same. In particular, the present technology relates to the preparation of polysialic acid neutralizing antibodies and their use in detecting and treating polysialic acid-associated cancers.

BACKGROUND

The following description of the background of the present technology is provided simply as an aid in understanding the present technology and is not admitted to describe or constitute prior art to the present technology.

Aberrant glycosylation has long been considered a hallmark of cancer (Hakomori, S. (1994) *Prog Brain Res* 101, 241-250). Tumor associated carbohydrate antigens have been shown to be involved with tumor proliferation, invasion, angiogenesis, metastasis and immunity. Sialic acids (also known as N-acetylneuraminic acids), in particular, are carbohydrate units that have shown particular relevance and are contained in several cancer associate glycolipids, including gangliosides GD2, GD3, GM1, GM2 and GM3 (Daniotti, J. L., et al. (2013) *Front Oncol* 3, 306).

SUMMARY OF THE PRESENT TECHNOLOGY

In one aspect, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence selected from the group consisting of: DYYIH (SEQ ID NO: 1), RYYIH (SEQ ID NO: 7), GYYIH (SEQ ID NO: 8), and NYYIH (SEQ ID NO: 9), a $V_H$-CDR2 sequence selected from the group consisting of: WIYPGSGNTKYNEKFKG (SEQ ID NO: 2), SIYPGSGNTKYNEKFKG (SEQ ID NO: 10), RIYPGSGNTKYNEKFKG (SEQ ID NO: 11), CIYPGSGNTKYNEKFKG (SEQ ID NO: 12), WIYPGSGNTKYNEKFEG (SEQ ID NO: 13), WIYPGSGNTKYNQKFQG (SEQ ID NO: 14), WIYPGSGNTKYSQKFQG (SEQ ID NO: 15), WIYPGSGNTKYSEKFQG (SEQ ID NO: 16), and WIYPGSGNTKYSQKFKG (SEQ ID NO: 18), and a $V_H$-CDR3 sequence of GGKFAMDY (SEQ ID NO:3); and/or (b) the $V_L$ comprises a $V_L$-CDR1 sequence selected from the group consisting of: RSSQSLVHSNGNTYLY (SEQ ID NO: 4) and RSSQSLVHSNGKTYLY (SEQ ID NO: 20), a $V_L$-CDR2 sequence of RVSNRFS (SEQ ID NO: 5), and a $V_L$-CDR3 sequence selected from the group consisting of: FQGTHVPYT (SEQ ID NO: 6), FQGTHVPYI (SEQ ID NO: 21), and FQGTHEPYT (SEQ ID NO: 22).

In some embodiments, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence of SEQ ID NO: 1, a $V_H$-CDR2 sequence of SEQ ID NO: 2, a $V_H$-CDR3 sequence of SEQ ID NO: 3; and/or (b) the $V_L$ comprises a $V_L$-CDR1 sequence, a $V_L$-CDR2 sequence, and a $V_L$-CDR3 sequence selected from the group consisting of: SEQ ID NO: 4, SEQ ID NO: 5, and SEQ ID NO: 6; SEQ ID NO: 20, SEQ ID NO: 5, and SEQ ID NO: 6; SEQ ID NO: 4, SEQ ID NO: 5, and SEQ ID NO: 22.

In some embodiments, the present disclosure provides an antibody or antigen binding fragment thereof comprising a light chain immunoglobulin variable domain ($V_L$) and a heavy chain immunoglobulin variable domain ($V_H$), wherein (a) the $V_L$ comprises a $V_L$-CDR1 sequence of SEQ ID NO: 4, a $V_L$-CDR2 sequence of SEQ ID NO: 5, a $V_L$-CDR3 sequence of SEQ ID NO: 6; and/or (b) the $V_H$ comprises a $V_H$-CDR1 sequence, a $V_H$-CDR2 sequence, and a $V_H$-CDR3 sequence selected from the group consisting of: SEQ ID NO: 1, SEQ ID NO: 2, SEQ ID NO: 3; SEQ ID NO: 1, SEQ ID NO: 11, and SEQ ID NO: 3; SEQ ID NO: 1, SEQ ID NO: 12, SEQ ID NO: 3; SEQ ID NO: 1, SEQ ID NO: 13, and SEQ ID NO: 3; SEQ ID NO: 7, SEQ ID NO: 2, and SEQ ID NO: 3; SEQ ID NO: 7, SEQ ID NO: 11, and SEQ ID NO: 3; SEQ ID NO: 8, SEQ ID NO: 10, and SEQ ID NO: 3; SEQ ID NO: 8, SEQ ID NO: 12, and SEQ ID NO: 3; SEQ ID NO: 9, SEQ ID NO: 11, and SEQ ID NO: 3; SEQ ID NO: 9, SEQ ID NO: 12, and SEQ ID NO: 3; SEQ ID NO: 1, SEQ ID NO: 14, and SEQ ID NO: 3; SEQ ID NO: 1, SEQ ID NO: 15, and SEQ ID NO: 3; SEQ ID NO: 1, SEQ ID NO: 16, and SEQ ID NO: 3; and SEQ ID NO: 1, SEQ ID NO: 18, and SEQ ID NO: 3.

In some embodiments, the present disclosure provides an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence, a $V_H$-CDR2 sequence, and a $V_H$-CDR1 sequence, and the $V_L$ comprises a $V_L$-CDR1 sequence, a $V_L$-CDR2 sequence, and a $V_L$-CDR3 sequence, selected from the group consisting of: a) SEQ ID NOS: 1, 2, 3, 4, 5, and 6, respectively; b) SEQ ID NOS: 1, 2, 3, 4, 5, and 22, respectively; c) SEQ ID NOS: 1, 2, 3, 20, 5, and 6, respectively; d) SEQ ID NOS: 1, 11, 3, 4, 5, and 6, respectively; e) SEQ ID NOS: 1, 12, 3, 4, 5, and 6, respectively; f) SEQ ID NOS: 1, 13, 3, 4, 5, and 6, respectively; g) SEQ ID NOS: 1, 13, 3, 4, 5, and 21, respectively; h) SEQ ID NOS: 7, 2, 3, 4, 5, and 6, respectively; i) 7, 11, 3, 4, 5, and 6, respectively; j) SEQ ID NOS: 8, 10, 3, 4, 5, and 6, respectively; k) 8, 12, 3, 4, 5, and 6, respectively; l) SEQ ID NOS: 9, 11, 3, 4, 5, and 6, respectively; and m) SEQ ID NOS: 9, 12, 3, 4, 5, and 6, respectively.

The antibody may further comprise an Fc domain of an isotype selected from the group consisting of IgG1, IgG2, IgG3, IgG4, IgA1, IgA2, IgM, IgD, and IgE. In some embodiments, the antibody comprises an IgG1 constant region comprising one or more amino acid substitutions selected from the group consisting of N297A and K322A. Additionally or alternatively, in some embodiments, the antibody comprises an IgG4 constant region comprising a S228P mutation. In certain embodiments, the antigen binding fragment is selected from the group consisting of Fab, F(ab')$_2$, Fab', scF$_v$, and F$_v$. In some embodiments, the antibody is a monoclonal antibody, chimeric antibody, humanized antibody, or a bispecific antibody. In certain embodiments, the antibody or antigen binding fragment binds to polySia with a high degree of polymerization (high DP polySia) (e.g. a DP of about 10-20 Sia units, about 20-30 Sia units, about 30-50 Sia units, about 50-70 Sia units, about 70-100 Sia units, about 100-200 Sia units, or about 200-400 Sia units). In some embodiments, the antibody or antigen binding fragment binds to high DP polySia, e.g., with a DP>10, DP>20, DP>50, DP>100, or DP>200. In some embodiments, the epitope is a conformational epitope that is specific to high DP polySia. In some embodiments, the conformational epitope includes, 3 or more Sia units. In some embodiments, the 3 or more Sia units may be consecutive units. In some embodiments, the antibody or antigen binding fragment binds to polySia with a DP>10, and has higher affinity with increasing DP. Without wishing to be bound by theory, it is hypothesized that the antibody or antigen binding fragment disclosed herein binds cooperatively with two Fab arms to a single high DP polySia, based on the co-crystal structure of mAb735 scFv which showed two scFvs bound to one octasialic acid, where each scFv made contact with 3 out of the 8 Sia units (Nagae, M. et al. *J Biol Chem.* 288(47):33784-96 (2013)).

In another aspect, the present disclosure provides an antibody comprising a heavy chain (HC) amino acid sequence comprising SEQ ID NO: 23, SEQ ID NO: 25, SEQ ID NO: 26, SEQ ID NO: 29, SEQ ID NO: 48, SEQ ID NO: 51, SEQ ID NO: 53, SEQ ID NO: 55, SEQ ID NO: 56, SEQ ID NO: 57, SEQ ID NO: 58, SEQ ID NO: 59, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, or a variant thereof having one or more conservative amino acid substitutions, and/or a light chain (LC) amino acid sequence comprising SEQ ID NO: 24, SEQ ID NO: 27, SEQ ID NO: 28, SEQ ID NO: 49, SEQ ID NO: 50, SEQ ID NO: 52, SEQ ID NO: 54, SEQ ID NO: 60, SEQ ID NO: 82, SEQ ID NO: 83, SEQ ID NO: 84, or a variant thereof having one or more conservative amino acid substitutions.

In certain embodiments, the antibody comprises a HC amino acid sequence and a LC amino acid sequence selected from the group consisting of: SEQ ID NO: 23 and SEQ ID NO: 24 (chimeric P35); SEQ ID NO: 25 and SEQ ID NO: 28 (humanized P35 H1L2); SEQ ID NO: 25 and SEQ ID NO: 27 (humanized P35 H1L1); SEQ ID NO: 26 and SEQ ID NO: 28 (humanized P35 H2L2); SEQ ID NO: 26 and SEQ ID NO: 27 (humanized P35 H2L1); SEQ ID NO: 48 and SEQ ID NO: 49 (BC137); SEQ ID NO: 51 and SEQ ID NO: 52 (BC137 KS2); SEQ ID NO: 53 and SEQ ID NO: 54 (BC137 KS34); SEQ ID NO: 55 and SEQ ID NO: 49 (BC137 DS47); SEQ ID NO: 56 and SEQ ID NO: 49 (BC137 DS54); SEQ ID NO: 57 and SEQ ID NO: 49 (BC137 DS47 D31R); SEQ ID NO: 58 and SEQ ID NO: 49 (BC137 DS54 D31R); SEQ ID NO: 55 and SEQ ID NO: 50 (BC137-2 DS47); SEQ ID NO: 56 and SEQ ID NO: 50 (BC137-2 DS54); SEQ ID NO: 59 and SEQ ID NO: 60 (BC163); SEQ ID NO: 74 and SEQ ID NO: 82 (rehumanized P35H1L1); SEQ ID NO: 75 and SEQ ID NO: 82 (rehumanized P35H2L1); SEQ ID NO: 76 and SEQ ID NO: 82 (rehumanized P35H3L1); SEQ ID NO: 77 and SEQ ID NO: 82 (rehumanized P35H4L1); SEQ ID NO: 78 and SEQ ID NO: 82 (rehumanized P35H5L1); SEQ ID NO: 79 and SEQ ID NO: 82 (rehumanized P35H6L1); SEQ ID NO: 80 and SEQ ID NO: 82 (rehumanized P35H7L1); SEQ ID NO: 81 and SEQ ID NO: 82 (rehumanized P35H8L1); SEQ ID NO: 74 and SEQ ID NO: 83 (rehumanized P35H1L2); SEQ ID NO: 75 and SEQ ID NO: 83 (rehumanized P35H2L2); SEQ ID NO: 76 and SEQ ID NO: 83 (rehumanized P35H3L2); SEQ ID NO: 77 and SEQ ID NO: 83 (rehumanized P35H4L2); SEQ ID NO: 78 and SEQ ID NO: 83 (rehumanized P35H5L2); SEQ ID NO: 79 and SEQ ID NO: 83 (rehumanized P35H6L2); SEQ ID NO: 80 and SEQ ID NO: 83 (rehumanized P35H7L2); SEQ ID NO: 81 and SEQ ID NO: 83 (rehumanized P35H8L2); SEQ ID NO: 74 and SEQ ID NO: 84 (rehumanized P35H1L3); SEQ ID NO: 75 and SEQ ID NO: 84 (rehumanized P35H2L3); SEQ ID NO: 76 and SEQ ID NO: 84 (rehumanized P35H3L3); SEQ ID NO: 77 and SEQ ID NO: 84 (rehumanized P35H4L3); SEQ ID NO: 78 and SEQ ID NO: 84 (rehumanized P35H5L3); SEQ ID NO: 79 and SEQ ID NO: 84 (rehumanized P35H6L3); SEQ ID NO: 80 and SEQ ID NO: 84 (rehumanized P35H7L3); and SEQ ID NO: 81 and SEQ ID NO: 84 (rehumanized P35H8L3), respectively.

In one aspect, the present disclosure provides an antibody comprising (a) the light chain immunoglobulin variable domain sequence is at least 80%, at least 85%, at least 90%, at least 95%, or at least 99% identical to the light chain immunoglobulin variable domain sequence present in any one of SEQ ID NOs: 37, 39, 41, 43, 44, 45, 47, 24, 27, 28, 49, 50, 52, 54, 60, 82, 83, or 84; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 30, 31, 32, 33, 34, 35, 36, 38, 40, 42, 46, 23, 25, 26, 29, 48, 51, 53, 55, 56, 57, 58, 59, 74, 75, 76, 77, 78, 79, 80, or 81.

In another aspect, the present disclosure provides an antibody comprising (a) a LC sequence that is at least 80%, at least 85%, at least 90%, at least 95%, or at least 99% identical to the LC sequence present in any one of SEQ ID NOs: 24, 27, 28, 49, 50, 52, 54, 60, 82, 83, or 84; and/or (b) a HC sequence that is at least 80%, at least 85%, at least 90%, at least 95%, or at least 99% identical to the HC sequence present in any one of SEQ ID NOs: 23, 25, 26, 29, 48, 51, 53, 55, 56, 57, 58, 59, 74, 75, 76, 77, 78, 79, 80, or 81.

In any of the above embodiments, the antibody is a chimeric antibody, a humanized antibody, or a bispecific antibody. Additionally or alternatively, in some embodiments, the antibody comprises an IgG1 constant region comprising one or more amino acid substitutions selected from the group consisting of N297A and K322A. In certain embodiments, the antibody of the present technology comprises an IgG4 constant region comprising a S228P mutation. In any of the above embodiments, the antibody binds to high DP polySia (e.g. a DP of about 10-20 Sia units, about 20-30 Sia units, about 30-50 Sia units, about 50-70 Sia units, about 70-100 Sia units, about 100-200 Sia units, or about 200-400 Sia units). In some embodiments, the antibody or antigen binding fragment binds to high DP polySia, e.g., with a DP>10, DP>20, DP>50, DP>100, or DP>200. In some embodiments, the epitope is a conformational epitope that is specific to high DP polySia. In some embodiments, the conformational epitope includes, 3 or more Sia units. In some embodiments, the 3 or more Sia units may be consecutive units. Additionally or alternatively, in some embodiments, the antibody of the present technology lacks α-1,6-fucose modifications. In certain embodiments, the antibody or antigen binding fragment recruits T cells for T cell dependent cytotoxicity (TDCC) against polySia-expressing tumor cells. In some embodiments, the polySia-expressing tumor cells are resistant to polySia-specific antibody-dependent cell-mediated cytotoxicity (ADCC).

In one aspect, the present disclosure provides a recombinant nucleic acid sequence encoding any of the antibodies described herein. In some embodiments, the recombinant nucleic acid sequence selected from the group consisting of: SEQ ID NOs: 92-108.

In another aspect, the present disclosure provides a host cell or vector comprising any of the recombinant nucleic acid sequences disclosed herein.

In one aspect, the present disclosure provides a composition comprising an antibody or antigen binding fragment of the present technology and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In some embodiments of the bispecific antibody of the present technology, the bispecific antibody binds to T cells, B-cells, myeloid cells, plasma cells, or mast-cells. Additionally or alternatively, in some embodiments, the bispecific antibody binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten. The small molecule DOTA hapten may be selected from the group consisting of DOTA, DOTA-Bn, DOTA-desferrioxamine, DOTA-Phe-Lys(HSG)-D-Tyr-Lys(HSG)-NH$_2$, Ac-Lys(HSG)D-Tyr-Lys(HSG)-Lys (Tscg-Cys)-NH$_2$, DOTA-D-Asp-D-Lys(HSG)-D-Asp-D-Lys(HSG)-NH$_2$; DOTA-D-Glu-D-Lys(HSG)-D-Glu-D-Lys (HSG)-NH$_2$, DOTA-D-Tyr-D-Lys(HSG)-D-Glu-D-Lys (HSG)-NH$_2$, DOTA-D-Ala-D-Lys(HSG)-D-Glu-D-Lys (HSG)-NH$_2$, DOTA-D-Phe-D-Lys(HSG)-D-Tyr-D-Lys (HSG)-NH$_2$, Ac-D-Phe-D-Lys(DOTA)-D-Tyr-D-Lys (DOTA)-NH$_2$, Ac-D-Phe-D-Lys(DTPA)-D-Tyr-D-Lys (DTPA)-NH$_2$, Ac-D-Phe-D-Lys(Bz-DTPA)-D-Tyr-D-Lys (Bz-DTPA)-NH$_2$, Ac-D-Lys(HSG)-D-Tyr-D-Lys(HSG)-D-Lys(Tscg-Cys)-NH$_2$, DOTA-D-Phe-D-Lys(HSG)-D-Tyr-D-Lys(HSG)-D-Lys(Tscg-Cys)-NH$_2$, (Tscg-Cys)-D-Phe-D-Lys(HSG)-D-Tyr-D-Lys(HSG)-D-Lys(DOTA)-NH$_2$, Tscg-D-Cys-D-Glu-D-Lys(HSG)-D-Glu-D-Lys(HSG)-NH$_2$, (Tscg-Cys)-D-Glu-D-Lys(HSG)-D-Glu-D-Lys(HSG)-NH$_2$, Ac-D-Cys-D-Lys(DOTA)-D-Tyr-D-Ala-D-Lys(DOTA)-D-Cys-NH$_2$, Ac-D-Cys-D-Lys(DTPA)-D-Tyr-D-Lys(DTPA)-NH$_2$, Ac-D-Lys(DTPA)-D-Tyr-D-Lys(DTPA)-D-Lys(Tscg-Cys)-NH$_2$, and Ac-D-Lys(DOTA)-D-Tyr-D-Lys(DOTA)-D-Lys(Tscg-Cys)-NH$_2$.

In another aspect, the present disclosure provides a method for treating a polySia associated cancer in a subject in need thereof, comprising administering to the subject an effective amount of any one of the antibodies disclosed herein. In certain embodiments, the antibody comprises a HC amino acid sequence and a LC amino acid sequence selected from the group consisting of: SEQ ID NO: 23 and SEQ ID NO: 24 (chimeric P35); SEQ ID NO: 25 and SEQ ID NO: 28 (humanized P35 H1L2); SEQ ID NO: 25 and SEQ ID NO: 27 (humanized P35 H1L1); SEQ ID NO: 26 and SEQ ID NO: 28 (humanized P35 H2L2); SEQ ID NO: 26 and SEQ ID NO: 27 (humanized P35 H2L1); SEQ ID NO: 48 and SEQ ID NO: 49 (BC137); SEQ ID NO: 51 and SEQ ID NO: 52 (BC137 KS2); SEQ ID NO: 53 and SEQ ID NO: 54 (BC137 KS34); SEQ ID NO: 55 and SEQ ID NO: 49 (BC137 DS47); SEQ ID NO: 56 and SEQ ID NO: 49 (BC137 DS54); SEQ ID NO: 57 and SEQ ID NO: 49 (BC137 DS47 D31R); SEQ ID NO: 58 and SEQ ID NO: 49 (BC137 DS54 D31R); SEQ ID NO: 55 and SEQ ID NO: 50 (BC137-2 DS47); SEQ ID NO: 56 and SEQ ID NO: 50 (BC137-2 DS54); SEQ ID NO: 59 and SEQ ID NO: 60 (BC163); SEQ ID NO: 74 and SEQ ID NO: 82 (rehumanized P35H1L1); SEQ ID NO: 75 and SEQ ID NO: 82 (rehumanized P35H2L1); SEQ ID NO: 76 and SEQ ID NO: 82 (rehumanized P35H3L1); SEQ ID NO: 77 and SEQ ID NO: 82 (rehumanized P35H4L1); SEQ ID NO: 78 and SEQ ID NO: 82 (rehumanized P35H5L1); SEQ ID NO: 79 and SEQ ID NO: 82 (rehumanized P35H6L1); SEQ ID NO: 80 and SEQ ID NO: 82 (rehumanized P35H7L1); SEQ ID NO: 81 and SEQ ID NO: 82 (rehumanized P35H8L1); SEQ ID NO: 74 and SEQ ID NO: 83 (rehumanized P35H1L2); SEQ ID NO: 75 and SEQ ID NO: 83 (rehumanized P35H2L2); SEQ ID NO: 76 and SEQ ID NO: 83 (rehumanized P35H3L2); SEQ ID NO: 77 and SEQ ID NO: 83 (rehumanized P35H4L2); SEQ ID NO: 78 and SEQ ID NO: 83 (rehumanized P35H5L2); SEQ ID NO: 79 and SEQ ID NO: 83 (rehumanized P35H6L2); SEQ ID NO: 80 and SEQ ID NO: 83 (rehumanized P35H7L2); SEQ ID NO: 81 and SEQ ID NO: 83 (rehumanized P35H8L2); SEQ ID NO: 74 and SEQ ID NO: 84 (rehumanized P35H1L3); SEQ ID NO: 75 and SEQ ID NO: 84 (rehumanized P35H2L3); SEQ ID NO: 76 and SEQ ID NO: 84 (rehumanized P35H3L3); SEQ ID NO: 77 and SEQ ID NO: 84 (rehumanized P35H4L3); SEQ ID NO: 78 and SEQ ID NO: 84 (rehumanized P35H5L3); SEQ ID NO: 79 and SEQ ID NO: 84 (rehumanized P35H6L3); SEQ ID NO: 80 and SEQ ID NO: 84 (rehumanized P35H7L3); and SEQ ID NO: 81 and SEQ ID NO: 84 (rehumanized P35H8L3), respectively, wherein the antibody specifically binds to polySia.

In some embodiments, the polySia associated cancer is small cell or non-small cell lung cancer, neuroblastoma, pancreatic cancer, pituitary tumors, Wilm's tumor, rhabdomyosarcoma, glioblastoma, breast cancer, or acute myeloid leukemia. The polySia associated cancer may be a metastatic cancer.

Additionally or alternatively, in some embodiments of the method, the antibody is administered to the subject separately, sequentially or simultaneously with an additional therapeutic agent. Examples of additional therapeutic agents include one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents.

In another aspect, the present disclosure provides a method for detecting a tumor in a subject in vivo comprising (a) administering to the subject an effective amount of an antibody of the present technology, wherein the antibody is configured to localize to a tumor expressing high DP polySia and is labeled with a radioisotope; and (b) detecting the presence of a tumor in the subject by detecting radioactive levels emitted by the antibody that are higher than a reference value. In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, $^{188}$Re, $^{177}$Lu, and $^{67}$Cu. In some embodiments of the method, nonspecific FcR-dependent binding in normal tissues is eliminated or reduced (e.g., via N297A mutation in Fc region, which results in aglycosylation).

Also disclosed herein are kits for the detection and/or treatment of polySia associated cancers, comprising at least one immunoglobulin-related composition of the present technology (e.g., any antibody or antigen binding fragment described herein), or a functional variant (e.g., substitutional variant) thereof and instructions for use. In certain embodiments, the immunoglobulin-related composition is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to an anti-polySia immunoglobulin-related composition described herein. In some embodiments, the secondary antibody is coupled to at least one detectable label selected from the group consisting of a radioactive label, a fluorescent label, or a chromogenic label.

In one aspect, the present disclosure provides a method for detecting solid tumors in a subject in need thereof comprising (a) administering to the subject an effective amount of a complex comprising a radiolabeled DOTA hapten and a bispecific antibody of the present technology that binds to the radiolabeled DOTA hapten and a polySia antigen, wherein the complex is configured to localize to a solid tumor expressing the polySia antigen recognized by the bispecific antibody of the complex; and (b) detecting the presence of solid tumors in the subject by detecting radioactive levels emitted by the complex that are higher than a reference value.

In another aspect, the present disclosure provides a method for selecting a subject for pretargeted radioimmunotherapy comprising (a) administering to the subject an effective amount of a complex comprising a radiolabeled DOTA hapten and a bispecific antibody of the present technology that binds to the radiolabeled DOTA hapten and a polySia antigen, wherein the complex is configured to localize to a solid tumor expressing the polySia antigen recognized by the bispecific antibody of the complex; (b) detecting radioactive levels emitted by the complex; and (c) selecting the subject for pretargeted radioimmunotherapy when the radioactive levels emitted by the complex are higher than a reference value.

In one aspect, the present disclosure provides a method for increasing tumor sensitivity to radiation therapy in a subject diagnosed with a polySia-associated cancer comprising administering to the subject an effective amount of a complex comprising a radiolabeled-DOTA hapten and a bispecific antibody of the present technology that recognizes and binds to the radiolabeled-DOTA hapten and a polySia antigen target, wherein the complex is configured to localize to a tumor expressing the polySia antigen target recognized by the bispecific antibody of the complex.

In another aspect, the present disclosure provides a method for treating cancer in a subject in need thereof comprising administering to the subject an effective amount of a complex comprising a radiolabeled-DOTA hapten and a bispecific antibody of the present technology that recognizes and binds to the radiolabeled-DOTA hapten and a polySia antigen target, wherein the complex is configured to localize to a tumor expressing the polySia antigen target recognized by the bispecific antibody of the complex.

In any of the above embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments of the methods disclosed herein, the subject is human. Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter.

In one aspect, the present disclosure provides a method for increasing tumor sensitivity to radiation therapy in a subject diagnosed with a polySia-associated cancer comprising (a) administering an effective amount of an anti-DOTA bispecific antibody of the present technology to the subject, wherein the anti-DOTA bispecific antibody is configured to localize to a tumor expressing a polySia antigen target; and (b) administering an effective amount of a radiolabeled-DOTA hapten to the subject, wherein the radiolabeled-DOTA hapten is configured to bind to the anti-DOTA bispecific antibody. In another aspect, the present disclosure provides a method for treating cancer in a subject in need thereof comprising (a) administering an effective amount of an anti-DOTA bispecific antibody of the present technology to the subject, wherein the anti-DOTA bispecific antibody is configured to localize to a tumor expressing a polySia antigen target; and (b) administering an effective amount of a radiolabeled-DOTA hapten to the subject, wherein the radiolabeled-DOTA hapten is configured to bind to the anti-DOTA bispecific antibody. In some embodiments, the methods of the present technology further comprise administering an effective amount of a clearing agent to the subject prior to administration of the radiolabeled-DOTA hapten.

Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter. In any of the above embodiments of the methods disclosed herein, the subject is human.

BRIEF DESCRIPTION OF THE DRAWINGS

FIGS. 1(A) and 1(B) show the expression of polysialic acid on multiple cancer cell lines.

FIG. 2 shows the immunohistochemistry results of small cell lung cancer (SCLC) patient derived xenografts stained with chimeric P35 antibody.

FIG. 8(A) shows the binding kinetics of affinity matured clones based on rational design or yeast display affinity maturation using a direct screening method. FIG. 8(B) shows the positions of the amino acid changes in the affinity matured clones.

FIG. 9(A) shows the binding kinetics of affinity matured clones based on rational design or yeast display affinity maturation using a kinetic screening method. FIG. 9(B) shows the positions of the amino acid changes in the affinity matured clones.

FIGS. 14(A) and 14(B) show the human germline content of humanized clones.

FIGS. 15(A) and 15(B) show the amino acid sequences of the heavy chain and the light chain of the chimeric P35-IgG1 antibody, which correspond to SEQ ID NO: 23 and SEQ ID NO: 24, respectively. The CDR sequences are underlined.

FIG. 16(A) shows the amino acid and nucleotide sequences of a humanized P35 heavy chain, H1, corresponding to SEQ ID NO: 25 and SEQ ID NO: 92, respectively. FIG. 16(B) shows the amino acid and nucleotide sequences of a humanized P35 heavy chain, H2, corresponding to SEQ ID NO: 26 and SEQ ID NO: 93, respectively. The CDR sequences are underlined.

FIG. 17(A) shows the amino acid and nucleotide sequences of a humanized P35 light chains, L1, corresponding to SEQ ID NO: 27 and SEQ ID NO: 94, respectively. FIG. 17(B) shows the amino acid and nucleotide sequences of a humanized P35 light chain, L2, corresponding to SEQ ID NO: 28 and SEQ ID NO: 95, respectively. The CDR sequences are underlined.

FIGS. 18(A) and 18(B) show the amino acid sequences of the heavy chain and the light chain of the humanized P35 H1L2 IgG1 antibody, which correspond to SEQ ID NO: 25 and SEQ ID NO: 28, respectively. The CDR sequences are underlined.

FIG. 19 shows the amino acid sequence of the heavy chain of a rationally designed affinity-matured clone of humanized P35 heavy chain with a D31R mutation. The amino acid sequence corresponds to SEQ ID NO: 29. The CDR sequences are underlined. Modified residues in the variable domain are shown in bold.

FIG. 20 shows the amino acid sequence of the heavy chain variable domain of DS45, an affinity-matured clone of humanized P35 H1L2. The amino acid sequence corresponds to SEQ ID NO: 30. The CDR sequences are underlined. Modified residues in the variable domain are shown in bold.

FIG. 21 shows the amino acid sequence of the heavy chain variable domain of DS47, an affinity-matured clone of humanized P35 H1L2. The amino acid sequence corresponds to SEQ ID NO: 31. The CDR sequences are underlined. Modified residues in the variable domain are shown in bold.

FIG. 22 shows the amino acid sequence of the heavy chain variable domain of DS51, an affinity-matured clone of humanized P35 H1L2. The amino acid sequence corresponds to SEQ ID NO: 32. The CDR sequences are underlined. Modified residues in the variable domain are shown in bold.

FIG. 23 shows the amino acid sequence of the heavy chain variable domain of DS53, an affinity-matured clone of humanized P35 H1L2. The amino acid sequence corresponds to SEQ ID NO: 33. The CDR sequences are underlined. Modified residues in the variable domain are shown in bold.

FIG. 24 shows the amino acid sequence of the heavy chain variable domain of DS54, an affinity-matured clone of humanized P35 H1L2. The amino acid sequence corresponds to SEQ ID NO: 34. The CDR sequences are underlined. Modified residues in the variable domain are shown in bold. The CDR sequences are underlined. Modified residues in the variable domain are shown in bold.

FIG. 25 shows the amino acid sequence of the heavy chain variable domain of DS55, an affinity-matured clone of humanized P35 H1L2. The amino acid sequence corresponds to SEQ ID NO: 35. The CDR sequences are underlined. Modified residues in the variable domain are shown in bold.

FIGS. 26(A) and 26(B) show the amino acid sequences of the heavy chain and light chain variable domains of KS2, an affinity-matured clone of humanized P35 H1L2. The amino acid sequences correspond to SEQ ID NO: 36 and SEQ ID NO: 37, respectively. The CDR sequences are underlined. Modified residues in the variable domain are shown in bold.

FIGS. 27(A) and 27(B) show the amino acid sequences of the heavy chain and light chain variable domains of KS10, an affinity-matured clone of humanized P35 H1L2. The amino acid sequences correspond to SEQ ID NO: 38 and SEQ ID NO: 39, respectively.

FIGS. 28(A) and 28(B) show the amino acid sequences of the heavy chain and light chain variable domains of KS21, an affinity-matured clone of humanized P35 H1L2. The amino acid sequences correspond to SEQ ID NO: 40 and SEQ ID NO: 41, respectively. The CDR sequences are underlined. Modified residues in the variable domain are shown in bold.

FIGS. 29(A) and 29(B) show the amino acid sequences of the heavy chain and light chain variable domains of KS23, an affinity-matured clone of humanized P35 H1L2. The amino acid sequences correspond to SEQ ID NO: 42 and SEQ ID NO: 43, respectively. The CDR sequences are underlined. Modified residues in the variable domain are shown in bold.

FIG. 30 shows the amino acid sequences of the light chain variable domain of KS26, an affinity-matured clone of humanized P35 H1L2. The amino acid sequence corresponds to SEQ ID NO: 44.

FIG. 31 shows the amino acid sequences of the light chain variable domain of KS30, an affinity-matured clone of humanized P35 H1L2. The amino acid sequence corresponds to SEQ ID NO: 45. The CDR sequences are underlined. Modified residues in the variable domain are shown in bold.

FIGS. 32(A) and 32(B) show the amino acid sequences of the heavy chain and light chain variable domains of KS34, an affinity-matured clone of humanized P35 H1L2. The amino acid sequences correspond to SEQ ID NO: 46 and SEQ ID NO: 47, respectively. The CDR sequences are underlined. Modified residues in the variable domain are shown in bold.

FIGS. 33(A) and 33(B) show the amino acid and nucleotide sequences of the heavy chain of a polySiaxCD3 bispecific antibody, BC137, corresponding to SEQ ID NO: 48 and SEQ ID NO: 96, respectively. N297A and K322A substitutions in the Fc domain are shown in bold. FIGS. 33(C) and 33(D) shows the amino acid and nucleotide sequences of the light chain of BC137, corresponding to SEQ ID NO: 49 and SEQ ID NO: 97, respectively. The CDR sequences and the GS linker sequences are underlined.

FIGS. 34(A) and 34(B) shows the amino acid and nucleotide sequences of a modified light chain (BC137-2 light chain) for use in a polySiaxCD3 bispecific antibody, corresponding to SEQ ID NO: 50 and SEQ ID NO: 98, respectively. The sequence has been modified to make two Cys to Gly substitutions in the anti-CD3 huOKT3 scFv portion to alter the disulfide stabilization. The CDR sequences and the GS linker sequences are underlined. The modified Cys residues are shown in bold.

FIGS. 35(A) and 35(B) show the amino acid and nucleotide sequences of the heavy chain of the affinity-matured clone KS2 in the polySiaxCD3 BsAb format, corresponding to SEQ ID NO: 51 and SEQ ID NO: 99, respectively. Modified residues in the variable domain and the N297A and K322A substitutions in the Fc domain are shown in bold. FIGS. 35(C) and 35(D) show the amino acid and nucleotide sequences of the light chain, corresponding to SEQ ID NO: 52 and SEQ ID NO: 100, respectively. The CDR sequences and the GS linker sequences are underlined.

FIGS. 36A and 36(B) show the amino acid and nucleotide sequences of the heavy chain of the affinity-matured clone KS34 in the polySiaxCD3 BsAb format, corresponding to SEQ ID NO: 53 and SEQ ID NO: 101, respectively. Modified residues in the variable domain and the N297A and K322A substitutions in the Fc domain are shown in bold. FIGS. 36(C) and 36(D) show the amino acid and nucleotide sequences of the light chain, corresponding to SEQ ID NO: 54 and SEQ ID NO: 102, respectively. The underlined sequences correspond to GS linker sequences. The CDR sequences and the GS linker sequences are underlined.

FIGS. 37(A) and 37(B) show the amino acid and nucleotide sequences of the heavy chain of the affinity-matured clone DS47 in the polySiaxCD3 BsAb format, corresponding to SEQ ID NO: 55 and SEQ ID NO: 103, respectively. The CDR sequences are underlined. Modified residues in the variable domain and the N297A and K322A substitutions in the Fc domain are shown in bold.

FIGS. 38(A) and 38(B) show the amino acid and nucleotide sequences of the heavy chain of the affinity-matured clone DS54 in the polySiaxCD3 BsAb format, corresponding to SEQ ID NO: 56 and SEQ ID NO: 104, respectively. The CDR sequences are underlined. Modified residues in the variable domain and the N297A and K322A substitutions in the Fc domain are shown in bold.

FIGS. 39(A) and 39(B) show the amino acid and nucleotide sequences of the heavy chain of the affinity-matured clone DS47 with a D31R mutation in the polySiaxCD3 BsAb format, corresponding to SEQ ID NO: 57 and SEQ ID NO: 105, respectively. The CDR sequences are underlined. Modified residues in the variable domain and the N297A and K322A substitutions in the Fc domain are shown in bold.

FIGS. 40(A) and 40(B) show the amino acid and nucleotide sequences of the heavy chain of the affinity-matured clone DS54 with a D31R mutation in the polySiaxCD3 BsAb format, corresponding to SEQ ID NO: 58 and SEQ ID NO: 106, respectively. The CDR sequences are underlined. Modified residues in the variable domain and the N297A and K322A substitutions in the Fc domain are shown in bold.

FIGS. 41(A) and 41(B) show the amino acid and nucleotide sequences of the heavy chain of BC163, a polySiax DOTA bispecific antibody, corresponding to SEQ ID NO: 59 and SEQ ID NO: 107, respectively. Modified residues in the variable domain and the N297A and K322A substitutions in the Fc domain are shown in bold. FIGS. 41(C) and 41(D) show the amino acid and nucleotide sequences of the light chain, corresponding to SEQ ID NO: 60 and SEQ ID NO: 108, respectively. The CDR sequences and the GS linker sequences are underlined.

FIG. 42 shows the amino acid sequence of the affinity matured clone DS45 in the scFv format, corresponding to SEQ ID NO: 61. The underlined sequences correspond to GS linker sequences. The CDR sequences and the GS linker sequences are underlined. Modified residues in the variable domain are shown in bold.

FIG. 43 shows the amino acid sequence of the affinity matured clone DS47 in the scFv format, corresponding to SEQ ID NO: 62. The underlined sequences correspond to GS linker sequences. The CDR sequences and the GS linker sequences are underlined. Modified residues in the variable domain are shown in bold.

FIG. 44 shows the amino acid sequence of the affinity matured clone DS51 in the scFv format, corresponding to SEQ ID NO: 63. The underlined sequences correspond to GS linker sequences. The CDR sequences and the GS linker sequences are underlined. Modified residues in the variable domain are shown in bold.

FIG. 45 shows the amino acid sequence of the affinity matured clone DS53 in the scFv format, corresponding to SEQ ID NO: 64. The underlined sequences correspond to GS linker sequences. The CDR sequences and the GS linker sequences are underlined. Modified residues in the variable domain are shown in bold.

FIG. 46 shows the amino acid sequence of the affinity matured clone DS54 in the scFv format, corresponding to SEQ ID NO: 65. The underlined sequences correspond to GS linker sequences. The CDR sequences and the GS linker sequences are underlined. Modified residues in the variable domain are shown in bold.

FIG. 47 shows the amino acid sequence of the affinity matured clone DS55 in the scFv format, corresponding to SEQ ID NO: 66. The underlined sequences correspond to GS linker sequences. The CDR sequences and the GS linker sequences are underlined. Modified residues in the variable domain are shown in bold.

FIG. 48 shows the amino acid sequence of the affinity matured clone KS2 in the scFv format, corresponding to SEQ ID NO: 67. The underlined sequences correspond to GS linker sequences.

FIG. 49 shows the amino acid sequence of the affinity matured clone KS10 in the scFv format, corresponding to SEQ ID NO: 68. The CDR sequences and the GS linker sequences are underlined. Modified residues in the variable domain are shown in bold.

FIG. 50 shows the amino acid sequence of the affinity matured clone KS21 in the scFv format, corresponding to SEQ ID NO: 69. The underlined sequences correspond to GS linker sequences. The CDR sequences and the GS linker sequences are underlined. Modified residues in the variable domain are shown in bold.

FIG. 51 shows the amino acid sequence of the affinity matured clone KS23 in the scFv format, corresponding to SEQ ID NO: 70. The underlined sequences correspond to GS linker sequences.

FIG. 52 shows the amino acid sequence of the affinity matured clone KS26 in the scFv format, corresponding to SEQ ID NO: 71. The underlined sequences correspond to GS linker sequences. The CDR sequences and the GS linker sequences are underlined. Modified residues in the variable domain are shown in bold.

FIG. 53 shows the amino acid sequence of the affinity matured clone KS30 in the scFv format, corresponding to SEQ ID NO: 72. The underlined sequences correspond to GS linker sequences. The CDR sequences and the GS linker sequences are underlined. Modified residues in the variable domain are shown in bold.

FIG. 54 shows the amino acid sequence of the affinity matured clone KS34 in the scFv format, corresponding to SEQ ID NO: 73. The underlined sequences correspond to GS linker sequences. The CDR sequences and the GS linker sequences are underlined. Modified residues in the variable domain are shown in bold.

FIG. 55 shows the amino acid sequence of HC1, a re-humanized heavy chain based on P35 H1L2. The amino acid sequence corresponds to SEQ ID NO: 74. The CDR sequences are underlined.

FIG. 56 shows the amino acid sequence of HC2, a re-humanized heavy chain based on P35 H1L2. The amino acid sequence corresponds to SEQ ID NO: 75. The CDR sequences are underlined.

FIG. 57 shows the amino acid sequence of HC3, a re-humanized heavy chain based on P35 H1L2. The amino acid sequence corresponds to SEQ ID NO: 76. The CDR sequences are underlined.

FIG. 58 shows the amino acid sequence of HC4, a re-humanized heavy chain based on P35 H1L2 H1L2. The amino acid sequence corresponds to SEQ ID NO: 77. The CDR sequences are underlined.

FIG. 59 shows the amino acid sequence of HC5, a re-humanized heavy chain based on P35 H1L2. The amino acid sequence corresponds to SEQ ID NO: 78. The CDR sequences are underlined.

FIG. 60 shows the amino acid sequence of HC6, a re-humanized heavy chain based on P35 H1L2. The amino acid sequence corresponds to SEQ ID NO: 79. The CDR sequences are underlined.

FIG. 61 shows the amino acid sequence of HC7, a re-humanized heavy chain based on P35 H1L2. The amino acid sequence corresponds to SEQ ID NO: 80. The CDR sequences are underlined.

FIG. 62 shows the amino acid sequence of HC8, a re-humanized heavy chain based on P35 H1L2. The amino acid sequence corresponds to SEQ ID NO: 81. The CDR sequences are underlined.

FIG. 63 shows the amino acid sequence of LC1, a re-humanized light chain based on P35 H1L2. The amino acid sequence corresponds to SEQ ID NO: 82. The CDR sequences are underlined.

FIG. 64 shows the amino acid sequence of LC2, a re-humanized light chain based on P35 H1L2. The amino acid sequence corresponds to SEQ ID NO: 83. The CDR sequences are underlined.

FIG. 65 shows the amino acid sequence of LC3, a re-humanized light chain based on P35 H1L2. The amino acid sequence corresponds to SEQ ID NO: 84. The CDR sequences are underlined.

FIG. 68 shows a heatmap that compares the antigen binding properties and stability of the various re-humanized anti-polySia antibodies of the present technology relative to the chimeric HP35 polySia antibody. Column 1, MFI, based on binding to M14 melanoma cell line via flow cytometry at 1 μg per million cells, low binding (white) to high binding (dark gray). Column 2, Binding affinity, according to $K_D$ (M) obtained from binding to colominic acid via Surface plasmon resonance, low affinity (white) to high affinity (dark gray). Column 3, stability, based on purity after incubation at 37° C. for three weeks with HPCL, low purity (white) to high purity (dark gray). Clone LC2+HC5 was chosen for further characterization in vitro and in vivo due to high binding affinity to its antigen.

DETAILED DESCRIPTION

Figure 3:
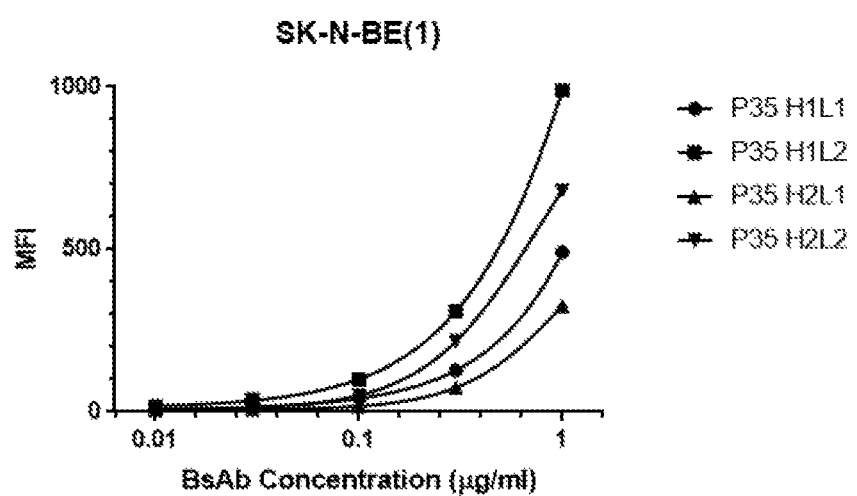
FIG. 3 shows the relative staining of neuroblastoma cell line SK-N-BE(1) using four humanized anti-polySia IgG1 antibodies.

It is to be appreciated that certain aspects, modes, embodiments, variations and features of the present methods are described below in various levels of detail in order to provide a substantial understanding of the present technology.

The present disclosure generally provides immunoglobulin-related compositions (e.g., antibodies or antigen binding fragments thereof), which can specifically bind to and neutralize the biological activity of polySia, and in particular, high DP polySia. The immunoglobulin-related compositions of the present technology are useful in methods for detecting or treating polySia associated cancers in a subject in need thereof. Accordingly, the various aspects of the present methods relate to the preparation, characterization, and manipulation of anti-polySia antibodies. The immunoglobulin-related compositions of the present technology are useful alone or in combination with additional therapeutic agents for treating cancer. In some embodiments, the immunoglobulin-related composition is a humanized antibody, a chimeric antibody, or a bispecific antibody.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1:*

*A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, $3^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds polySia will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multispecific antibodies, bispecific antibodies, etc.) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods include, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', F(ab')$_2$, and Fv fragments; diabodies; linear antibodies; single-chain antibody molecules; and multispecific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, a "clearing agent" is an agent that binds to excess bispecific antibody that is present in the blood compartment of a subject to facilitate rapid clearance via kidneys. The use of the clearing agent prior to hapten administration (e.g., DOTA) facilitates better tumor-to-background ratios in pre-targeted radioimmunotherapy (PRIT) systems. Examples of clearing agents include 500 kD-dextran-DOTA-Bn(Y) (Orcutt et al., *Mol Cancer Ther.* 11(6): 1365-1372 (2012)), 500 kD aminodextran-DOTA conjugate, antibodies against the pretargeting antibody, etc.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and 30 Hollinger et al., *Proc. Natl. Acad. Sci. USA,* 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ (scFv)). Bird et al. (1988) *Science* 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and neutralization activity in the same manner as are intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a carbohydrate (e.g., a polySia species). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFvFc, Fab, Fab' and F(ab')$_2$, but are not limited thereto.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a breast, lung, pancreas, adrenal gland, brain, kidney, nerve, or muscle tissue sample obtained by needle biopsy. Surgical biopsy samples may be derived from fresh samples or frozen samples obtained at the time of surgery, patient-derived xenografts, or cell lines established for surgical specimens.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 0125, 023; Better et al., *Science* 240: 1041-1043, 1988; Liu et al., *Proc. Natl. Acad. Sci. USA* 84: 3439-3443, 1987; Liu et al., *J. Immunol* 139: 3521-3526, 1987; Sun et al., *Proc. Natl. Acad. Sci. USA* 84: 214-218, 1987; Nishimura et al., *Cancer Res* 47: 999-1005, 1987; Wood et al., Nature 314: 446-449, 1885; and Shaw et al., *J. Natl. Cancer Inst.* 80: 1553-1559, 1988.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" of the polySia is a conformational epitope specifically adopted by a high DP polySia (e.g., DP>10, DP>20, DP>50, DP>100, or DP>200) to which the anti-polySia antibodies of the present technology specifically bind. To screen for anti-polySia antibodies which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if an anti-polySia antibody binds the same site or epitope as an anti-polySia antibody of the present technology. Alternatively, or additionally, epitope mapping can be performed by methods known in the art. For example, the antibody sequence can be mutagenized such as by alanine scanning, to identify contact residues. In a different method, polySia species with different DPs can be used in competition assays with the test antibodies or with a test antibody and an antibody with a characterized or known epitope specificity.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321: 522-525 (1986); Reichmann et al., *Nature* 332:323-329 (1988); and Presta, *Curr. Op. Struct. Biol.* 2:593-596 (1992). See e.g., Ahmed & Cheung, *FEBS Letters* 588(2):288-297 (2014).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, MD. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region) as measured using a BLAST or BLAST 2.0 sequence comparison algorithms with default parameters described below, or by manual alignment and visual inspection, e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816, 567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, "PRIT" or "pretargeted radioimmunotherapy" refers to a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a small hapten. A pre-targeting bispecific antibody, which has binding sites for the hapten as well as a target antigen, is administered first. Unbound antibody is then allowed to clear from circulation and the hapten is subsequently administered.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a carbohydrate antigen or an epitope on a carbohydrate antigen), as used herein, can be exhibited, for example, by a molecule having a $K_D$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term "specifically binds" may also refer to binding where a molecule (e.g., an antibody or antigen binding fragment thereof) binds to a particular antigen (e.g., a high DP polySia), without substantially binding to any other antigen or form of antigen (e.g., a low DP polySia).

As used herein, the term "simultaneous" therapeutic use refers to the administration of at least two active ingredients by the same route and at the same time or at substantially the same time.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-polySia antibodies described herein are contemplated. For example, it may be desirable to improve the binding affinity and/or other biological properties of the antibody. Amino acid sequence variants of an anti-polySia antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

TABLE 1

Amino Acid Substitutions

| Original Residue | Exemplary Substitutions | Conservative Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

Polysialic Acids

Sialic acids on their own can also be found linked together in long chains of up to 200 residues, known as polysialic acid (polySia), which are linked via α2-8-linkages and are found mainly on outer chains of N-linked oligosaccharides of neural cell adhesion molecule (NCAM) as well as other proteins (Finne, J., et al. *Biochem Biophys Res Commun* 112, 482-487 (1983)). NCAM is expressed on cells of neuroectodermal origin and plays a role in neural tissue development and regenerations (Sadoul, R., et al. *Nature* 304, 347-349 (1983)). PolySia regulates the homophilic interactions between NCAM molecules and heterophilic interactions with other adhesion molecules (Schreiber, S. C., et al. *Gastroenterology* 134, 1555-1566 (2008)). The biological properties of polySia depend on the degree of polymerization (DP), which is high in embryonic development but low in adult tissues (Rutishauser, U. *Nat Rev Neurosci* 9, 26-35 (2008)). High DP polySia shows an inhibitory effect on cellular adhesion (Muhlenhoff, M., et al. *Curr Opin Struct Biol* 8, 558-564 (1998); Johnson, C. P., et al. *J Biol Chem* 280, 137-145 (2005)), and is expressed on several metastatic cancers including small cell and non-small cell lung cancer, neuroblastoma, pancreatic cancer, pituitary tumors, Wilm's tumor, rhabdomyosarcoma (Falconer, R. A., et al. *Curr Cancer Drug Targets* 12, 925-939 (2012)), glioblastoma, (Amoureux, M. C., et al. *BMC Cancer* 10, 91 (2010)) and in breast cancer (Wang, X., et al. *Int J Mol Med* 37, 197-206 (2016)). The DP of polySia was greater than 55 Sia units in neuroblastoma (Livingston, B. D., et al. *J Biol Chem* 263, 9443-9448 (1988)). With its wide expression on several tumors types and virtual absence in most adult tissues, polySia is a target for cancer immunotherapy.

Several monoclonal antibodies have been developed against mono- and di-sialic acid (1-2 Sia units), oligo-sialic acid (3-5 units of Sia) and polySia (at least 8 Sia units). See Sato, C., and Kitajima, K. *J Biochem* 154, 115-136 (2013). Of these only murine mAb735 (Bitter-Suermann, D., and Roth, *J. Immunol Res* 6, 225-237 (1987)) has been described to have the highest specificity for high DP of PolySia, requiring at least 11 Sia units (Sato, C., and Kitajima, K. *J Biochem* 154, 115-136 (2013)). Further investigation into the binding kinetics of mAb735 showed high affinity (sub-nanomolar dissociation constant $K_D$) to polySia with a high DP (~200 Sia units), and progressively weaker affinity to lower degrees of polymerization (Hayrinen, J., et al. *Mol Immunol* 39, 399-411 (2002)).

Immunoglobulin-Related Compositions of the Present Technology

The present technology describes methods and compositions for the generation and use of anti-polySia immunoglobulin-related compositions (e.g., anti-polySia antibodies or antigen binding fragments thereof). The anti-polySia immunoglobulin-related compositions of the present disclosure may be useful in the diagnosis, or treatment of polySia-associated cancers. Anti-polySia immunoglobulin-related compositions within the scope of the present technology include, e.g., but are not limited to, monoclonal, chimeric, humanized, and diabodies that specifically bind polySia, a homolog, derivative or a fragment thereof. Anti-polySia immunoglobulin-related compositions within the scope of the present technology also include compositions in a bispecific antibody format for enhanced anti-tumor potency (e.g., via T cell recruitment or payload delivery). The present disclosure also provides antigen binding fragments of any of the anti-polySia antibodies disclosed herein, wherein the antigen binding fragment is selected from the group consisting of Fab, F(ab)'2, Fab', scF$_v$, and F$_v$. The amino acid sequences of the CDR regions of the immunoglobulin-related compositions disclosed herein are defined according to the Kabat system.

In one aspect, the present technology provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence selected from the group consisting of: DYYIH (SEQ ID NO: 1), RYYIH (SEQ ID NO: 7), GYYIH (SEQ ID NO: 8), and NYYIH (SEQ ID NO: 9), a $V_H$-CDR2 sequence selected from the group consisting of: WIYPGSGNTKYNEKFKG (SEQ ID NO: 2), SIYPGSGNTKYNEKFKG (SEQ ID NO: 10), RIYPGSGNTKYNEKFKG (SEQ ID NO: 11), CIYPGSGNTKYNEKFKG (SEQ ID NO: 12), WIYPGSGNTKYNEKFEG (SEQ ID NO: 13), WIYPGSGNTKYNQKFQG (SEQ ID NO: 14), WIYPGSGNTKYSQKFQG (SEQ ID NO: 15), WIYPGSGNTKYSEKFQG (SEQ ID NO: 16), and WIYPGSGNTKYSQKFKG (SEQ ID NO: 18) and a $V_H$-CDR3 sequence of GGKFAMDY (SEQ ID NO:3); and/or (b) the $V_L$ comprises a $V_L$-CDR1 sequence selected from the group consisting of: RSSQSLVHSNGNTYLY (SEQ ID NO: 4) and RSSQSLVHSNGKTYLY (SEQ ID NO: 20), a $V_L$-CDR2 sequence of RVSNRFS (SEQ ID NO: 5), and a $V_L$-CDR3 sequence selected from the group consisting of: FQGTHVPYT (SEQ ID NO: 6), FQGTHVPYI (SEQ ID NO: 21), and FQGTHEPYT (SEQ ID NO: 22).

In some embodiments, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence of SEQ ID NO: 1, a $V_H$-CDR2 sequence of SEQ ID NO: 2, a $V_H$-CDR3 sequence of SEQ ID NO: 3; and/or (b) the $V_L$ comprises a $V_L$-CDR1 sequence, a $V_L$-CDR2 sequence, and a $V_L$-CDR3 sequence selected from the group consisting of: SEQ ID NO: 4, SEQ ID NO: 5, and SEQ ID NO: 6; SEQ ID NO: 20, SEQ ID NO: 5, and SEQ ID NO: 6; SEQ ID NO: 4, SEQ ID NO: 5, and SEQ ID NO: 22.

In some embodiments, the present disclosure provides an antibody or antigen binding fragment thereof comprising a light chain immunoglobulin variable domain ($V_L$) and a heavy chain immunoglobulin variable domain ($V_H$), wherein (a) the $V_L$ comprises a $V_L$-CDR1 sequence of SEQ ID NO: 4, a $V_L$-CDR2 sequence of SEQ ID NO: 5, a $V_L$-CDR3 sequence of SEQ ID NO: 6; and/or (b) the $V_H$ comprises a $V_H$-CDR1 sequence, a $V_H$-CDR2 sequence, and a $V_H$-CDR3 sequence selected from the group consisting of: SEQ ID NO: 1, SEQ ID NO: 2, SEQ ID NO: 3; SEQ ID NO: 1, SEQ ID NO: 11, and SEQ ID NO: 3; SEQ ID NO: 1, SEQ ID NO: 12, SEQ ID NO: 3; SEQ ID NO: 1, SEQ ID NO: 13, and SEQ ID NO: 3; SEQ ID NO: 7, SEQ ID NO: 2, and SEQ ID NO: 3; SEQ ID NO: 7, SEQ ID NO: 11, and SEQ ID NO: 3; SEQ ID NO: 8, SEQ ID NO: 10, and SEQ ID NO: 3; SEQ ID NO: 8, SEQ ID NO: 12, and SEQ ID NO: 3; SEQ ID NO: 9, SEQ ID NO: 11, and SEQ ID NO: 3; SEQ ID NO: 9, SEQ ID NO: 12, and SEQ ID NO: 3; SEQ ID NO: 1, SEQ ID NO: 14, and SEQ ID NO: 3; SEQ ID NO: 1, SEQ ID NO: 15, and SEQ ID NO: 3; SEQ ID NO: 1, SEQ ID NO: 16, and SEQ ID NO: 3; and SEQ ID NO: 1, SEQ ID NO: 18, and SEQ ID NO: 3.

In some embodiments, the present disclosure provides an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence, a $V_H$-CDR2 sequence, and a $V_H$-CDR1 sequence, and the $V_L$ comprises a $V_L$-CDR1 sequence, a $V_L$-CDR2 sequence, and a $V_L$-CDR3 sequence, selected from the group consisting of: a) SEQ ID NOS: 1, 2, 3, 4, 5, and 6, respectively; b) SEQ ID NOS: 1, 2, 3, 4, 5, and 22, respectively; c) SEQ ID NOS: 1, 2, 3, 20, 5, and 6, respectively; d) SEQ ID NOS: 1, 11, 3, 4, 5, and 6, respectively; e) SEQ ID NOS: 1, 12, 3, 4, 5, and 6, respectively; f) SEQ ID NOS: 1, 13, 3, 4, 5, and 6, respectively; g) SEQ ID NOS: 1, 13, 3, 4, 5, and 21, respectively; h) SEQ ID NOS: 7, 2, 3, 4, 5, and 6, respectively; i) 7, 11, 3, 4, 5, and 6, respectively; j) SEQ ID NOS: 8, 10, 3, 4, 5, and 6, respectively; k) 8, 12, 3, 4, 5, and 6, respectively; l) SEQ ID NOS: 9, 11, 3, 4, 5, and 6, respectively; and m) SEQ ID NOS: 9, 12, 3, 4, 5, and 6, respectively.

In some embodiments, the antibody further comprises a Fc domain of any isotype, e.g., but are not limited to, IgG (including IgG1, IgG2, IgG3, and IgG4), IgA (including IgA$_1$ and IgA$_2$), IgD, IgE, or IgM, and IgY. Non-limiting examples of constant region sequences include:

Human IgD constant region, Uniprot: P01880
(SEQ ID NO: 85)
APTKAPDVFPIISGCRHPKDNSPVVLACLITGYHPTSVTVTWYMGTQSQP
QRTFPEIQRRDSYYMTSSQLSTPLQQWRQGEYKCVVQHTASKSKKEIFRW
PESPKAQASSVPTAQPQAEGSLAKATTAPATTRNTGRGGEEKKKEKEKEE
QEERETKTPECPSHTQPLGVYLLTPAVQDLWLRDKATFTCFVVGSDLKDA
HLTWEVAGKVPTGGVEEGLLERHSNGSQSQHSRLTLPRSLWNAGTSVTCT
LNHPSLPPQRLMALREPAAQAPVKLSLNLLASSDPPEAASWLLCEVSGFS
PPNILLMWLEDQREVNTSGFAPARPPPQPGSTTFWAWSVLRVPAPPSPQP
ATYTCVVSHEDSRTLLNASRSLEVSYVTDHGPMK Human IgG1 constant region, Uniprot: P01857
(SEQ ID NO: 86)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK Human IgG2 constant region, Uniprot: P01859
(SEQ ID NO: 87)
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDISVEWESNGQPENNYKTTPPMLDSDGSFFLYSKLTVDKSRWQQGN
VFSCSVMHEALHNHYTQKSLSLSPGK Human IgG3 constant region, Uniprot: P01860
(SEQ ID NO: 88)
ASTKGPSVFPLAPCSRSTSGGTAALGCLVKDYFPEPVTVSWNSGALTSGV
HTFPAVLQSSGLYSLSSVVTVPSSSLGTQTYTCNVNHKPSNTKVDKRVEL
KTPLGDTTHTCPRCPEPKSCDTPPPCPRCPEPKSCDTPPPCPRCPEPKSC
DTPPPCPRCPAPELLGGPSVFLFPPKPKDTLMISRTPEVTCVVVDVSHED
PEVQFKWYVDGVEVHNAKTKPREEQYNSTFRVVSVLTVLHQDWLNGKEYK
CKVSNKALPAPIEKTISKTKGQPREPQVYTLPPSREEMTKNQVSLTCLVK
GFYPSDIAVEWESSGQPENNYNTTPPMLDSDGSFFLYSKLTVDKSRWQQG
NIFSCSVMHEALHNRFTQKSLSLSPGK Human IgM constant region, Uniprot: P01871
(SEQ ID NO: 89)
GSASAPTLFPLVSCENSPSDTSSVAVGCLAQDFLPDSITLSWKYKNNSDI
SSTRGFPSVLRGGKYAATSQVLLPSKDVMQGTDEHVVCKVQHPNGNKEKN
VPLPVIAELPPKVSVFVPPRDGFFGNPRKSKLICQATGFSPRQIQVSWLR
EGKQVGSGVTTDQVQAEAKESGPTTYKVTSTLTIKESDWLGQSMFTCRVD
HRGLTFQQNASSMCVPDQDTAIRVFAIPPSFASIFLTKSTKLTCLVTDLT
TYDSVTISWTRQNGEAVKTHTNISESHPNATFSAVGEASICEDDWNSGER
FTCTVTHTDLPSPLKQTISRPKGVALHRPDVYLLPPAREQLNLRESATIT
CLVTGFSPADVFVQWMQRGQPLSPEKYVTSAPMPEPQAPGRYFAHSILTV
SEEEWNTGETYTCVAHEALPNRVTERTVDKSTGKPTLYNVSLVMSDTAGT
CY Human IgG4 constant region, Uniprot: P01861
(SEQ ID NO: 90)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK Human IgA1 constant region, Uniprot: P01876
(SEQ ID NO: 91)
ASPTSPKVFPLSLCSTQPDGNVVIACLVQGFFPQEPLSVTWSESGQGVTA
RNFPPSQDASGDLYTTSSQLTLPATQCLAGKSVTCHVKHYTNPSQDVTVP
CPVPSTPPTPSPSTPPTPSPSCCHPRLSLHRPALEDLLLGSEANLTCTLT
GLRDASGVTFTWTPSSGKSAVQGPPERDLCGCYSVSSVLPGCAEPWNHGK
TFTCTAAYPESKTPLTATLSKSGNTFRPEVHLLPPPSEELALNELVTLTC
LARGFSPKDVLVRWLQGSQELPREKYLTWASRQEPSQGTTTFAVTSILRV
AAEDWKKGDTFSCMVGHEALPLAFTQKTIDRLAGKPTHVNVSVVMAEVDG
TCY Human IgA2 constant region, Uniprot: P01877
(SEQ ID NO: 17)
ASPTSPKVFPLSLDSTPQDGNVVVACLVQGFFPQEPLSVTWSESGQNVTA
RNFPPSQDASGDLYTTSSQLTLPATQCPDGKSVTCHVKHYTNPSQDVTVP
CPVPPPPCCHPRLSLHRPALEDLLLGSEANLTCTLTGLRDASGATFTWT
PSSGKSAVQGPPERDLCGCYSVSSVLPGCAQPWNHGETFTCTAAHPELKT
PLTANITKSGNTFRPEVHLLPPPSEELALNELVTLTCLARGFSPKDVLVR
WLQGSQELPREKYLTWASRQEPSQGTTTFAVTSILRVAAEDWKKGDTFSC
MVGHEALPLAFTQKTIDRMAGKPTHVNVSVVMAEVDGTCY Human Ig kappa constant region, Uniprot: P01834
(SEQ ID NO: 19)
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKS
FNRGEC In some embodiments, the immunoglobulin-related compositions of the present technology comprise a heavy chain constant region that is at least 80%, at least 85%, at least 90%, at least 95%, at least 99%, or is 100% identical to SEQ ID NOS: 17, or 85-91. Additionally or alternatively, in some embodiments, the immunoglobulin-related compositions of the present technology comprise a light chain constant region that is at least 80%, at least 85%, at least 90%, at least 95%, at least 99%, or is 100% identical to SEQ ID NO: 19. In some embodiments, the immunoglobulin-related compositions of the present technology bind to high DP polySia (e.g. a DP of about 10-20 Sia units, about 20-30 Sia units, about 30-50 Sia units, about 50-70 Sia units, about 70-100 Sia units, about 100-200 Sia units, or about 200-400 Sia units). In some embodiments, the antibody or antigen binding fragment binds to high DP polySia, e.g., with a DP>10, DP>20, DP>50, DP>100, or DP>200. In some embodiments, the epitope is a conformational epitope that is specific to high DP polySia. In some embodiments, the conformational epitope includes, 3 or more Sia units. In some embodiments, the 3 or more Sia units may be consecutive units.

In another aspect, the present disclosure provides an isolated immunoglobulin-related composition (e.g., an antibody or antigen binding fragment thereof) comprising a heavy chain (HC) amino acid sequence comprising SEQ ID NO: 23, SEQ ID NO: 25, SEQ ID NO: 26, SEQ ID NO: 29, SEQ ID NO: 48, SEQ ID NO: 51, SEQ ID NO: 53, SEQ ID NO: 55, SEQ ID NO: 56, SEQ ID NO: 57, SEQ ID NO: 58, SEQ ID NO: 59, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, or a variant thereof having one or more conservative amino acid substitutions.

Additionally or alternatively, in some embodiments, the immunoglobulin-related compositions of the present technology comprise a light chain (LC) amino acid sequence comprising SEQ ID NO: 24, SEQ ID NO: 27, SEQ ID NO: 28, SEQ ID NO: 49, SEQ ID NO: 50, SEQ ID NO: 52, SEQ ID NO: 54, SEQ ID NO: 60, SEQ ID NO: 82, SEQ ID NO: 83, SEQ ID NO: 84, or a variant thereof having one or more conservative amino acid substitutions.

In some embodiments, the immunoglobulin-related compositions of the present technology comprise a HC amino acid sequence and a LC amino acid sequence selected from the group consisting of: SEQ ID NO: 23 and SEQ ID NO: 24 (chimeric P35); SEQ ID NO: 25 and SEQ ID NO: 28 (humanized P35 H1L2); SEQ ID NO: 25 and SEQ ID NO: 27 (humanized P35 H1L1); SEQ ID NO: 26 and SEQ ID NO: 28 (humanized P35 H2L2); SEQ ID NO: 26 and SEQ ID NO: 27 (humanized P35 H2L1); SEQ ID NO: 48 and SEQ ID NO: 49 (BC137); SEQ ID NO: 51 and SEQ ID NO: 52 (BC137 KS2); SEQ ID NO: 53 and SEQ ID NO: 54 (BC137 KS34); SEQ ID NO: 55 and SEQ ID NO: 49 (BC137 DS47); SEQ ID NO: 56 and SEQ ID NO: 49 (BC137 DS54); SEQ ID NO: 57 and SEQ ID NO: 49 (BC137 DS47 D31R); SEQ ID NO: 58 and SEQ ID NO: 49 (BC137 DS54 D31R); SEQ ID NO: 55 and SEQ ID NO: 50 (BC137-2 DS47); SEQ ID NO: 56 and SEQ ID NO: 50 (BC137-2 DS54); SEQ ID NO: 59 and SEQ ID NO: 60 (BC163); SEQ ID NO: 74 and SEQ ID NO: 82 (rehumanized P35H1L1); SEQ ID NO: 75 and SEQ ID NO: 82 (rehumanized P35H2L1); SEQ ID NO: 76 and SEQ ID NO: 82 (rehumanized P35H3L1); SEQ ID NO: 77 and SEQ ID NO: 82 (rehumanized P35H4L1); SEQ ID NO: 78 and SEQ ID NO: 82 (rehumanized P35H5L1); SEQ ID NO: 79 and SEQ ID NO: 82 (rehumanized P35H6L1); SEQ ID NO: 80 and SEQ ID NO: 82 (rehumanized P35H7L1); SEQ ID NO: 81 and SEQ ID NO: 82 (rehumanized P35H8L1); SEQ ID NO: 74 and SEQ ID NO: 83 (rehumanized P35H1L2); SEQ ID NO: 75 and SEQ ID NO: 83 (rehumanized P35H2L2); SEQ ID NO: 76 and SEQ ID NO: 83 (rehumanized P35H3L2); SEQ ID NO: 77 and SEQ ID NO: 83 (rehumanized P35H4L2); SEQ ID NO: 78 and SEQ ID NO: 83 (rehumanized P35H5L2); SEQ ID NO: 79 and SEQ ID NO: 83 (rehumanized P35H6L2); SEQ ID NO: 80 and SEQ ID NO: 83 (rehumanized P35H7L2); SEQ ID NO: 81 and SEQ ID NO: 83 (rehumanized P35H8L2); SEQ ID NO: 74 and SEQ ID NO: 84 (rehumanized P35H1L3); SEQ ID NO: 75 and SEQ ID NO: 84 (rehumanized P35H2L3); SEQ ID NO: 76 and SEQ ID NO: 84 (rehumanized P35H3L3); SEQ ID NO: 77 and SEQ ID NO: 84 (rehumanized P35H4L3); SEQ ID NO: 78 and SEQ ID NO: 84 (rehumanized P35H5L3); SEQ ID NO: 79 and SEQ ID NO: 84 (rehumanized P35H6L3); SEQ ID NO: 80 and SEQ ID NO: 84 (rehumanized P35H7L3); and SEQ ID NO: 81 and SEQ ID NO: 84 (rehumanized P35H8L3), respectively.

In any of the above embodiments of the immunoglobulin-related compositions, the HC and LC immunoglobulin variable domain sequences form an antigen binding site that binds to high DP polySia (e.g. a DP of about 10-20 Sia units, about 20-30 Sia units, about 30-50 Sia units, about 50-70 Sia units, about 70-100 Sia units, about 100-200 Sia units, or about 200-400 Sia units). In some embodiments, the antibody or antigen binding fragment binds to high DP polySia, e.g., with a DP>10, DP>20, DP>50, DP>100, or DP>200. In some embodiments, the epitope is a conformational epitope that is specific to high DP polySia. In some embodiments, the conformational epitope includes, 3 or more Sia units. In some embodiments, the 3 or more Sia units may be consecutive units In some embodiments, the HC and LC immunoglobulin variable domain sequences are components of the same polypeptide chain. In other embodiments, the HC and LC immunoglobulin variable domain sequences are components of different polypeptide chains. In certain embodiments, the antibody is a full-length antibody.

In some embodiments, the immunoglobulin-related compositions of the present technology bind specifically to polySia. In some embodiments, the immunoglobulin-related compositions of the present technology bind high DP polySia with a dissociation constant ($K_D$) of about $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the immunoglobulin-related compositions are monoclonal antibodies, chimeric antibodies, humanized antibodies, or bispecific antibodies. In some embodiments, the antibodies comprise a human antibody framework region.

In certain embodiments, the immunoglobulin-related composition includes one or more of the following characteristics: (a) the light chain immunoglobulin variable domain sequence is at least 80%, at least 85%, at least 90%, at least 95%, or at least 99% identical to the light chain immunoglobulin variable domain sequence present in any one of SEQ ID NOs: 37, 39, 41, 43, 44, 45, 47, 24, 27, 28, 49, 50, 52, 54, 60, 82, 83, or 84; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 30, 31, 32, 33, 34, 35, 36, 38, 40, 42, 46, 23, 25, 26, 29, 48, 51, 53, 55, 56, 57, 58, 59, 74, 75, 76, 77, 78, 79, 80, or 81. In another aspect, one or more amino acid residues in the immunoglobulin-related compositions provided herein are substituted with another amino acid. The substitution may be a "conservative substitution" as defined herein.

In some embodiments, the immunoglobulin-related composition comprises a scFv having the amino acid sequence of any one of SEQ ID NOs: 61-73.

In some embodiments, the immunoglobulin-related composition comprises (a) a LC sequence that is at least 80%, at least 85%, at least 90%, at least 95%, or at least 99% identical to the LC sequence present in any one of SEQ ID NOs: 24, 27, 28, 49, 50, 52, 54, 60, 82, 83, or 84; and/or (b) a HC sequence that is at least 80%, at least 85%, at least 90%, at least 95%, or at least 99% identical to the HC sequence present in any one of SEQ ID NOs: 23, 25, 26, 29, 48, 51, 53, 55, 56, 57, 58, 59, 74, 75, 76, 77, 78, 79, 80, or 81.

In certain embodiments, the immunoglobulin-related compositions contain an IgG1 constant region comprising one or more amino acid substitutions selected from the group consisting of N297A and K322A. Additionally or alternatively, in some embodiments, the immunoglobulin-related compositions contain an IgG4 constant region comprising a S228P mutation.

Amino acid and nucleotide sequences of exemplary anti-polySia immunoglobulin-related compositions are shown, for example, in FIGS. 15-65.

In some aspects, the anti-polySia immunoglobulin-related compositions described herein contain structural modifications to facilitate rapid binding and cell uptake and/or slow release. In some aspects, the anti-polySia immunoglobulin-related composition of the present technology (e.g., an antibody) may contain a deletion in the CH2 constant heavy chain region to facilitate rapid binding and cell uptake and/or slow release. In some aspects, a Fab fragment is used to facilitate rapid binding and cell uptake and/or slow release. In some aspects, a F(ab)'$_2$ fragment is used to facilitate rapid binding and cell uptake and/or slow release.

In one aspect, the present technology provides a nucleic acid sequence encoding a heavy chain or a light chain of an immunoglobulin-related composition described herein. Also disclosed herein are recombinant nucleic acid sequences encoding any of the antibodies described herein. In some embodiments, the nucleic acid sequence is selected from the group consisting of SEQ ID NOs: 92-108. In another aspect, the present technology provides a host cell expressing any nucleic acid sequence encoding a heavy chain or a light chain of an immunoglobulin-related composition described herein.

The immunoglobulin-related compositions of the present technology (e.g., an anti-polySia antibody) can be monospecific, bispecific, trispecific or of greater multispecificity. Multispecific antibodies can be specific for polySia with different degrees of polymerization or can be specific for both polySia as well as for heterologous compositions, such as a heterologous polypeptide or solid support material. See, e.g., WO 93/17715; WO 92/08802; WO 91/00360; WO 92/05793; Tutt et al., J. Immunol. 147: 60-69 (1991); U.S. Pat. Nos. 5,573,920, 4,474,893, 5,601,819, 4,714,681, 4,925,648; 6,106,835; Kostelny et al., J. Immunol. 148: 1547-1553 (1992). In some embodiments, the immunoglobulin-related compositions are chimeric. In certain embodiments, the immunoglobulin-related compositions are humanized.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In any of the above embodiments of the immunoglobulin-related compositions of the present technology, the antibody or antigen binding fragment may be optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. For a chemical bond or physical bond, a functional group on the immunoglobulin-related composition typically associates with a functional group on the agent. Alternatively, a functional group on the agent associates with a functional group on the immunoglobulin-related composition.

The functional groups on the agent and immunoglobulin-related composition can associate directly. For example, a functional group (e.g., a sulfhydryl group) on an agent can associate with a functional group (e.g., sulfhydryl group) on an immunoglobulin-related composition to form a disulfide. Alternatively, the functional groups can associate through a cross-linking agent (i.e., linker). Some examples of cross-linking agents are described below. The cross-linker can be attached to either the agent or the immunoglobulin-related composition. The number of agents or immunoglobulin-related compositions in a conjugate is also limited by the number of functional groups present on the other. For example, the maximum number of agents associated with a conjugate depends on the number of functional groups present on the immunoglobulin-related composition. Alternatively, the maximum number of immunoglobulin-related compositions associated with an agent depends on the number of functional groups present on the agent.

In yet another embodiment, the conjugate comprises one immunoglobulin-related composition associated to one agent. In one embodiment, a conjugate comprises at least one agent chemically bonded (e.g., conjugated) to at least one immunoglobulin-related composition. The agent can be chemically bonded to an immunoglobulin-related composition by any method known to those in the art. For example, a functional group on the agent may be directly attached to a functional group on the immunoglobulin-related composition. Some examples of suitable functional groups include, for example, amino, carboxyl, sulfhydryl, maleimide, isocyanate, isothiocyanate and hydroxyl.

The agent may also be chemically bonded to the immunoglobulin-related composition by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985, 566; and 6,133,038 of Kreatech Biotechnology, B.V., Amsterdam, The Netherlands.

Alternatively, the functional group on the agent and immunoglobulin-related composition can be the same. Homobifunctional cross-linkers are typically used to cross-link identical functional groups. Examples of homobifunctional cross-linkers include EGS (i.e., ethylene glycol bis [succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the agent from the immunoglobulin-related composition. The web-site of Pierce Biotechnology, Inc. described above can also provide assistance to one skilled in the art in choosing suitable cross-linkers which can be cleaved by, for example, enzymes in the cell. Thus the agent can be separated from the immunoglobulin-related composition. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a conjugate comprises at least one agent physically bonded with at least one immunoglobulin-related composition. Any method known to those in the art can be employed to physically bond the agents with the immunoglobulin-related compositions. For example, the immunoglobulin-related compositions and agents can be mixed together by any method known to those in the art. The order of mixing is not important. For instance, agents can be physically mixed with immunoglobulin-related compositions by any method known to those in the art. For example, the immunoglobulin-related compositions and agents can be placed in a container and agitated, by for example, shaking the container, to mix the immunoglobulin-related compositions and agents.

The immunoglobulin-related compositions can be modified by any method known to those in the art. For instance, the immunoglobulin-related composition may be modified by means of cross-linking agents or functional groups, as described above.

A. Methods of Preparing Anti-polySia Antibodies of the Present Technology

General Overview. Initially, a target polySia species is chosen to which an antibody of the present technology can be raised. For example, an antibody may be raised against high DP polySia, e.g., with a DP>10, DP>20, DP>50, DP>100, or DP>200. Techniques for generating antibodies directed to such target antigens are well known to those skilled in the art. Examples of such techniques include, for example, but are not limited to, those involving display libraries, xeno or human mice, hybridomas, and the like. The preparation of antibodies specific for polySia is described herein.

It should be understood that recombinantly engineered antibodies and antibody fragments, e.g., antibody-related polypeptides, which are directed to polySia and are suitable for use in accordance with the present disclosure.

Anti-polySia antibodies that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli*.

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule Sequencing and Synthesis, Selected Methods and Applications*, pp. 127-149, 1998, Alan R. Liss, Inc.) so long as such a variant forms an operative antibody which recognizes polySia species. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens. Methods of generating antibodies or antibody fragments of the present technology typically include immunizing a subject (generally a non-human subject such as a mouse or rabbit) with a purified polySia target (e.g., high DP polySia, e.g., with a DP>10, DP>20, DP>50, DP>100, or DP>200) or with a polySia(+) cell line expressing high DP polySia. An appropriate immunogenic preparation can contain, e.g., a recombinantly-expressed polySia species or a chemically-synthesized polySia species.

If needed, the immunogenicity of the polySia target can be increased by fusion or conjugation to a hapten such as keyhole limpet hemocyanin (KLH) or ovalbumin (OVA). Many such haptens are known in the art. One can also combine the polySia target with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization") to a particular antigen, e.g., high DP polySia. In some embodiments, the immunization can occur as a result of vaccinating the individual with a vaccine containing the antigen. For example, the vaccine can be a polySia vaccine comprising one or more high DP polySia species. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD4^+$ T cells. A first exposure to an antigen primes the immune system and additional exposure(s) results in a DTH.

Following appropriate immunization, the anti-polySia antibody can be prepared from the subject's serum. If desired, the antibody molecules directed against the polySia target can be isolated from the mammal (e.g., from the blood) and further purified by well-known techniques, such as polypeptide A chromatography to obtain the IgG fraction.

Monoclonal Antibody. In one embodiment of the present technology, the antibody is an anti-polySia monoclonal antibody. For example, in some embodiments, the anti-polySia monoclonal antibody may be a human or a mouse anti-polySia monoclonal antibody. For preparation of monoclonal antibodies directed towards high DP polySia, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256: 495-497); the trioma technique; the human B-cell hybridoma technique (See, e.g., Kozbor, et al., 1983. *Immunol. Today* 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc. Natl. Acad. Sci. USA* 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for high DP polySia or derivatives, fragments, analogs or homologs thereof. Alternatively, hybridomas expressing anti-polySia monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., high DP polySia binding, can be used as expressed by the hybridoma, it can be bound to a molecule such as polyethylene glycol (PEG) to alter its properties, or a cDNA encoding it can be isolated, sequenced and manipulated in various ways. Other manipulations include substituting or deleting particular amino acyl residues that contribute to instability of the antibody during storage or after administration to a subject, and affinity maturation techniques to improve affinity of the anti-polySia antibody to high DP polySia.

Hybridoma Technique. In some embodiments, the antibody of the present technology is an anti-polySia monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, NY, 349 (1988); Hammerling et al., *Monoclonal Antibodies And T-Cell Hybridomas*, 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-polySia antibodies, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., *Science* 246: 1275-1281, 1989) to allow rapid and effective identification of monoclonal Fab fragments with the desired specificity for high DP polySia or derivatives, fragments, analogs or homologs thereof. Other examples of phage display methods that can be used to make the antibodies of the present technology include those disclosed in Huston et al., *Proc. Natl. Acad. Sci U.S.A.*, 85:

5879-5883, 1988; Chaudhary et al., *Proc. Natl. Acad. Sci U.S.A.,* 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-polySia Antibodies. As noted above, the antibodies of the present technology can be produced through the application of recombinant DNA technology. Recombinant polynucleotide constructs encoding an anti-polySia antibody of the present technology typically include an expression control sequence operably-linked to the coding sequences of anti-polySia antibody chains, including naturally-associated or heterologous promoter regions. As such, another aspect of the technology includes vectors containing one or more nucleic acid sequences encoding an anti-polySia antibody of the present technology. For recombinant expression of one or more of the polypeptides of the present technology, the nucleic acid containing all or a portion of the nucleotide sequence encoding the anti-polySia antibody is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-polySia antibody, and the collection and purification of the anti-polySia antibody, e.g., cross-reacting anti-polySia antibodies. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with polySia binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-polySia antibody), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-polySia antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-polySia antibody, etc.).

Another aspect of the present technology pertains to anti-polySia antibody-expressing host cells, which contain a nucleic acid encoding one or more anti-polySia antibodies. The recombinant expression vectors of the present technology can be designed for expression of an anti-polySia antibody in prokaryotic or eukaryotic cells. For example, an anti-polySia antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-polySia antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-polySia antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20: 2111-2118). Such alteration of nucleic acid sequences of the present technology can be carried out by standard DNA synthesis techniques.

In another embodiment, the anti-polySia antibody expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (Invitrogen Corp, San Diego, Calif.). Alternatively, an anti-polySia antibody can be expressed in insect cells using baculovirus expression vectors. Baculovirus vectors available for expression of polypeptides, e.g., anti-polySia antibody, in cultured insect cells (e.g., SF9 cells) include the pAc series (Smith, et al., *Mol. Cell. Biol.* 3: 2156-2165, 1983) and the pVL series (Lucklow and Summers, 1989. *Virology* 170: 31-39).

In yet another embodiment, a nucleic acid encoding an anti-polySia antibody of the present technology is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-polySia antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), promoters of T cell receptors (Winoto and Baltimore, *EMBO J.* 8: 729-733, 1989) and immunoglobulins (Banerji, et al., 1983. *Cell* 33: 729-740; Queen and Baltimore, *Cell* 33: 741-748, 1983), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-polySia antibody can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Illustrative expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-polySia antibody or can be introduced on a separate vector. Cells stably transfected with the introduced nucleic acid can be identified by drug selection (e.g., cells that have incorporated the selectable marker gene will survive, while the other cells die).

A host cell that includes an anti-polySia antibody of the present technology, such as a prokaryotic or eukaryotic host cell in culture, can be used to produce (i.e., express) recombinant anti-polySia antibody. In one embodiment, the method comprises culturing the host cell (into which a recombinant expression vector encoding the anti-polySia antibody has been introduced) in a suitable medium such that the anti-polySia antibody is produced. In another embodiment, the method further comprises the step of isolating the anti-polySia antibody from the medium or the host cell. Once expressed, collections of the anti-polySia antibody, e.g., the anti-polySia antibodies or the anti-polySia antibody-related polypeptides are purified from culture media and host cells. The anti-polySia antibody can be purified according to standard procedures of the art, including HPLC purification, column chromatography, gel electrophoresis and the like. In one embodiment, the anti-polySia antibody is produced in a host organism by the method of Boss et al., U.S. Pat. No. 4,816,397. Usually, anti-polySia antibody chains are expressed with signal sequences and are thus released to the culture media. However, if the anti-polySia antibody chains are not naturally secreted by host cells, the anti-polySia antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-polySia antibodies, e.g., the anti-polySia antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies. In one embodiment, the anti-polySia antibody of the present technology is a single-chain anti-polySia antibody. According to the present technology, techniques can be adapted for the production of single-chain antibodies specific to polySia (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology,* 203: 46-88, 1991; Shu, L. et al., *Proc. Natl. Acad. Sci. USA,* 90: 7995-7999, 1993; and Skerra et al., *Science* 240: 1038-1040, 1988.

Chimeric and Humanized Antibodies. In one embodiment, the anti-polySia antibody of the present technology is a chimeric anti-polySia antibody. In one embodiment, the anti-polySia antibody of the present technology is a humanized anti-polySia antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-polySia antibodies, such as chimeric and humanized monoclonal antibodies, comprising both human and non-human portions, can be made using standard recombinant DNA techniques, and are within the scope of the present technology. For some uses, including in vivo use of the anti-polySia antibody of the present technology in humans as well as use of these agents in in vitro detection assays, it is possible to use chimeric or humanized anti-polySia antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559; Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., *Molecular Immunology,* 28: 489-498, 1991; Studnicka et al., *Protein Engineering* 7: 805-814, 1994; Roguska et al., *PNAS* 91: 969-973, 1994), and chain shuffling (U.S. Pat. No. 5,565,332). In one embodiment, a cDNA encoding a murine anti-polySia monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240: 1041-1043; Liu et al. (1987) *Proc. Natl. Acad. Sci. USA* 84: 3439-3443; Liu et al. (1987) *J Immunol* 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559; U.S. Pat. Nos. 6,180,370; 6,300,064; 6,696,248; 6,706,484; 6,828,422.

In one embodiment, the present technology provides the construction of humanized anti-polySia antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for a humanized anti-polySia antibodies, heavy and light chain immunoglobulins.

CDR Antibodies. In some embodiments, the anti-polySia antibody of the present technology is an anti-polySia CDR antibody. Generally the donor and acceptor antibodies used to generate the anti-polySia CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one need replace only as many as necessary to permit adequate binding of the resulting CDR-grafted antibody to polySia. Methods for generating CDR-grafted and humanized antibodies are taught by Queen et al. U.S. Pat. Nos. 5,585,089; 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-polySia CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-polySia CDR-grafted antibody significantly compared to the same antibody with a fully human FR.

Bispecific Antibodies (BsAbs). A bispecific antibody is an antibody that can bind simultaneously to two targets that have a distinct structure, e.g., two different target antigens, two different epitopes on the same target antigen, or a hapten and a target antigen or epitope on a target antigen. BsAbs can be made, for example, by combining heavy chains and/or light chains that recognize different epitopes of the same or different antigen. In some embodiments, by molecular function, a bispecific binding agent binds one antigen (or epitope) on one of its two binding arms (one VH/VL pair), and binds a different antigen (or epitope) on its second arm (a different VH/VL pair). By this definition, a bispecific binding agent has two distinct antigen binding arms (in both specificity and CDR sequences), and is monovalent for each antigen to which it binds.

Bispecific antibodies (BsAb) and bispecific antibody fragments (BsFab) of the present technology have at least one arm that specifically binds to, for example, polySia and at least one other arm that specifically binds to a second target antigen. In some embodiments, the second target antigen is an antigen or epitope of a B-cell, a T-cell, a myeloid cell, a plasma cell, or a mast-cell. Additionally or alternatively, in certain embodiments, the second target antigen is selected from the group consisting of CD3, CD4, CD8, CD20, CD19, CD21, CD23, CD46, CD80, HLA-DR, CD74, CD22, CD14, CD15, CD16, CD123, TCR gamma/delta, NKp46 and KIR. In certain embodiments, the BsAbs are capable of binding to tumor cells that express polySia on the cell surface. In some embodiments, the BsAbs have been engineered to facilitate killing of tumor cells by directing (or recruiting) cytotoxic T cells to a tumor site. Other exemplary BsAbs include those with a first antigen binding site specific for polySia and a second antigen binding site specific for a small molecule hapten (e.g., DTP A, IMP288, DOTA, DOTA-Bn, DOTA-desferrioxamine, other DOTA-chelates described herein, Biotin, fluorescein, or those disclosed in Goodwin, D A. et al, 1994, *Cancer Res.* 54(22):5937-5946).

A variety of bispecific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In other embodiments, the bispecific fusion protein is tetravalent, comprising, for example, an immunoglobulin (e.g., IgG) with two binding sites for one antigen and two identical scFv for a second antigen. BsAbs composed of two scFv units in tandem have been shown to be a clinically successful bispecific antibody format. In some embodiments, BsAbs comprise two single chain variable fragments (scFvs) in tandem have been designed such that an scFv that binds a tumor antigen (e.g., polySia) is linked with an scFv that engages T cells (e.g., by binding CD3). In this way, T cells are recruited to a tumor site such that they can mediate cytotoxic killing of the tumor cells. See e.g., Dreier et al., *J. Immunol.* 170:4397-4402 (2003); Bargou et al., *Science* 321:974-977 (2008)).

Recent methods for producing BsAbs include engineered recombinant monoclonal antibodies which have additional cysteine residues so that they crosslink more strongly than the more common immunoglobulin isotypes. See, e.g., FitzGerald et al., *Protein Eng.* 10(10):1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Bispecific fusion proteins linking two or more different single-chain antibodies or antibody fragments are produced in similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any anti-polySia immunoglobulin disclosed herein. In some certain embodiments, scFvs are linked to the C-terminal end of the light chain of any anti-polySia immunoglobulin disclosed herein. In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the $V_H$ region of an anti-polySia antibody. The resulting vector can be used to transfect an appropriate host cell, such as a mammalian cell for the expression of the bispecific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a BsAb described herein based on specific properties imparted to the BsAb such as, for example, an increase in stability. In some embodiments, a BsAb of the present technology comprises a $G_4S$ linker (SEQ ID NO: 109). In some certain embodiments, a BsAb of the present technology comprises a $(G_4S)_n$ linker, wherein n is 1, 2, 3, 4, 5, 6, 7, 8, 9, 10, 11, 12, 13, 14, 15 or more (SEQ ID NO: 110).

Fc Modifications. In some embodiments, the anti-polySia antibodies of the present technology comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., *Nature*, 406:267-273 (2000). Examples of positions within the Fc region that make a direct contact with an Fc receptor such as an FcγR, include amino acids 234-239 (hinge region), amino acids 265-269 (B/C loop), amino acids 297-299 (C7E loop), and amino acids 327-332 (F/G) loop.

In some embodiments, an anti-polySia antibody of the present technology has an altered affinity for activating and/or inhibitory receptors, having a variant Fc region with one or more amino acid modifications, wherein said one or more amino acid modification is a N297 substitution with alanine, or a K322 substitution with alanine.

Glycosylation Modifications. In some embodiments, anti-polySia antibodies of the present technology have an Fc region with variant glycosylation as compared to a parent Fc region. In some embodiments, variant glycosylation includes the absence of fucose; in some embodiments, variant glycosylation results from expression in GnT1-deficient CHO cells.

In some embodiments, the antibodies of the present technology, may have a modified glycosylation site relative to an appropriate reference antibody that binds to an antigen of interest (e.g., polySia), without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach.

Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform that lacks certain oligosaccharides including fucose and terminal N-acetylglucosamine may be produced in special CHO cells and exhibit enhanced ADCC effector function.

In some embodiments, the carbohydrate content of an immunoglobulin-related composition disclosed herein is modified by adding or deleting a glycosylation site. Methods for modifying the carbohydrate content of antibodies are well known in the art and are included within the present technology, see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the carbohydrate content of an antibody (or relevant portion or component thereof) is modified by deleting one or more endogenous carbohydrate moieties of the antibody. In some certain embodiments, the present technology includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, *Nat. Biotechnol.* 17: 176-180; Davies et al., 2001, *Biotechnol. Bioeng.* 74:288-294; Shields et al., 2002, *J. Biol. Chem.* 277:26733-26740; Shinkawa et al., 2003, *J. Biol. Chem.* 278:3466-3473; U.S. Pat. No. 6,602,684; U.S. patent application Ser. No. 10/277, 370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; U.S. Patent Application Publication No. 2003/0115614; Okazaki et al., 2004, *JMB*, 336: 1239-49.

Fusion Proteins. In one embodiment, the anti-polySia antibody of the present technology is a fusion protein. The anti-polySia antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-polySia antibodies. For instance, a region of additional amino acids, particularly charged amino acids, can be added to the N-terminus of the anti-polySia antibody to improve stability and persistence during purification from the host cell or subsequent handling and storage. Also, peptide moieties can be added to an anti-polySia antibody to facilitate purification. Such regions can be removed prior to final preparation of the anti-polySia antibody. The addition of peptide moieties to facilitate handling of polypeptides are familiar and routine techniques in the art. The anti-polySia antibody of the present technology can be fused to marker sequences, such as a peptide which facilitates purification of the fused polypeptide. In select embodiments, the marker amino acid sequence is a hexa-histidine peptide (SEQ ID NO: 111), such as the tag provided in a pQE vector (QIAGEN, Inc., Chatsworth, Calif), among others, many of which are commercially available. As described in Gentz et al., *Proc. Natl. Acad. Sci. USA* 86: 821-824, 1989, for instance, hexa-histidine (SEQ ID NO: 111) provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., *J. Biochem.* 270: 3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.*, 270: 9459-9471, 1995.

Labeled Anti-polySia antibodies. In one embodiment, the anti-polySia antibody of the present technology is coupled with a label moiety, i.e., detectable group. The particular label or detectable group conjugated to the anti-polySia antibody is not a critical aspect of the technology, so long as it does not significantly interfere with the specific binding of the anti-polySia antibody of the present technology to polySia. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}$H, $^{14}$C, $^{35}$S, $^{125}$I, $^{121}$I, $^{131}$I, $^{112}$In, $^{99m}$Tc), other imaging agents such as microbubbles (for ultrasound imaging), $^{18}$F, $^{11}$C, $^{15}$O, (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals ($6^{th}$ Ed., Molecular Probes, Inc., Eugene OR.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-polySia antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-polySia antibodies. In this case, antigen-coated particles are agglutinated by samples comprising the target antibodies. In this format, none of the components need be labeled and the presence of the target antibody is detected by simple visual inspection.

B. Identifying and Characterizing the Anti-polySia Antibodies of the Present Technology Methods for identifying and/or screening the anti-polySia antibodies of the present technology. Methods useful to identify and screen antibodies against polySia species for those that possess the desired specificity to polySia include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS*, 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood*, 72: 1310-5, 1988); (3) the proliferation of peripheral blood mononuclear cells (PBMCs) in response to mitogens or mixed lymphocyte reaction can be measured using $^{3}$H-thymidine; (4) the phagocytic capacity of granulocytes, macrophages, and other phagocytes in PBMCs can be measured by placing PBMCs in wells together with labeled particles (Peters et al., *Blood*, 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-polySia antibodies of the present technology are selected using display of high DP polySia on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-polySia antibodies of the present technology are selected using display of high DP polySia on the surface of a yeast host cell. Methods useful for the isolation of scFv polypeptides by yeast surface display have been described by Kieke et al., *Protein Eng.* 1997 November; 10(11): 1303-10.

In some embodiments, anti-polySia antibodies of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

After selection of the desired anti-polySia antibodies, it is contemplated that said antibodies can be produced in large volume by any technique known to those skilled in the art, e.g., prokaryotic or eukaryotic cell expression and the like. The anti-polySia antibodies which are, e.g., but not limited to, anti-polySia hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of polySia Binding. In some embodiments, a polySia binding assay refers to an assay format wherein high DP polySia and an anti-polySia antibody are mixed under conditions suitable for binding between the high DP polySia and the anti-polySia antibody and assessing the amount of binding between the high DP polySia and the anti-polySia antibody. The amount of binding is compared with a suitable control, which can be the amount of binding in the absence of the high DP polySia, the amount of the binding in the presence of a non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of high DP polySia binding to anti-polySia antibody are, e.g., nuclear magnetic resonance, fluorescence, fluorescence polarization, surface plasmon resonance (BIACORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-polySia antibody is at least 1 percent greater than the binding observed in the absence of the candidate anti-polySia antibody, the candidate anti-polySia antibody is useful as an anti-polySia antibody of the present technology.

Measurement of polySia Neutralization. As used here, "polySia neutralization" refers to reduction of the activity and/or expression of polySia, or the reduction of the activity and/or expression of a protein modified with polySia moieties, through the binding of an anti-polySia antibody. The capacity of anti-polySia antibodies of the present technology to neutralize polySia activity/expression may be assessed in vitro or in vivo using methods known in the art.

Uses of the Anti-polySia Antibodies of the Present Technology

General. The anti-polySia antibodies of the present technology are useful in methods known in the art relating to the localization and/or quantitation of polySia (e.g., for use in measuring levels of high DP polySia within appropriate physiological samples, for use in diagnostic methods, for use in imaging the polypeptide, and the like). Antibodies of the present technology are useful to isolate high DP polySia by standard techniques, such as affinity chromatography or immunoprecipitation. An anti-polySia antibody of the present technology can facilitate the purification of immunoreactive high DP polySia species from biological samples, e.g., mammalian sera or cells as well as recombinantly-produced immunoreactive high DP polySia expressed in a host system. Moreover, anti-polySia antibodies can be used to detect immunoreactive high DP polySia species (e.g., in plasma, a cellular lysate or cell supernatant) in order to evaluate the abundance and pattern of expression of the immunoreactive high DP polySia. The anti-polySia antibodies of the present technology can be used diagnostically to monitor immunoreactive high DP polySia levels in tissue as part of a clinical testing procedure, e.g., to determine the efficacy of a given treatment regimen. As noted above, the detection can be facilitated by coupling (i.e., physically linking) the anti-polySia antibodies of the present technology to a detectable sub stance.

Detection of polySia. An exemplary method for detecting the presence or absence of an immunoreactive high DP polySia in a biological sample involves obtaining a biological sample from a test subject and contacting the biological sample with an anti-polySia antibody of the present technology capable of detecting an immunoreactive high DP polySia such that the presence of an immunoreactive high DP polySia is detected in the biological sample. Detection may be accomplished by means of a detectable label attached to the antibody.

The term "labeled" with regard to the anti-polySia antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-polySia antibodies disclosed herein are conjugated to one or more detectable labels. For such uses, anti-polySia antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled polySia-binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive high DP polySia in a biological sample in vitro as well as in vivo. In vitro techniques for detection of an immunoreactive high DP polySia include enzyme linked immunosorbent assays (ELISAs), Western blots, immunoprecipitations, radioimmunoassay, and immunofluorescence. Furthermore, in vivo techniques for detection of an immunoreactive high DP polySia include introducing into a subject a labeled anti-polySia antibody. For example, the anti-polySia antibody can be labeled with a radioactive marker whose presence and location in a subject can be detected by standard imaging techniques. In one embodiment, the biological sample contains high DP polySia from the test subject.

Immunoassay and Imaging. An anti-polySia antibody of the present technology can be used to assay immunoreactive high DP polySia levels in a biological sample (e.g., human plasma) using antibody-based techniques. For example, high DP polySia expression in tissues can be studied with classical immunohistological methods. Jalkanen, M. et al., *J. Cell. Biol.* 101: 976-985, 1985; Jalkanen, M. et al., *J. Cell. Biol.* 105: 3087-3096, 1987. Other antibody-based methods useful for detecting polySia expression include immunoassays, such as the enzyme linked immunosorbent assay (ELISA) and the radioimmunoassay (MA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium ($^{3}$H), indium ($^{112}$In), and technetium ($^{99m}$Tc), and fluorescent labels, such as fluorescein, rhodamine, and green fluorescent protein (GFP), as well as biotin.

In addition to assaying immunoreactive high DP polySia levels in a biological sample, anti-polySia antibodies of the present technology may be used for in vivo imaging of high DP polySia. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-polySia antibodies by labeling of nutrients for the relevant scFv clone.

An anti-polySia antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled anti-polySia antibody will then accumulate at the location of cells which contain the specific target antigen. For example, labeled anti-polySia antibodies of the present technology will accumulate within the subject in cells and tissues in which the high DP polySia has localized.

Thus, the present technology provides a diagnostic method of a medical condition, which involves: (a) assaying the expression of immunoreactive high DP polySia by measuring binding of an anti-polySia antibody of the present technology in cells or body fluid of an individual; (b) comparing the amount of immunoreactive high DP polySia present in the sample with a standard reference, wherein an increase or decrease in immunoreactive high DP polySia levels compared to the standard is indicative of a medical condition.

Affinity Purification. The anti-polySia antibodies of the present technology may be used to purify immunoreactive high DP polySia from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of an antibody polypeptide to a support. Accordingly, any of the conjugation methods and means disclosed herein with reference to conjugation of an antibody polypeptide to a solid support can also be applied for conjugation of a first support to a second support, where the first and second solid support can be the same or different.

Appropriate linkers, which can be cross-linking agents, for use for conjugating an antibody polypeptide to a solid support include a variety of agents that can react with a functional group present on a surface of the support, or with the antibody polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between an antibody polypeptide and the solid support. For example, a photolabile cross-linker, such as 3-amino-(2-nitrophenyl)propionic acid can be employed as a means for cleaving an antibody polypeptide from a solid support. (Brown et al., *Mol. Divers*, pp, 4-12 (1995); Rothschild et al., *Nucl. Acids Res.*, 24:351-66 (1996); and U.S. Pat. No. 5,643,722). Other cross-linking reagents are well-known in the art. (See, e.g., Wong (1991), supra; and Hermanson (1996), supra).

An antibody polypeptide can be immobilized on a solid support, such as a bead, through a covalent amide bond formed between a carboxyl group functionalized bead and the amino terminus of the antibody polypeptide or, conversely, through a covalent amide bond formed between an amino group functionalized bead and the carboxyl terminus of the antibody polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the antibody polypeptide is cleaved and can be removed. In such a case, the antibody polypeptide can be deposited as a beadless patch at the bottom of a well of a solid support or on the flat surface of a solid support. After addition of a matrix solution, the antibody polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the antibody polypeptide. Acid lability can also be changed. For example, trityl, monomethoxytrityl, dimethoxytrityl or trimethoxytrityl can be changed to the appropriate p-substituted, or more acid-labile tritylamine derivatives, of the antibody polypeptide, i.e., trityl ether and tritylamine bonds can be made to the antibody polypeptide. Accordingly, an antibody polypeptide can be removed from a hydrophobic linker, e.g., by disrupting the hydrophobic attraction or by cleaving trityl-ether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest (e.g., antibody polypeptide) to a solid support. Using such linkers, a first solid support, e.g., a bead, can be selectively cleaved from a second solid support, without cleaving the antibody polypeptide from the support; the antibody polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize an antibody polypeptide to the support. As desired, the linkage of the antibody polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with an antibody polypeptide, e.g., an antibody polypeptide containing an attached trityl group or with a second solid support having hydrophobic character.

A solid support can also be provided with a member of a specific binding pair and, therefore, can be conjugated to an antibody polypeptide or a second solid support containing a complementary binding moiety. For example, a bead coated with avidin or with streptavidin can be bound to an antibody polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either an antibody polypeptide or a solid support and, conversely, avidin or other biotin binding moiety would be incorporated into the support or the antibody polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-polySia Antibodies of the Present Technology

General. The anti-polySia antibodies of the present technology are useful in diagnostic methods. As such, the present technology provides methods using the antibodies in the diagnosis of high DP polySia activity in a subject. Anti-polySia antibodies of the present technology may be selected such that they have any level of epitope binding specificity and very high binding affinity to high DP polySia. In general, the higher the binding affinity of an antibody the more stringent wash conditions can be performed in an immunoassay to remove nonspecifically bound material without removing target antigen. Accordingly, anti-polySia antibodies of the present technology useful in diagnostic assays usually have binding affinities of about $10^8$ $M^{-1}$, $10^9$ $M^{-1}$, $10^{10}$ $M^{-1}$, $10^{11}$ $M^{-1}$ or $10^{12}$ $M^{-1}$. Further, it is desirable that anti-polySia antibodies used as diagnostic reagents have a sufficient kinetic on-rate to reach equilibrium under standard conditions in at least 12 h, at least five (5) h, or at least one (1) hour.

Anti-polySia antibodies can be used to detect an immunoreactive high DP polySia in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of high DP polySia in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-polySia antibody or a population of anti-polySia antibodies immobilized to a solid phase, and another anti-polySia antibody or a population of anti-polySia antibodies in solution. Typically, the solution anti-polySia antibody or population of anti-polySia antibodies is labeled. If an antibody population is used, the population can contain antibodies binding to polySia with different degrees of polymerization. Accordingly, the same population can be used for both solid phase and solution antibody. If anti-polySia monoclonal antibodies are used, first and second polySia monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting polySia with the anti-polySia antibody, a sample is incubated for a period that usually varies from about 10 min to about 24 hr and is usually about 1 hr. A wash step is then performed to remove components of the sample not specifically bound to the anti-polySia antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive high DP polySia in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the high DP polySia in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-polySia antibodies can be joined to a linker molecule, such as biotin for attachment to a surface bound linker, such as avidin.

In some embodiments, the present disclosure provides an anti-polySia antibody of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MM, when used along with the anti-polySia antibodies of the present technology.

Macrocyclic chelates such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, such as radionuclides of gallium, yttrium and copper, respectively. Such metal-chelate complexes can be stabilized by tailoring the ring size to the metal of interest. Examples of other DOTA chelates include (i) DOTA-Phe-Lys(HSG)-D-Tyr-Lys(HSG)-NH$_2$; (ii) Ac-Lys(HSG)D-Tyr-Lys(HSG)-Lys(Tscg-Cys)-NH$_2$; (iii) DOTA-D-Asp-D-Lys(HSG)-D-Asp- D-Lys(HSG)-NH₂; (iv) DOTA-D-Glu-D-Lys(HSG)-D-Glu-D-Lys(HSG)-NH₂; (v) DOTA-D-Tyr-D-Lys(HSG)-D-Glu-D-Lys(HSG)-NH₂; (vi) DOTA-D-Ala-D-Lys(HSG)-D-Glu-D-Lys(HSG)-NH₂; (vii) DOTA-D-Phe-D-Lys(HSG)-D-Tyr-D-Lys(HSG)-NH₂; (viii) Ac-D-Phe-D-Lys(DOTA)-D-Tyr-D-Lys(DOTA)-NH₂; (ix) Ac-D-Phe-D-Lys(DTPA)-D-Tyr-D-Lys(DTPA)-NH₂; (x) Ac-D-Phe-D-Lys(Bz-DTPA)-D-Tyr-D-Lys(Bz-DTPA)-NH₂; (xi) Ac-D-Lys(HSG)-D-Tyr-D-Lys(HSG)-D-Lys(Tscg-Cys)-NH₂; (xii) DOTA-D-Phe-D-Lys(HSG)-D-Tyr-D-Lys(HSG)-D-Lys(Tscg-Cys)-NH₂; (xiii) (Tscg-Cys)-D-Phe-D-Lys(HSG)-D-Tyr-D-Lys(HSG)-D-Lys(DOTA)-NH₂; (xiv) Tscg-D-Cys-D-Glu-D-Lys(HSG)-D-Glu-D-Lys(HSG)-NH₂; (xv) (Tscg-Cys)-D-Glu-D-Lys(HSG)-D-Glu-D-Lys(HSG)-NH₂; (xvi) Ac-D-Cys-D-Lys(DOTA)-D-Tyr-D-Ala-D-Lys(DOTA)-D-Cys-NH₂; (xvii) Ac-D-Cys-D-Lys(DTPA)-D-Tyr-D-Lys(DTPA)-NH₂; (xviii) Ac-D-Lys(DTPA)-D-Tyr-D-Lys(DTPA)-D-Lys(Tscg-Cys)-NH₂; and (xix) Ac-D-Lys(DOTA)-D-Tyr-D-Lys(DOTA)-D-Lys(Tscg-Cys)-NH₂.

Other ring-type chelates such as macrocyclic polyethers, which are of interest for stably binding nuclides, such as $^{223}$Ra for RAIT are also contemplated.

B. Therapeutic Use of Anti-polySia Antibodies of the Present Technology

The immunoglobulin-related compositions (e.g., antibodies or antigen binding fragments thereof) of the present technology are useful for the treatment of polySia associated cancers. Such treatment can be used in patients identified as having pathologically high levels of high DP polySia (e.g., those diagnosed by the methods described herein) or in patients diagnosed with a disease known to be associated with such pathological levels. In one aspect, the present disclosure provides a method for treating a polySia associated cancer in a subject in need thereof, comprising administering to the subject an effective amount of an antibody (or antigen binding fragment thereof) of the present technology. Examples of cancers that can be treated by the antibodies of the present technology include, but are not limited to: small cell or non-small cell lung cancer, neuroblastoma, pancreatic cancer, pituitary tumors, Wilm's tumor, rhabdomyosarcoma, glioblastoma, breast cancer, or acute myeloid leukemia.

The compositions of the present technology may be employed in conjunction with other therapeutic agents useful in the treatment of polySia associated cancers. For example, the antibodies of the present technology may be separately, sequentially or simultaneously administered with at least one additional therapeutic agent-selected from the group consisting of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

The compositions of the present technology may optionally be administered as a single bolus to a subject in need thereof. Alternatively, the dosing regimen may comprise multiple administrations performed at various times after the appearance of tumors.

Administration can be carried out by any suitable route, including orally, intranasally, parenterally (intravenously, intramuscularly, intraperitoneally, or subcutaneously), rectally, intracranially, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-polySia antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-polySia antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 μg/mL to about 125 μg/mL, 100 μg/mL to about 150 μg/mL, from about 125 μg/mL to about 175 μg/mL, or from about 150 μg/mL to about 200 μg/mL. Alternatively, anti-polySia antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In another aspect, the present disclosure provides a method for detecting a tumor in a subject in vivo comprising (a) administering to the subject an effective amount of an antibody (or antigen binding fragment thereof) of the present technology, wherein the antibody is configured to localize to a tumor expressing polySia and is labeled with a radioisotope; and (b) detecting the presence of a tumor in the subject by detecting radioactive levels emitted by the antibody that are higher than a reference value. In some embodiments, the reference value is expressed as injected dose per gram (% ID/g). The reference value may be calculated by measuring the radioactive levels present in non-tumor (normal) tissues, and computing the average radioactive levels present in non-tumor (normal) tissues±standard deviation. In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, $^{188}$Re, $^{177}$Lu, and $^{67}$Cu. Examples of alpha particle-emitting isotopes include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Examples of Auger-emitters include $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, and $^{203}$Pb. In some embodiments of the method, nonspecific FcR-dependent binding in normal tissues is eliminated or reduced (e.g., via N297A mutation in Fc region, which results in aglycosylation). The therapeutic effectiveness of such an immunoconjugate may be determined by computing the area under the curve (AUC) tumor:AUC normal tissue ratio. In some embodiments, the immunoconjugate has a AUC tumor:AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

PRIT. In one aspect, the present disclosure provides a method for detecting solid tumors in a subject in need thereof comprising (a) administering to the subject an effective amount of a complex comprising a radiolabeled DOTA hapten and a bispecific antibody of the present technology that binds to the radiolabeled DOTA hapten and a high DP polySia antigen, wherein the complex is configured to localize to a solid tumor expressing the high DP polySia antigen recognized by the bispecific antibody of the complex; and (b) detecting the presence of solid tumors in the subject by detecting radioactive levels emitted by the complex that are higher than a reference value. In some embodiments, the subject is human.

In another aspect, the present disclosure provides a method for selecting a subject for pretargeted radioimmunotherapy comprising (a) administering to the subject an effective amount of a complex comprising a radiolabeled DOTA hapten and a bispecific antibody of the present technology that binds to the radiolabeled DOTA hapten and a high DP polySia antigen, wherein the complex is configured to localize to a solid tumor expressing the high DP polySia antigen recognized by the bispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

Examples of DOTA haptens include (i) DOTA-Phe-Lys(HSG)-D-Tyr-Lys(HSG)-NH$_2$; (ii) Ac-Lys(HSG)D-Tyr-Lys(HSG)-Lys(Tscg-Cys)-NH$_2$; (iii) DOTA-D-Asp-D-Lys(HSG)-D-Asp-D-Lys(HSG)-NH$_2$; (iv) DOTA-D-Glu-D-Lys(HSG)-D-Glu-D-Lys(HSG)-NH$_2$; (v) DOTA-D-Tyr-D-Lys(HSG)-D-Glu-D-Lys(HSG)-NH$_2$; (vi) DOTA-D-Ala-D-Lys(HSG)-D-Glu-D-Lys(HSG)-NH$_2$; (vii) DOTA-D-Phe-D-Lys(HSG)-D-Tyr-D-Lys(HSG)-NH$_2$; (viii) Ac-D-Phe-D-Lys(DOTA)-D-Tyr-D-Lys(DOTA)-NH$_2$; (ix) Ac-D-Phe-D-Lys(DTPA)-D-Tyr-D-Lys(DTPA)-NH$_2$; (x) Ac-D-Phe-D-Lys(Bz-DTPA)-D-Tyr-D-Lys(Bz-DTPA)-NH$_2$; (xi) Ac-D-Lys(HSG)-D-Tyr-D-Lys(HSG)-D-Lys(Tscg-Cys)-NH$_2$; (xii) DOTA-D-Phe-D-Lys(HSG)-D-Tyr-D-Lys(HSG)-D-Lys(Tscg-Cys)-NH$_2$; (xiii) (Tscg-Cys)-D-Phe-D-Lys(HSG)-D-Tyr-D-Lys(HSG)-D-Lys(DOTA)-NH$_2$; (xiv) Tscg-D-Cys-D-Glu-D-Lys(HSG)-D-Glu-D-Lys(HSG)-NH$_2$; (xv) (Tscg-Cys)-D-Glu-D-Lys(HSG)-D-Glu-D-Lys(HSG)-NH$_2$; (xvi) Ac-D-Cys-D-Lys(DOTA)-D-Tyr-D-Ala-D-Lys(DOTA)-D-Cys-NH$_2$; (xvii) Ac-D-Cys-D-Lys(DTPA)-D-Tyr-D-Lys(DTPA)-NH$_2$; (xviii) Ac-D-Lys(DTPA)-D-Tyr-D-Lys(DTPA)-D-Lys(Tscg-Cys)-NH$_2$; (xix) Ac-D-Lys(DOTA)-D-Tyr-D-Lys(DOTA)-D-Lys(Tscg-Cys)-NH$_2$ and (xx) DOTA. The radiolabel may be an alpha particle-emitting isotope, a beta particle-emitting isotope, or an Auger-emitter. Examples of radiolabels include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having a polySia-associated cancer such as small cell or non-small cell lung cancer, neuroblastoma, pancreatic cancer, pituitary tumors, Wilm's tumor, rhabdomyosarcoma, glioblastoma, breast cancer, or acute myeloid leukemia.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the complex is administered into the cerebral spinal fluid or blood of the subject.

In some embodiments of the methods disclosed herein, the radioactive levels emitted by the complex are detected between 2 to 120 hours after the complex is administered. In certain embodiments of the methods disclosed herein, the radioactive levels emitted by the complex are expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with a polySia-associated cancer comprising (a) administering an effective amount of an anti-DOTA bispecific antibody of the present technology to the subject, wherein the anti-DOTA bispecific antibody is configured to localize to a tumor expressing high DP polySia; and (b) administering an effective amount of a radiolabeled-DOTA hapten to the subject, wherein the radiolabeled-DOTA hapten is configured to bind to the anti-DOTA bispecific antibody. In some embodiments, the subject is human.

The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody.

The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled-DOTA hapten may be administered at any time after 4 or more days following administration of the anti-DOTA bispecific antibody.

Additionally or alternatively, in some embodiments, the method further comprises administering an effective amount of a clearing agent to the subject prior to administration of the radiolabeled-DOTA hapten. A clearing agent can be any molecule (dextran or dendrimer or polymer) that can be conjugated with C825-hapten. In some embodiments, the clearing agent is no more than 2000 kD, 1500 kD, 1000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, or 5 kD. In some embodiments, the clearing agent is a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.).

In some embodiments, the clearing agent and the radiolabeled-DOTA hapten are administered without further administration of the anti-DOTA bispecific antibody of the present technology. For example, in some embodiments, an anti-DOTA bispecific antibody of the present technology is administered according to a regimen that includes at least one cycle of: (i) administration of the anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Additionally or alternatively, in some embodiments of the method, the anti-DOTA bispecific antibody and/or the radiolabeled-DOTA hapten is administered intravenously, intramuscularly, intraarterially, intrathecally, intracapsularly, intraorbitally, intradermally, intraperitoneally, transtracheally, subcutaneously, intracerebroventricularly, orally or intranasally.

In one aspect, the present disclosure provides a method for increasing tumor sensitivity to radiation therapy in a subject diagnosed with a polySia-associated cancer comprising administering to the subject an effective amount of a complex comprising a radiolabeled-DOTA hapten and a bispecific antibody of the present technology that recognizes and binds to the radiolabeled-DOTA hapten and a high DP polySia antigen target, wherein the complex is configured to localize to a tumor expressing the high DP polySia antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the subject is human.

In another aspect, the present disclosure provides a method for treating cancer in a subject in need thereof comprising (a) administering an effective amount of an anti-DOTA bispecific antibody of the present technology to the subject, wherein the anti-DOTA bispecific antibody is configured to localize to a tumor expressing a high DP polySia antigen target; and (b) administering an effective amount of a radiolabeled-DOTA hapten to the subject, wherein the radiolabeled-DOTA hapten is configured to bind to the anti-DOTA bispecific antibody. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody. In some embodiments, the subject is human.

Accordingly, in some embodiments, the method further comprises administering an effective amount of a clearing agent to the subject prior to administration of the radiolabeled-DOTA hapten. The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled- DOTA hapten may be administered at any time after 4 or more days following administration of the anti-DOTA bispecific antibody.

The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the clearing agent and the radiolabeled-DOTA hapten are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Also provided herein are methods for treating cancer in a subject in need thereof comprising administering to the subject an effective amount of a complex comprising a radiolabeled-DOTA hapten and a bispecific antibody of the present technology that recognizes and binds to the radiolabeled-DOTA hapten and a high DP polySia antigen target, wherein the complex is configured to localize to a tumor expressing the high DP polySia antigen target recognized by the bispecific antibody of the complex. The therapeutic effectiveness of such a complex may be determined by computing the area under the curve (AUC) tumor:AUC normal tissue ratio. In some embodiments, the complex has a AUC tumor:AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Toxicity. Optimally, an effective amount (e.g., dose) of anti-polySia antibody described herein will provide therapeutic benefit without causing substantial toxicity to the subject. Toxicity of the anti-polySia antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-polySia antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions. According to the methods of the present technology, the anti-polySia antibody can be incorporated into pharmaceutical compositions suitable for administration. The pharmaceutical compositions generally comprise recombinant or substantially purified antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, PA $18^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-polySia antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-polySia antibody named in this technology can be present in unsalified or unesterified form, or in salified and/or esterified form, and the naming of such anti-polySia antibody is intended to include both the original (unsalified and unesterified) compound and its pharmaceutically-acceptable salts and esters. Also, certain embodiments of the present technology can be present in more than one stereoisomeric form, and the naming of such anti-polySia antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-polySia antibody, use thereof in the compositions is contemplated. Supplementary active compounds can also be incorporated into the compositions.

A pharmaceutical composition of the present technology is formulated to be compatible with its intended route of administration. The anti-polySia antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-polySia antibody can optionally be administered in combination with other agents that are at least partly effective in treating various polySia associated cancers.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-polySia antibody of the present technology in the required amount in an appropriate solvent with one or a combination of ingredients enumerated above, as required, followed by filtered sterilization. Generally, dispersions are prepared by incorporating the anti-polySia antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-polySia antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-polySia antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-polySia antibody is formulated into ointments, salves, gels, or creams as generally known in the art.

The anti-polySia antibody can also be prepared as pharmaceutical compositions in the form of suppositories (e.g., with conventional suppository bases such as cocoa butter and other glycerides) or retention enemas for rectal delivery.

In one embodiment, the anti-polySia antibody is prepared with carriers that will protect the anti-polySia antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

C. Kits

The present technology provides kits for the detection and/or treatment of polySia associated cancers, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of polySia associated cancers. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive high DP polySia in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, or bispecific anti-polySia antibodies of the present technology (or antigen binding fragments thereof) capable of binding a high DP polySia in a biological sample; means for determining the amount of the high DP polySia in the sample; and means for comparing the amount of the immunoreactive high DP polySia in the sample with a standard. One or more of the anti-polySia antibodies may be labeled. The kit components, (e.g., reagents) can be packaged in a suitable container. The kit can further comprise instructions for using the kit to detect the immunoreactive high DP polySia.

For antibody-based kits, the kit can comprise, e.g., 1) a first antibody, e.g. a humanized, chimeric or bispecific anti-polySia antibody of the present technology (or an antigen binding fragment thereof), attached to a solid support, which binds to a high DP polySia; and, optionally; 2) a second, different antibody which binds to either the high DP polySia or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a high DP polySia in vitro or in vivo, or for treatment of polySia associated cancers in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative anti-polySia antibodies of the present technology. The following Examples demonstrate the production of chimeric, humanized, and bispecific antibodies of the present technology, and characterization of their binding specificities and in vivo biological activities.

Example 1: Materials and Methods for Generating and Characterizing the polySialic Acid Antibodies of the Present Technology Generation of polySia×CD3 Bispecific antibody. polySia×CD3 BsAb was constructed by fusing the humanized OKT3 scFv onto the C-terminus of the light chain of P35 H1L2 antibody via a $(G_4S)_3$ linker (SEQ ID NO: 112) as previously described in Xu H et al., *Cancer Immunology Research* 3:266-277 (2015) and Lopez-Albaitero A et al., *OncoImmunology* 6:e1267891 (2017). N297A and K322A mutations were introduced in the Fc region of the antibody to eliminate FcR and complement binding activities, respectively (Shields R L et al., *Journal of Biological Chemistry* 276:6591-6604 (2001); Idusogie E E et al., *Journal of Immunology* 164:4178-4184 (2000)). The DNA construct was then transfected into CHO—S cells and stable clones were selected for high levels of antibody production. For larger-scale antibody purification, the selected stable clone was expanded in shaker flasks. Bispecific antibody was purified from supernatant using one-step protein A affinity chromatography.

SEC-HPLC Analysis. Size and purity of BC137 was analyzed using HPLC system (Shimadzu Scientific Instruments Inc., Columbia, MD). Monomeric species were identified using a molecular weight standard (Bio-Rad Laboratories, Hercules, CA) and percent monomer was calculated based on the relative area under curve (AUC) of different non-buffer peaks.

T-cell dependent cytotoxicity (TDCC) assays. Cytotoxicity assays were performed using both $^{51}$Cr-release assay or Pierce LDH-release assay (Thermo Fisher Scientific, Cambridge, MA). For both assays, T cells activated by exposure to anti-CD3/anti-CD28 Dynabeads for 14 days were subsequently used as effector cells, excepted for sorted cells from PBMCs, which were used for TDCC assay without prior stimulation. $^{51}$Cr assay was performed as previously described in Cheng M et al., *International Journal of Cancer* 136:476-486 (2015). LDH assay was conducted according to the manufacturer's instructions with the following modifications. Briefly, for each assay well of a 96-well round-bottom plate, $1.5 \times 10^4$ target cells were incubated with variable number of effector cells, depending on the intended (effector:target) E:T ratios. Antibodies were then added at different dilutions and the plates were incubated at 37° C. for 16 hours. Each condition was done in triplicates. Supernatant was then transferred to a flat bottom plate with reaction substrate and incubated for 30 min before reading at 490 nm, with 680 nm as a reference wavelength. $EC_{50}$ values were calculated by fitting the curves to a 4-parameter nonlinear regression model using GraphPad Prism.

In Vivo Tumor Therapy. To test the anti-tumor efficacy of BC137, immunodeficient mice were used for human tumor xenografts. Neuroblastoma IMR-32 tumors were implanted subcutaneously, where tumor cells were mixed with Matrigel and implanted at the flank of Balb/c $Rag2^{-/-}IL2R\gamma^{-/-}$ (DKO) mice (now commercially available from Taconic (Rensselaer, New York) as CIEA BRG mice). Tumor growth was monitored by weekly measurement of tumor volume using a caliper or a digital device Peira TM900 Scanner (Peira Scientific Instruments, Turnhout, Belgium).

On day 7 post tumor implantation, the treatment was started. 100 μg BsAb was injected to each mouse (i.v., twice per week, five weeks) and 10 million CD3/CD28 beads activated T-cells (once per week, five weeks) were injected on the next day.

Affinity Maturation Using Yeast Display. Parental P35 H1L2 was converted into scFv format with a 20 amino acid $(G4S)_3$ linker (SEQ ID NO: 112) and cloned into a yeast display vector. P35 H1L2 scFv was randomly mutated using GeneMorph II mutagenesis kit (Agilent Technologies, Santa Clara, CA). PCR products were electroporated together with linearized vector into yeast and the library was subjected to 4 rounds of sorting using biotinylated polySia. Individual clones from the last round were PCR amplified and sequenced to analyze the mutation pattern. Conversion of selected scFv clones into BsAb format was done using a one-step 4-fragment ligation method with 50 ng linearized vector and a 1:3 vector to insert molar ratio for the other 3 components. Ligation was done with Rapid DNA ligation kit (Thermo Fisher Scientific, Cambridge, MA) at room temperature for 1 hour. Type II restriction enzyme SapI (New England Biolabs, Ipswich, MA) was used to ensure seamless linkage among the different components. Selected clones were transiently expressed using Expi293 expression system (Thermo Fisher Scientific, Cambridge, MA) according to the manufacturer's instructions. Supernatant from Expi293 cells after 4-5 days of culture in shaking flasks was used to purify antibodies using Mab Select SuRe (GE Healthcare, Chicago, IL) and dialyzed against pH 8.0 citrate buffer in dialysis membrane (Spectrum Laboratories, Inc., Rancho Dominguez, CA).

Surface Plasmon Resonance (SPR) analysis. Colominic acid (polySia with ~100 Sia units) was immobilized on CMS chips. Five concentrations of 2-fold serially diluted antibody IgG or BsAb were flowed over the chip using a Biacore™ T100 system (GE Healthcare, Chicago, IL). Binding kinetics measured at 25° C. The sensorgrams were fitted with 1:1 binding model for both to derive kinetic parameters.

Example 2: Generation of Chimeric and Humanized P35 Antibodies

Chimeric and humanized anti-polySia antibodies were generated using CDR grafting methods using closely homologous human germline sequences. Two different humanized VH (P35 H1, P35 H2) and humanized VL (P35 L1, P35 L2) sequences were combined to generate 4 different humanized anti-polySia IgG1 antibodies. FIG. 3 demonstrates differences in antigen-binding by flow cytometry of the four combinations, H1L1, H1L2, H2L1 and H2L2. P35 H1L2 exhibited the highest binding (FIG. 3), and was further investigated.

These results demonstrate that the antibodies of the present technology or antigen binding fragments thereof, specifically bind to a polysialic acid antigen with high binding affinity. Accordingly, the immunoglobulin-related compositions disclosed herein are useful in methods for detecting polysialic acid with a high degree of polymerization (high DP polySia) in a sample as well as in methods for detecting tumors in a subject.

Example 3: Expression of polySia on Multiple Cancer Cell Lines

The expression of polySia was tested on a large panel of cancer cell lines using the chimeric P35 IgG1. An isotype-matched control antibody (anti-RSV palivizumab) was used as a control, and the mean fluorescence intensities are shown in FIGS. 1(A) and 1(B). High levels of polySia were observed for neuroblastoma, small cell lung cancer (SCLC), and for acute myeloid leukemia (AML). The detection of polySia in AML cells was unexpected given that high levels of polySia haven't been previously reported for AML.

These results demonstrate that the antibodies of the present technology or antigen binding fragments thereof, specifically bind to a polysialic acid antigen with high binding affinity. Accordingly, the immunoglobulin-related compositions disclosed herein are useful in methods for detecting polysialic acid with a high degree of polymerization (high DP polySia) in a sample as well as in methods for detecting tumors in a subject.

Example 4: Expression of polySia on SCLC Patient Derived Xenografts (PDX)

The expression of polySia on 14 different SCLC PDX samples was tested by immunohistochemistry using the chimeric P35 antibody. Evaluation of the samples using a grading scale of 1 to 4, 11 out of the 14 samples showed areas of high levels of staining (grade 3 or 4). See FIG. 2.

These results demonstrate that the antibodies of the present technology or antigen binding fragments thereof, specifically bind to a polysialic acid antigen with high binding affinity. Accordingly, the immunoglobulin-related compositions disclosed herein are useful in methods for detecting polysialic acid with a high degree of polymerization (high DP polySia) in a sample as well as in methods for detecting tumors in a subject.

Example 5: Generation of polySia×CD3 Bispecific Antibody

Figure 4A:
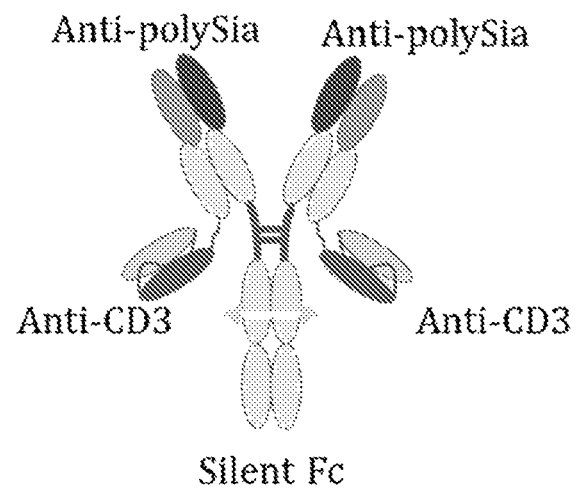
FIG. 4(A) shows a schematic diagram of polySia×CD3 bispecific antibody in IgG-scFv format.
Figure 4B:
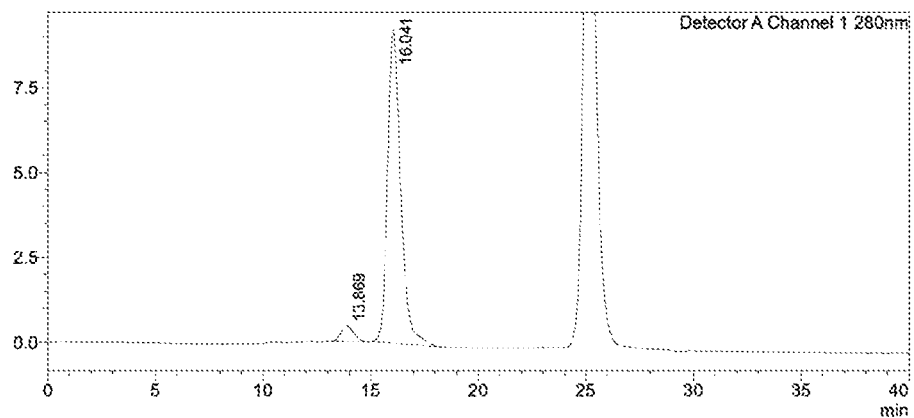
FIG. 4(B) shows the purity of polySia×CD3 bispecific antibody BC137 by SEC- HPLC, where the major peak (16.0 minutes) is the fully paired BsAb (molecular weight ~210 kDa) and the salt buffer peak (25 minutes).
Figure 66:
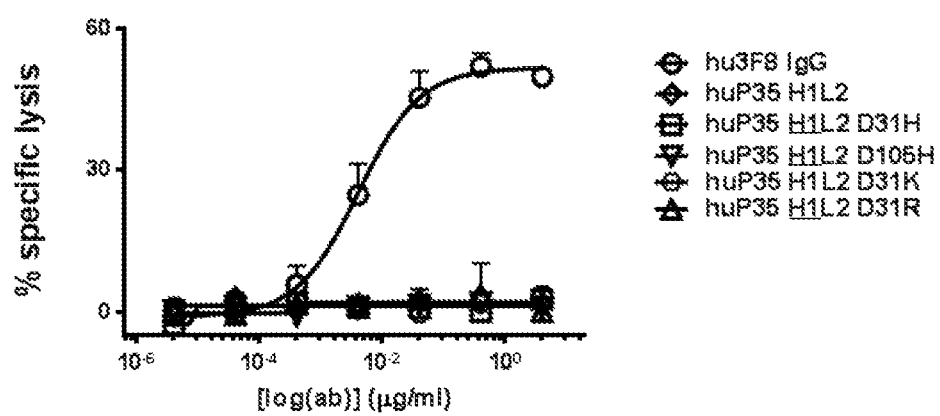
FIG. 66 shows an antibody-dependent cell-mediated cytotoxicity (ADCC) assay with humanized P35 IgG1 antibodies on the neuroblastoma cell line IMR-32 Luc.

When tested for antibody-dependent cell-mediated cytotoxicity (ADCC) against the polySia(+) cell lines, the humanized P35 IgG1 antibodies did not exhibit anti-tumor activity (FIG. 66). To confer anti-tumor properties to the humanized P35 antibodies, bispecific antibodies were generated that targeted polySia×CD3 so as to re-direct T cells for tumor killing. FIG. 4(A) shows a schematic diagram for the polySia×CD3 BsAb. The first BsAb generated utilized the P35 H1L2 sequence to make Biclone 137 (BC137). FIG. 4(B) shows the purity of the polySia×CD3 bispecific antibody BC137 by SEC-HPLC, with a major peak for BC137 (95% by absorbance at 280 nm) with an approximate MW of 210 kDa. The BC137 BsAb remained stable by SEC-HPLC after multiple freeze and thaw cycles.

Example 6: polySia-BsAb Redirected T-Cell Cytotoxicity of Human Cancer Cell Lines PolySia(+) cell lines melanoma M14 and neuroblastoma IMR-32 were tested in 24-hour lactate dehydrogenase (LDH) cytotoxicity assay with activated human T-cells (effector/target ratio: 10:1) to test BC137 redirected T-cell cytotoxicity.

Figure 5A:
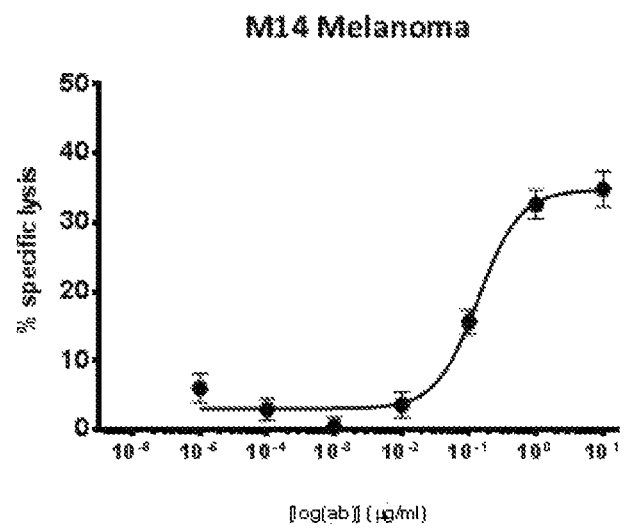
FIG. 5(A) shows a T cell dependent cytotoxicity assay (TDCC) with BC137 on melanoma cell line M14.
Figure 5B:
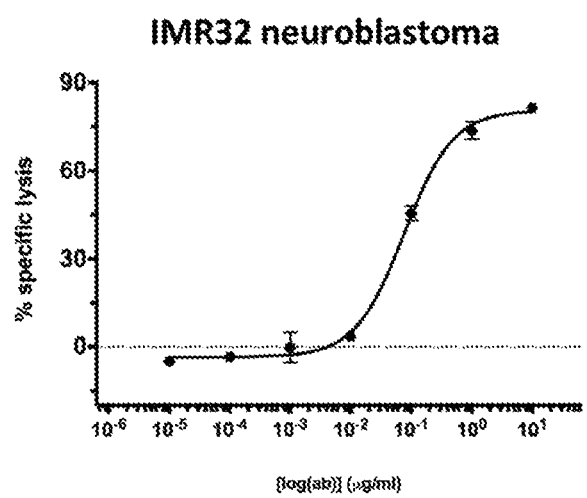
FIG. 5(B) shows a T cell dependent cytotoxicity assay (TDCC) with BC137 on neuroblastoma cell line IMR-32.

FIGS. 5(A)-5(B) demonstrate that BC137 exhibited $EC_{50}$ values near 100 ng/ml (~450 pM). The high T-cell dependent cell-mediated cytotoxicity (TDCC) exhibited by BC137 was unexpected given the lack of ADCC exhibited by the humanized P35 H1L2 antibodies.

These results demonstrate that the antibodies of the present technology or antigen binding fragments thereof, specifically bind to a polysialic acid antigen with high binding affinity. Accordingly, the immunoglobulin-related compositions disclosed herein are useful in methods for detecting polysialic acid with a high degree of polymerization (high DP polySia) in a sample as well as in methods for detecting tumors in a subject.

Figure 6:
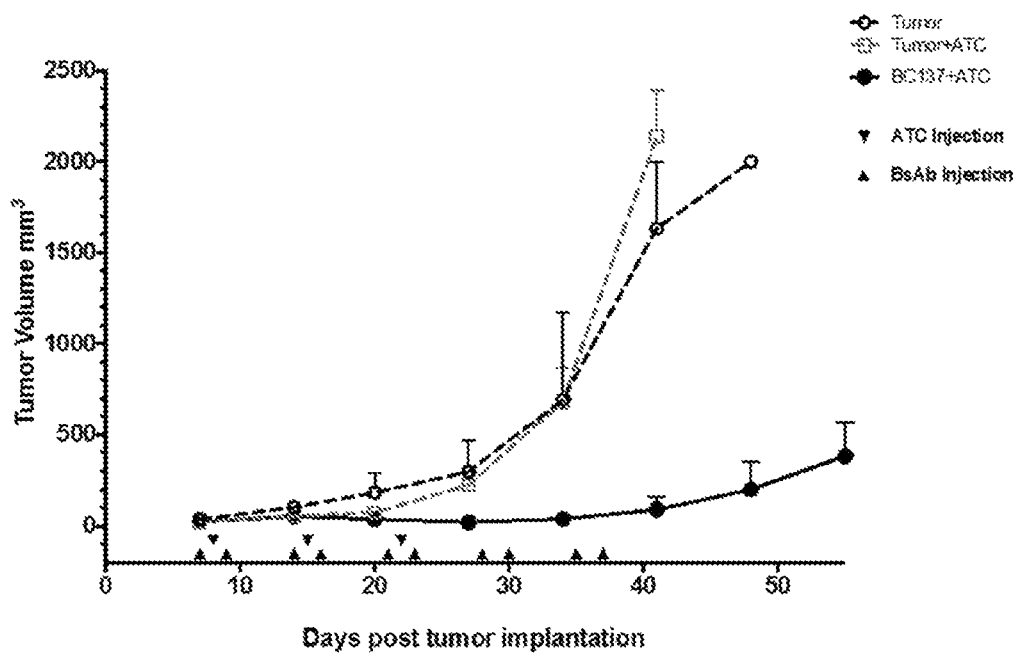
FIG. 6 shows the tumor volumes in a mouse xenograft study with neuroblastoma IMR-32 tumors treated with BC137 and activated T cells (ATC).

Example 7: polySia-BsAb Showed Anti-Tumor Potency in Mouse Xenograft Study with Neuroblastoma IMR-32 Tumor To test the anti-tumor efficacy of BC137, immunodeficient mice were used for human tumor xenografts. Neuroblastoma IMR-32 tumors were implanted subcutaneously, at the flank of Balb/c $Rag2^{-/-}IL2R\gamma^{-/-}$ (DKO) mice. As shown in FIG. 6, without antibody treatment, both tumor only and tumor+ activated T-cells groups exhibited rapid tumor growth. In contrast, 10 doses of BC137 over 5 weeks effectively cured the mice, which remained tumor free for at least 50 days. No clinical toxicity was observed.

Taken together, these results demonstrate that the antibodies or antigen binding fragments of the present technology can detect tumors and inhibit the progression of tumor growth and/or metastasis. Accordingly, the immunoglobulin-related compositions disclosed herein are useful in methods for detecting and/or treating a polySia associated cancer in a subject in need thereof.

Figure 7A:
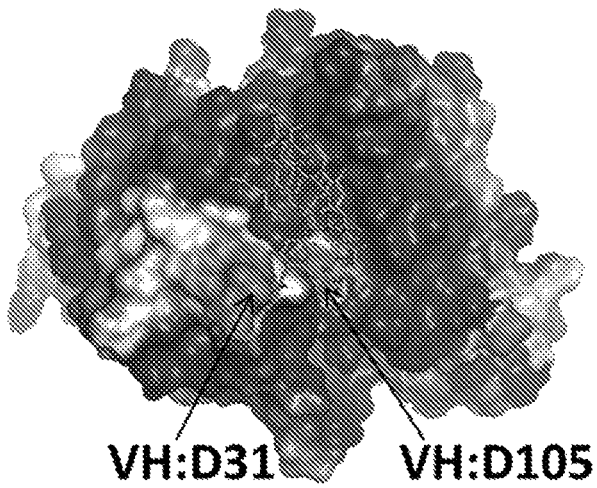
FIG. 7(A) shows an electrostatic potential map of the binding pocket of mAb735 with bound octasialic acid, based on the crystal structure PDB 3WDB, with two negatively charged resides, VH:D31 and VH:D105.
Figure 7B:
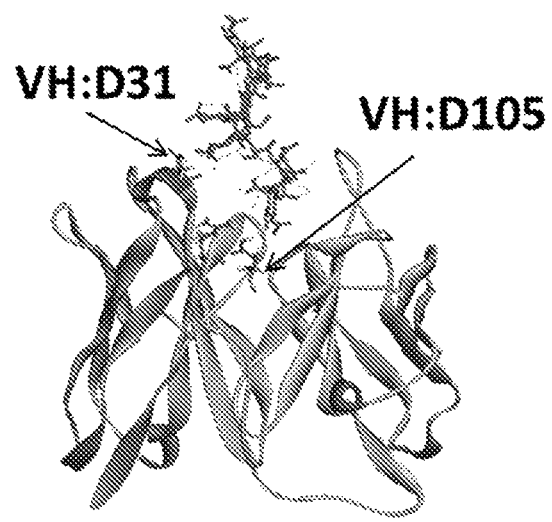
FIG. 7(B) shows a side view in ribbon diagram of the binding pocket of mAb735 with bound octasialic acid, based on the crystal structure PDB 3WDB, with two negatively charged resides, VH:D31 and VH:D105.
Figure 7C:
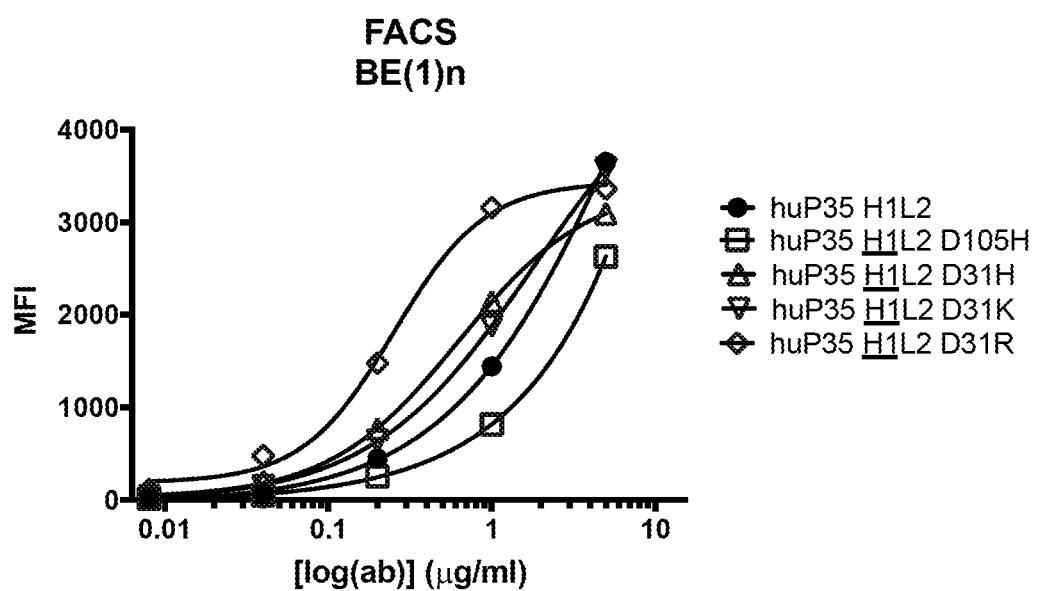
FIG. 7(C) shows the relative binding of P35 H1L2 IgG1 parental and with mutations designed by rational engineering.

Example 8: Affinity Maturation of Anti-polySia Antibodies by in Silico Modelling and Rational Design In an attempt to further increase the potency of BC137, affinity maturation was attempted by both rational engineering and random mutagenesis/yeast display. For the rational engineering, electrostatic analysis was done on the binding pocket of mAb735 based on the crystal structure of the scFv bound to an octasialic acid ligand, that had previously been solved (PDB 3WDB). An electrostatic surface map was generated using DelPhi algorithm using Biovia Discovery Studio modelling software (Dassault System, San Diego, CA) (FIG. 7(A)). The electrostatic potential map showed 2 negatively charged residues (VH:D31 at the surface of the pocket, and VH:D105 deep in the binding pocket). FIG. 7(B) shows a cross-sectional ribbon diagram of the binding pocket of mAB735. Without wishing to be bound by theory, it is believed that altering the charge at D31 and D105 to a positively charged residue enhances polySia binding. Mutations were introduced into P35 H1L2 IgG1 at these sites and then tested for binding to polySia(+) neuroblastoma BE(1)n cells. Surprisingly, D105H showed weaker binding than the parental P35 H1L2, whereas positively charged amino acids at D31 showed enhanced binding; with D31R showing the most enhanced binding (FIG. 7(C)).

These results demonstrate that the antibodies of the present technology or antigen binding fragments thereof, specifically bind to a polysialic acid antigen with high binding affinity. Accordingly, the immunoglobulin-related compositions disclosed herein are useful in methods for detecting polysialic acid with a high degree of polymerization (high DP polySia) in a sample as well as in methods for detecting tumors in a subject.

Example 9: Affinity Maturation of polySia-BsAb by Yeast Display

In an attempt to further improve the potency of polySia-BsAb, yeast display method was used to affinity mature scFv derived from P35 H1L2. Two screening methods were utilized, a direct method and a kinetic method (see Boder, E. T. and Wittrup, K. D, Biotechnol Prog., 1998, 14:55-62). In the direct method, yeast cells were incubated with antigen to equilibrium before sorting. In kinetic screening, yeast cells were stained with saturated amount of labeled antigen, followed by the non-labeled antigen added as a competitor. Based on sequence analysis, 6 clones were selected from the direct screen method, 8 clones were selected from the kinetic screen method, and one clone was selected from in silico design (D31R). Surface plasmon resonance (SPR) was performed on the selected clones.

The selected clones from the direct screen all contained mutations on D31 and W50, two of which have mutation on K38. The clones were subsequently ranked by dissociation constant ($K_D$, FIGS. 8(A)-8(B)). Clone DS54 exhibited the lowest $K_D$, more than 20-fold improvement on affinity when compared to the wild type clone. Clone DS47 had the smallest $K_{off}$, 15-times slower than the wild type clone. D31R has the fastest on rate, almost 250-fold faster compared to the wild type clone. Two more clones were made, DS47+D31R and DS54+D31R.

With respect to the selected clones from the kinetic screen (FIGS. 9(A)-9(B)), KS34 had a 3-fold improvement in affinity over the wild type clone. Clone KS2 had the slowest off rate, more than 6 times slower than the wild type clone. The clones from the kinetic screen had less conservation in terms of amino acids that are in common, even though most of them share the same mutation of D65C. The 6 clones were then converted back to the bispecific format.

Figures 10A, 10B:
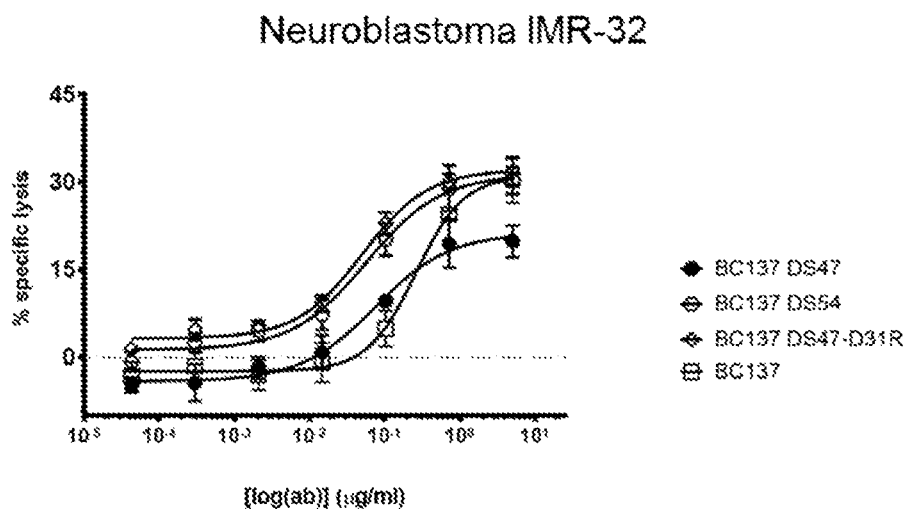
FIG. 10(A) shows TDCC assays of select BC137 clones on neuroblastoma IMR-32 cells.
FIG. 10(B) shows EC50 values of TDCC of select BC137 clones against melanoma M14, neuroblastoma IMR-32, and neuroblastoma SKNSH cells.

Three cell lines were used to compare the efficacy of selected clones in polySiaxCD3 BsAbs-redirected T-cell cytotoxicity. FIGS. 10(A)-10(B) demonstrate the efficacy of the selected clones in polySiaxCD3 BsABs-redirected T-cell cytotoxicity. The $EC_{50}$ values demonstrate that clones DS47 and DS54 were more effective than the wildtype BsAb.

Figure 11:
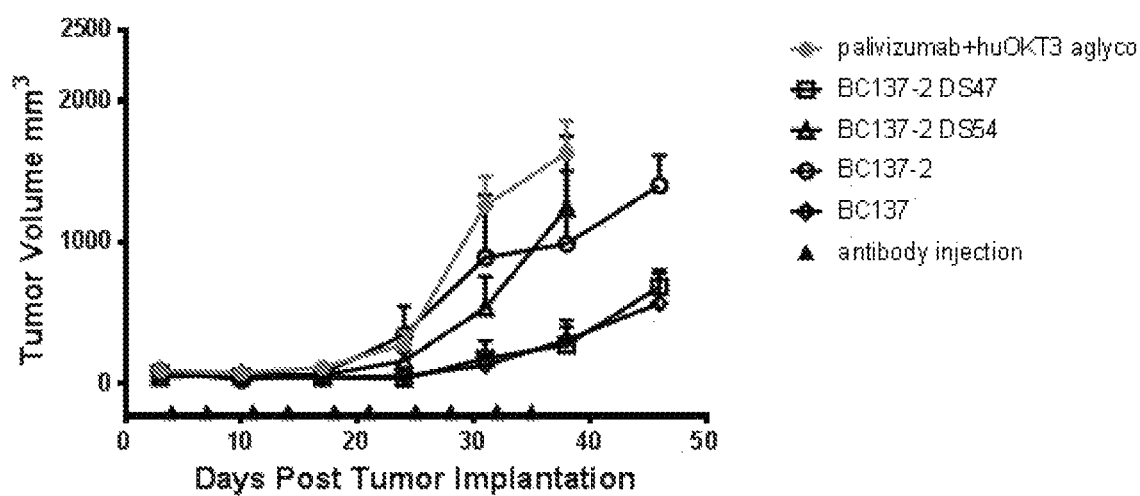
FIG. 11 shows the tumor volumes in a mouse xenograft study with neuroblastoma IMR-32 tumors treated with BC137 and select affinity matured variants.

In an in vivo therapy study, DKO mice were subcutaneously implanted with IMR-32 cells mixed (1:1) with PBMCs (unactivated from buffy coat). Treatment with BsAB was started on day 4 (100 μg, i.v., twice per week, five weeks) and tumor volume was measured each week. polySia-BsAB and clone47 exhibited anti-tumor effects compared to the control group (isotype control and aglycosylated huOKT3) and clone 54 (FIG. 11). On day 38, the average tumor size of the control group reached more than 1600 mm³, while the average tumor size of BC137-2 DS47 was less than 280 mm³ (83% reduction, p=0.004) and the average tumor size of BC137 was 310 mm³ (81% reduction, p=0.005).

These results demonstrate that the antibodies of the present technology or antigen binding fragments thereof, specifically bind to a polysialic acid antigen with high binding affinity. Accordingly, the immunoglobulin-related compositions disclosed herein are useful in methods for detecting polysialic acid with a high degree of polymerization (high DP polySia) in a sample as well as in methods for detecting tumors in a subject.

Figure 12:
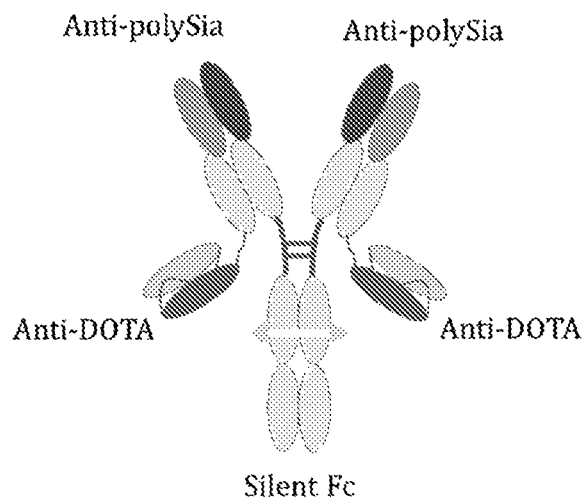
FIG. 12 shows a schematic diagram of polySiaxDOTA bispecific antibody in IgG-scFv format.

Example 10: Pre-Targeted Radioimmunotherapy Using polySia×DOTA Bispecific Antibody To determine if humanized P35 antibodies could be utilized for pre-target radioimmunotherapy, polySia×DOTA BsAb was generated using the IgG-scFv format, where a humanized anti-DOTA scFv (huC825) was fused to the C terminus of the light chain of a humanized P35 IgG1 with a silent Fc (FIG. 12). Using the P35 H1L2, the polySia×DOTA BsAb (BC163) was generated. A theranostic pretargeted radioimmunotherapy (PRIT) experiment was designed to test the potency of the polySia×DOTA BsAb.

Figure 13A:
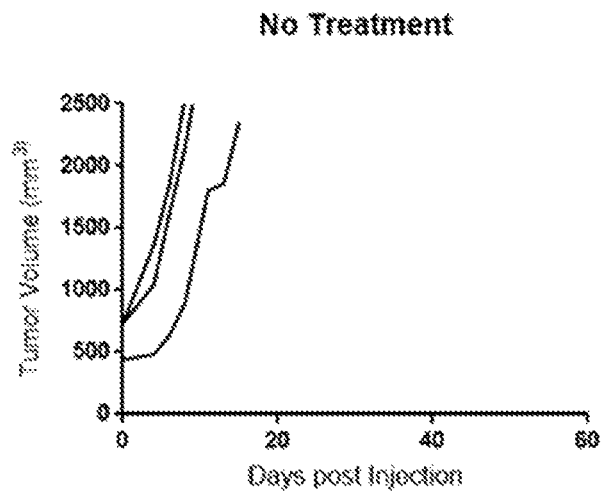
FIGS. 13(A)-13(E) shows the results of mouse xenograft studies with neuroblastoma IMR-32 tumors treated with (0, 0.25, 0.5, or 1 mg) BC137 polySiaxDOTA bispecific antibody BC163 and $^{177}$Lu-Bn-DOTA.
Figure 13B:
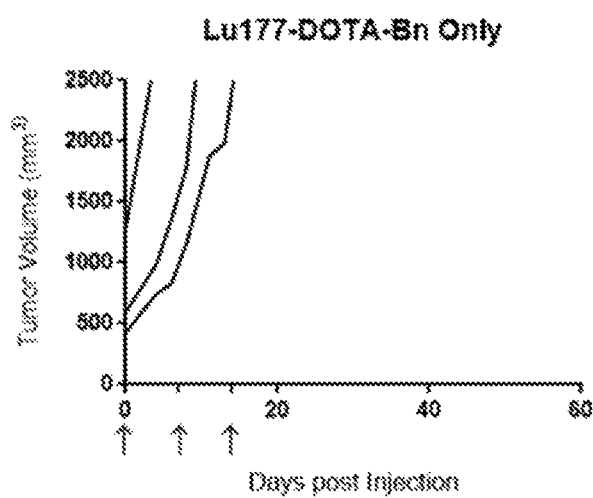
Figure 13C:
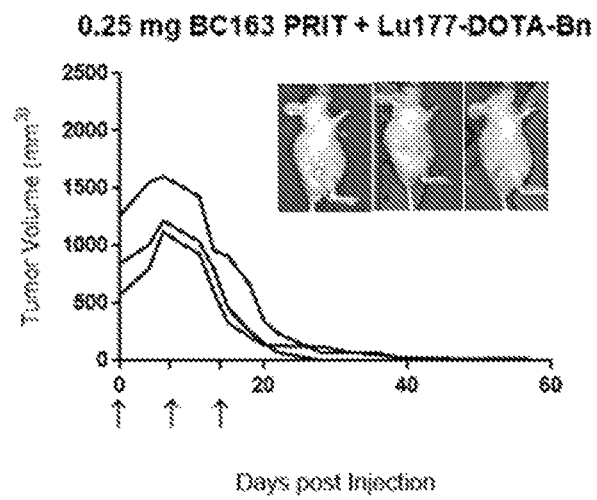
Figure 13D:
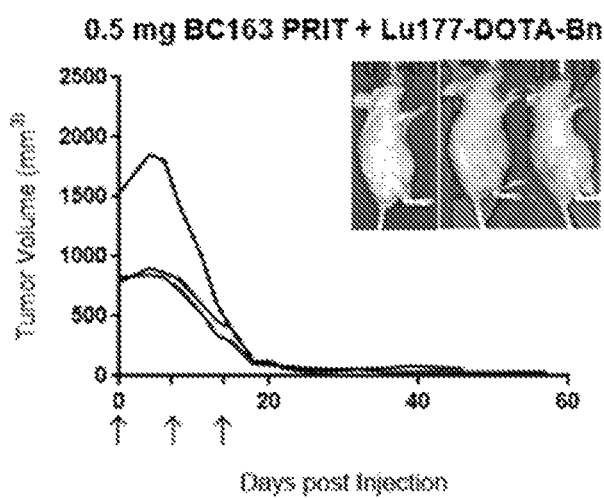
Figure 13E:
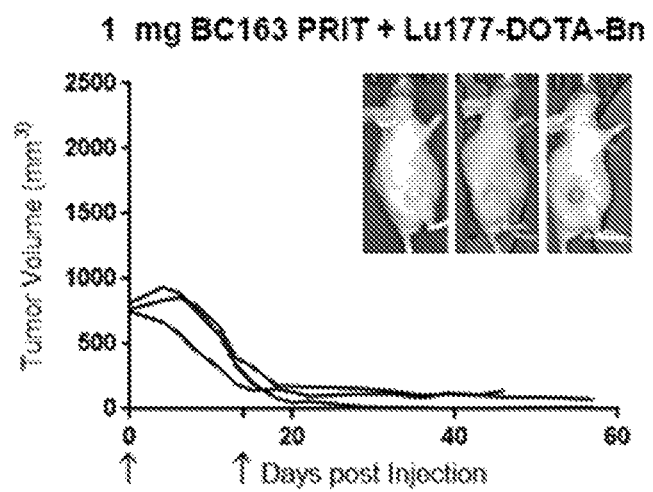

Groups of IMR-32 tumor-bearing nude mice with >500 mm³ tumor burden were injected with different doses of polySia×DOTA BsAb (0, 0.25 mg, 0.5 mg and 1 mg). The antibodies were injected once per week for three weeks (except the mice dosed with 1 mg BsAb, only two weeks). $^{177}$Lu-DOTA-Bn and clearing agent were injected 48 hours later. The mouse groups that received no treatment or $^{177}$Lu-DOTA-Bn exhibited rapid tumor growth (FIG. 13(A)-13(B)). The mouse groups that received 0.25, 0.5 or 1.0 mg of BC163 showed almost complete tumor ablation with no signs of toxicity (FIG. 13(C)-13(E)).

To further optimize and reduce potential immunogenicity in patients, eight additional heavy chain variants (87-88% human germline content) and three additional light chain variants (92% human germline content) were generated (FIG. 14(A)-14(B)).

Taken together, these results demonstrate that the antibodies or antigen binding fragments of the present technology can detect tumors, increase tumor sensitivity to radiation therapy and inhibit the progression of tumor growth and/or metastasis, and can be used to select patients for pre-targeted immunotherapy. Accordingly, the immunoglobulin-related compositions disclosed herein are useful in methods for detecting and treating a polySia-positive cancer in a subject in need thereof.

Example 11: Characterization of Therapeutic Effects of Re-Humanized Anti-polySia Antibodies Affinity values of the re-humanized anti-polySia antibodies to colominic acid were measured via Surface plasmon resonance. Re-humanized HP35 heavy chain (HC) variants 1-8 correspond to SEQ ID NOs: 74-81, respectively. See FIGS. 55-62. Re-humanized HP35 light chain (LC) variants 1-3 correspond to SEQ ID NOs: 82-84, respectively. See FIGS. 63-65. The results of these assays are shown in Table 2:

TABLE 2

| Samples | Ka1 (1/Ms) | kd1 (1/s) | ka2 (1/s) | kd2 (1/s) | KD (M) |
|---|---|---|---|---|---|
| HP35_LC2 + HC5 | 2.46E+06 | 3.89E−01 | 7.30E−03 | 1.37E−03 | 2.50E−08 |
| HP35_LC3 + HC7 | 3.72E+05 | 2.46E−01 | 3.01E−02 | 1.84E−03 | 3.80E−08 |
| HP35-chimeric | 1.01E+06 | 5.28E−01 | 2.47E−02 | 1.97E−03 | 3.86E−08 |
| HP35_LC2 + HC6 | 1.12E+06 | 6.76E−01 | 2.30E−02 | 1.58E−03 | 3.90E−08 |
| HP35_LC2 + HC8 | 1.23E+06 | 6.63E−01 | 2.34E−02 | 1.88E−03 | 4.01E−08 |
| HP35_LC2 + HC1 | 1.08E+06 | 5.90E−01 | 2.45E−02 | 1.96E−03 | 4.04E−08 |
| HP35_LC2 + HC7 | 1.49E+06 | 7.21E−01 | 1.86E−02 | 1.73E−03 | 4.12E−08 |
| HP35_LC3 + HC1 | 7.32E+05 | 8.59E−01 | 2.72E−02 | 1.04E−03 | 4.33E−08 |
| HP35_LC2 + HC3 | 1.44E+06 | 7.01E−01 | 1.74E−02 | 1.70E−03 | 4.33E−08 |
| HP35_LC3 + HC4 | 2.46E+05 | 2.04E−01 | 3.22E−02 | 1.86E−03 | 4.55E−08 |
| HP35_LC2 + HC4 | 1.32E+06 | 7.13E−01 | 1.91E−02 | 1.75E−03 | 4.56E−08 |
| HP35_LC3 + HC5 | 1.93E+06 | 7.37E−01 | 1.53E−02 | 2.10E−03 | 4.61E−08 |
| HP35_LC3 + HC8 | 2.35E+05 | 1.86E−01 | 3.22E−02 | 2.01E−03 | 4.65E−08 |
| HP35_LC3 + HC6 | 2.48E+05 | 1.97E−01 | 3.07E−02 | 2.03E−03 | 4.92E−08 |
| HP35_LC3 + HC3 | 2.78E+05 | 2.56E−01 | 3.23E−02 | 1.96E−03 | 5.28E−08 |
| HP35_LC2 + HC2 | 1.18E+06 | 7.23E−01 | 1.98E−02 | 1.90E−03 | 5.36E−08 |
| HP35_LC3 + HC2 | 2.42E+05 | 2.14E−01 | 2.95E−02 | 2.03E−03 | 5.68E−08 |
| HP35_LC1 + HC1 | 7.39E+05 | 4.67E−01 | 2.55E−02 | 2.58E−03 | 5.81E−08 |
| HP35_LC1 + HC5 | 2.16E+06 | 3.30E−01 | 3.68E−03 | 2.69E−03 | 6.46E−08 |
| HP35_LC1 + HC7 | 1.45E+06 | 7.28E−01 | 1.55E−02 | 2.69E−03 | 7.37E−08 |
| HP35_LC1 + HC3 | 1.41E+06 | 6.89E−01 | 1.40E−02 | 2.62E−03 | 7.69E−08 |
| HP35_LC1 + HC2 | 1.30E+06 | 6.64E−01 | 1.51E−02 | 2.88E−03 | 8.15E−08 |
| HP35_LC1 + HC6 | 1.33E+06 | 7.09E−01 | 1.52E−02 | 2.74E−03 | 8.16E−08 |
| HP35_LC1 + HC8 | 9.10E+05 | 5.87E−01 | 1.75E−02 | 3.01E−03 | 9.50E−08 |
| HP35_LC1 + HC4 | 1.28E+06 | 6.77E−01 | 1.41E−02 | 3.08E−03 | 9.51E−08 |

To evaluate the long-term stability of the re-humanized anti-polySia antibodies at accelerated storage conditions, antibody solutions were stored in a temperature-controlled incubator at 37° C. Samples were withdrawn at various times and analyzed for integrity by HPLC. As shown in Table 3, most of the re-humanized polySia antibodies were 76% to 95% intact after 3 weeks at 37° C.

TABLE 3

| Sample | starting | ending |
|---|---|---|
| HP35_LC3 + HC4 | 99.3 | 95.3 |
| HP35_LC3 + HC6 | 99.2 | 94.7 |
| HP35_LC3 + HC7 | 99.3 | 94.7 |
| HP35_LC3 + HC5 | 99.3 | 94.7 |
| HP35_LC3 + HC8 | 98.6 | 94.2 |
| HP35_LC3 + HC3 | 99.3 | 83.5 |
| HP35_LC2 + HC7 | 99.1 | 83.0 |
| HP35_LC2 + HC6 | 99.1 | 82.9 |
| HP35_LC3 + HC2 | 99.3 | 82.5 |
| HP35_LC3 + HC1 | 98.7 | 81.9 |
| HP35_LC2 + HC8 | 98.4 | 81.8 |
| HP35_LC1 + HC7 | 99.3 | 81.5 |
| HP35_LC2 + HC2 | 99.2 | 81.5 |
| HP35_LC1 + HC8 | 99.0 | 81.4 |
| HP35_LC2 + HC1 | 98.4 | 81.4 |
| HP35_LC1 + HC5 | 99.5 | 81.0 |
| HP35_LC1 + HC3 | 99.4 | 80.9 |

TABLE 3-continued

| Sample | starting | ending |
|---|---|---|
| HP35_LC1 + HC6 | 99.3 | 80.9 |
| HP35_LC1 + HC4 | 99.3 | 80.4 |
| HP35_LC2 + HC5 | 99.2 | 79.6 |
| HP35_LC2 + HC4 | 99.0 | 79.3 |
| HP35_LC2 + HC3 | 99.0 | 79.2 |
| HP35_LC1 + HC2 | 99.3 | 78.7 |
| HP35_chimeric | 98.8 | 78.5 |
| HP35_LC1 + HC1 | 97.8 | 76.0 |

Figure 67:
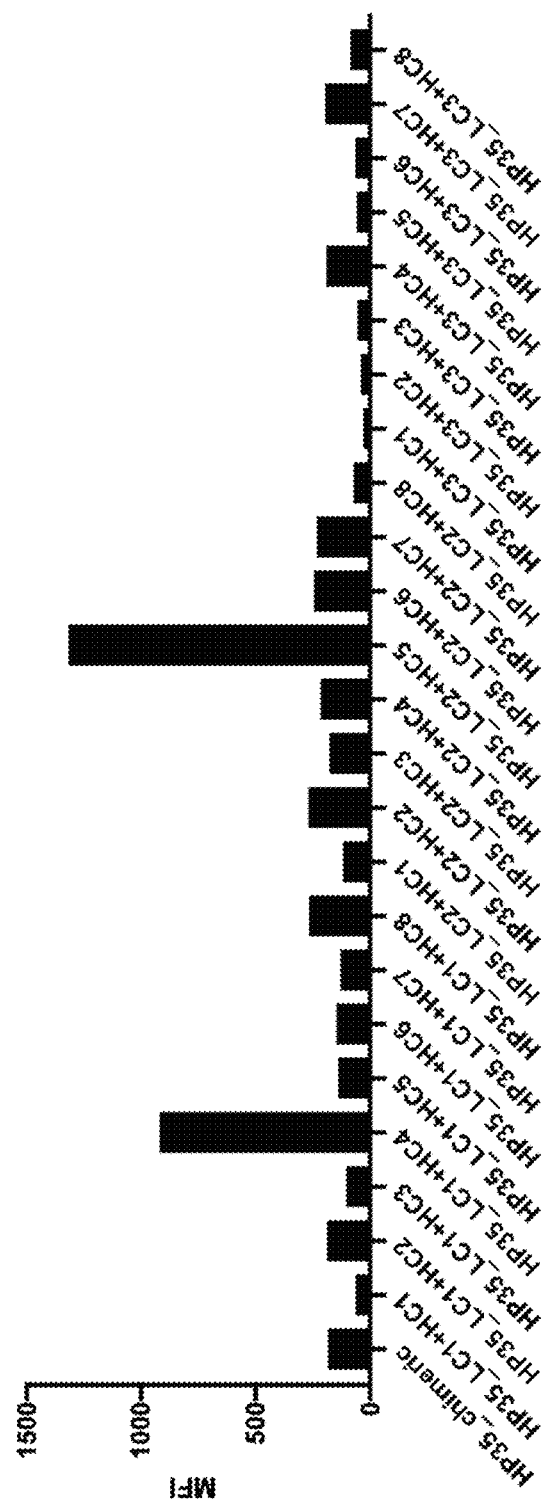
FIG. 67 shows the relative binding of the various re-humanized HP35 clones disclosed herein to M14 melanoma cell line (polysialic acid+) as determined by flow cytometry.

Binding of the various re-humanized anti-polySia antibodies of the present technology to M14 melanoma cells was assayed using flow cytometry. FIG. 67 shows the mean fluorescence intensity (MFI) of the rehumanized anti-polySia antibodies of the present technology. FIG. 68 shows a heatmap that compares the antigen binding properties and stability of the various re-humanized anti-polySia antibodies of the present technology relative to the chimeric HP35 polySia antibody.

These results demonstrate that the anti-polySia antibodies or antigen binding fragments of the present technology are useful in methods for detecting polysialic acid with a high degree of polymerization (high DP polySia) in a biological sample as well as methods for detecting a polySia-positive cancer in a subject in need thereof.

Example 12: Assessment of Therapeutic Effects of Re-Humanized Anti polySia Antibodies The eight additional heavy chain variants (87-88% human germline content) and three additional light chain variants (92% human germline content) shown in FIGS. 14(A) and 14(B), will be tested using the same PRIT experimental protocols described herein to test the potency of the polySiaxDOTA BsAbs. It is anticipated that tumor-bearing animals that receive the variant anti-polySia antibodies disclosed herein will exhibit a reduction in tumor volume.

These results will demonstrate that the immunoglobulin-related compositions disclosed herein are useful in methods for detecting and treating a polySia-positive cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An antibody or antigen binding fragment thereof comprising a heavy chain immunoglobulin variable domain ($V_H$) and a light chain immunoglobulin variable domain ($V_L$), wherein:

the $V_H$ comprises a $V_H$-CDR1 sequence of RYYIH (SEQ ID NO: 7), a $V_H$-CDR2 sequence of WIYPGSGNT-KYNEKFKG (SEQ ID NO: 2), and a $V_H$-CDR3 sequence of GGKFAMDY (SEQ ID NO:3), and the $V_L$ comprises a $V_L$-CDR1 sequence of RSSQSLVHSNG-NTYLY (SEQ ID NO: 4), a $V_L$-CDR2 sequence of RVSNRFS (SEQ ID NO: 5), and a $V_L$-CDR3 sequence of FQGTHVPYT (SEQ ID NO: 6), or the $V_H$ comprises a $V_H$-CDR1 sequence of GYYIH (SEQ ID NO: 8), a $V_H$-CDR2 sequence of SIYPGSGNT-KYNEKFKG (SEQ ID NO: 10), and a $V_H$-CDR3 sequence of GGKFAMDY (SEQ ID NO:3), and the $V_L$ comprises a $V_L$-CDR1 sequence of RSSQSLVHSNG-NTYLY (SEQ ID NO: 4), a $V_L$-CDR2 sequence of RVSNRFS (SEQ ID NO: 5), and a $V_L$-CDR3 sequence of FQGTHVPYT (SEQ ID NO: 6), or the $V_H$ comprises a $V_H$-CDR1 sequence of NYYIH (SEQ ID NO: 9), a $V_H$-CDR2 sequence of RIYPGSGNT-KYNEKFKG (SEQ ID NO: 11), and a $V_H$-CDR3 sequence of GGKFAMDY (SEQ ID NO:3), and the $V_L$ comprises a $V_L$-CDR1 sequence of RSSQSLVHSNG-NTYLY (SEQ ID NO: 4), a $V_L$-CDR2 sequence of RVSNRFS (SEQ ID NO: 5), and a $V_L$-CDR3 sequence of FQGTHVPYT (SEQ ID NO: 6), or the $V_H$ comprises a $V_H$-CDR1 sequence of GYYIH (SEQ ID NO: 8), a $V_H$-CDR2 sequence of CIYPGSGNT-KYNEKFKG (SEQ ID NO: 12), and a $V_H$-CDR3 sequence of GGKFAMDY (SEQ ID NO:3), and the $V_L$ comprises a $V_L$-CDR1 sequence of RSSQSLVHSNG- NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of RIYPGSGNT-KYNEKFKG (SEQ ID NO: 11), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of NYYIH (SEQ ID NO: 9), a V$_H$-CDR2 sequence of CIYPGSGNT-KYNEKFKG (SEQ ID NO: 12), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of WIYPGSGNT-KYNEKFEG (SEQ ID NO: 13), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYI (SEQ ID NO: 21), or the V$_H$ comprises a V$_H$-CDR1 sequence of DYYIH (SEQ ID NO: 1), a V$_H$-CDR2 sequence of CIYPGSGNT-KYNEKFKG (SEQ ID NO: 12), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of WIYPGSGNT-KYNEKFKG (SEQ ID NO: 2), and a V$_H$-CDR3 sequence of GGKFAMDY (SEQ ID NO:3), and the V$_L$ comprises a V$_L$-CDR1 sequence of RSSQSLVHSNGKTYLY (SEQ ID NO: 20), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of WIYPGSGNT-KYNEKFKG (SEQ ID NO: 2), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHEPYT (SEQ ID NO: 22), or the V$_H$ comprises a V$_H$-CDR1 sequence of RYYIH (SEQ ID NO: 7), a V$_H$-CDR2 sequence of RIYPGSGNT-KYNEKFKG (SEQ ID NO: 11), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of WIYPGSGNT-KYNQKFQG (SEQ ID NO: 14), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of WIYPGSGNT-KYSQKFQG (SEQ ID NO: 15), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of WIYPGSGNT-KYSEKFQG (SEQ ID NO: 16), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6), or the V$_H$ comprises a V$_H$-CDR1 sequence of DYYIH (SEQ ID NO: 1), a V$_H$-CDR2 sequence of WIYPGSGNT-KYSQKFKG (SEQ ID NO: 18), and a V$_H$-CDR3 sequence of GGKFAMDY (SEQ ID NO:3), and the V$_L$ comprises a V$_L$-CDR1 sequence of RSSQSLVHSNG-NTYLY (SEQ ID NO: 4), a V$_L$-CDR2 sequence of RVSNRFS (SEQ ID NO: 5), and a V$_L$-CDR3 sequence of FQGTHVPYT (SEQ ID NO: 6).

2. The antibody or antigen binding fragment of claim 1, further comprising a Fc domain of an isotype selected from the group consisting of IgG1, IgG2, IgG3, IgG4, IgA1, IgA2, IgM, IgD, and IgE, wherein
   IgG1 comprises one or more amino acid substitutions selected from the group consisting of N297A and K322A; or
   IgG4 comprises a S228P mutation, or
   the antibody lacks α-1,6-fucose modifications.

3. The antibody or antigen binding fragment of claim 1, wherein the antibody or antigen binding fragment binds to a polysialic acid with a high degree of polymerization (high DP polySia), or
   wherein the antibody is a monoclonal antibody, a chimeric antibody, or a humanized antibody, or the antigen binding fragment is selected from the group consisting of Fab, F(ab')$_2$, Fab', scF$_v$, and F$_v$, or
   wherein the antibody or antigen binding fragment is a bispecific antibody that binds to T cells, B-cells, myeloid cells, plasma cells, mast-cells, CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten, or
   wherein the antibody or antigen binding fragment recruits T cells for T cell-dependent cellular cytotoxicity (TDCC) against polySia-expressing tumor cells, wherein the polySia-expressing tumor cells are resistant to polySia-specific antibody-dependent cell-mediated cytotoxicity (ADCC).

4. An antibody or antigen binding fragment thereof comprising
   a heavy chain immunoglobulin variable domain sequence and a light chain immunoglobulin variable domain sequence that are 100% identical to the heavy chain immunoglobulin variable domain sequence and the light chain immunoglobulin variable domain sequence present in
   a) SEQ ID NO: 81 and SEQ ID NO: 84 (rehumanized P35H8L3);

b) SEQ ID NO: 25 and SEQ ID NO: 28 (humanized P35 H1L2);
c) SEQ ID NO: 25 and SEQ ID NO: 27 (humanized P35 H1L1);
d) SEQ ID NO: 26 and SEQ ID NO: 28 (humanized P35 H2L2);
e) SEQ ID NO: 26 and SEQ ID NO: 27 (humanized P35 H2L1);
f) SEQ ID NO: 48 and SEQ ID NO: 49 (BC137);
g) SEQ ID NO: 51 and SEQ ID NO: 52 (BC137 KS2);
h) SEQ ID NO: 53 and SEQ ID NO: 54 (BC137 KS34);
i) SEQ ID NO: 55 and SEQ ID NO: 49 (BC137 DS47);
j) SEQ ID NO: 56 and SEQ ID NO: 49 (BC137 DS54);
k) SEQ ID NO: 57 and SEQ ID NO: 49 (BC137 DS47 D31R);
l) SEQ ID NO: 58 and SEQ ID NO: 49 (BC137 DS54 D31R);
m) SEQ ID NO: 55 and SEQ ID NO: 50 (BC137-2 DS47);
n) SEQ ID NO: 56 and SEQ ID NO: 50 (BC137-2 DS54);
o) SEQ ID NO: 59 and SEQ ID NO: 60 (BC163),
p) SEQ ID NO: 74 and SEQ ID NO: 82 (rehumanized P35H1L1);
q) SEQ ID NO: 75 and SEQ ID NO: 82 (rehumanized P35H2L1);
r) SEQ ID NO: 76 and SEQ ID NO: 82 (rehumanized P35H3L1);
s) SEQ ID NO: 77 and SEQ ID NO: 82 (rehumanized P35H4L1);
t) SEQ ID NO: 78 and SEQ ID NO: 82 (rehumanized P35H5L1);
u) SEQ ID NO: 79 and SEQ ID NO: 82 (rehumanized P35H6L1);
v) SEQ ID NO: 80 and SEQ ID NO: 82 (rehumanized P35H7L1);
w) SEQ ID NO: 81 and SEQ ID NO: 82 (rehumanized P35H8L1);
x) SEQ ID NO: 74 and SEQ ID NO: 83 (rehumanized P35H1L2);
y) SEQ ID NO: 75 and SEQ ID NO: 83 (rehumanized P35H2L2);
z) SEQ ID NO: 76 and SEQ ID NO: 83 (rehumanized P35H3L2);
aa) SEQ ID NO: 77 and SEQ ID NO: 83 (rehumanized P35H4L2);
bb) SEQ ID NO: 78 and SEQ ID NO: 83 (rehumanized P35H5L2);
cc) SEQ ID NO: 79 and SEQ ID NO: 83 (rehumanized P35H6L2);
dd) SEQ ID NO: 80 and SEQ ID NO: 83 (rehumanized P35H7L2);
ee) SEQ ID NO: 81 and SEQ ID NO: 83 (rehumanized P35H8L2);
ff) SEQ ID NO: 74 and SEQ ID NO: 84 (rehumanized P35H1L3);
gg) SEQ ID NO: 75 and SEQ ID NO: 84 (rehumanized P35H2L3);
hh) SEQ ID NO: 76 and SEQ ID NO: 84 (rehumanized P35H3L3);
ii) SEQ ID NO: 77 and SEQ ID NO: 84 (rehumanized P35H4L3);
jj) SEQ ID NO: 78 and SEQ ID NO: 84 (rehumanized P35H5L3);
kk) SEQ ID NO: 79 and SEQ ID NO: 84 (rehumanized P35H6L3); and
ll) SEQ ID NO: 80 and SEQ ID NO: 84 (rehumanized P35H7L3), respectively.

5. A composition comprising the antibody or antigen binding fragment of claim 4 and a pharmaceutically-acceptable carrier.

6. The composition of claim 5, wherein the antibody or antigen binding fragment is conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

7. The antibody of claim 4, wherein the antibody is a bispecific antibody that binds to a radiolabeled DOTA hapten and a high DP polySia.

8. A method for detecting solid tumors in a subject in need thereof comprising
   (a) administering to the subject an effective amount of a complex comprising a radiolabeled DOTA hapten and the bispecific antibody of claim 7, wherein the complex is configured to localize to solid tumor expressing high DP polySia; and
   (b) detecting the presence of solid tumors in the subject by detecting radioactive levels emitted by the complex that are higher than a reference value.

9. A method for selecting a subject for pretargeted radioimmunotherapy comprising
   (a) administering to the subject an effective amount of a complex comprising a radiolabeled DOTA hapten and the bispecific antibody of claim 7, wherein the complex is configured to localize to solid tumor expressing high DP polySia;
   (b) detecting radioactive levels emitted by the complex; and
   (c) selecting the subject for pretargeted radioimmunotherapy when the radioactive levels emitted by the complex are higher than a reference value.

10. A method for treating cancer or increasing tumor sensitivity to radiation therapy in a subject in need thereof comprising administering to the subject an effective amount of a complex comprising a radiolabeled DOTA hapten and the bispecific antibody of claim 7, wherein the complex is configured to localize to tumor expressing high DP polySia.

11. A method for treating cancer or increasing tumor sensitivity to radiation therapy in a subject in need thereof comprising
   (a) administering an effective amount of the bispecific antibody of claim 7, wherein the bispecific antibody is configured to localize to tumor expressing high DP polySia; and
   (b) administering an effective amount of a radiolabeled-DOTA hapten to the subject, wherein the radiolabeled-DOTA hapten is configured to bind to the bispecific antibody, wherein the method further comprising administering an effective amount of a clearing agent to the subject prior to administration of the radiolabeled-DOTA hapten.

12. An antibody comprising a heavy chain (HC) amino acid sequence and a light chain (LC) amino acid sequence selected from the group consisting of:
   a) SEQ ID NO: 81 and SEQ ID NO: 84 (rehumanized P35H8L3);
   b) SEQ ID NO: 25 and SEQ ID NO: 28 (humanized P35 H1L2);
   c) SEQ ID NO: 25 and SEQ ID NO: 27 (humanized P35 H1L1);
   d) SEQ ID NO: 26 and SEQ ID NO: 28 (humanized P35 H2L2);

e) SEQ ID NO: 26 and SEQ ID NO: 27 (humanized P35 H2L1);
f) SEQ ID NO: 48 and SEQ ID NO: 49 (BC137);
g) SEQ ID NO: 51 and SEQ ID NO: 52 (BC137 KS2);
h) SEQ ID NO: 53 and SEQ ID NO: 54 (BC137 KS34);
i) SEQ ID NO: 55 and SEQ ID NO: 49 (BC137 DS47);
j) SEQ ID NO: 56 and SEQ ID NO: 49 (BC137 DS54);
k) SEQ ID NO: 57 and SEQ ID NO: 49 (BC137 DS47 D31R);
l) SEQ ID NO: 58 and SEQ ID NO: 49 (BC137 DS54 D31R);
m) SEQ ID NO: 55 and SEQ ID NO: 50 (BC137-2 DS47);
n) SEQ ID NO: 56 and SEQ ID NO: 50 (BC137-2 DS54);
o) SEQ ID NO: 59 and SEQ ID NO: 60 (BC163),
p) SEQ ID NO: 74 and SEQ ID NO: 82 (rehumanized P35H1L1);
q) SEQ ID NO: 75 and SEQ ID NO: 82 (rehumanized P35H2L1);
r) SEQ ID NO: 76 and SEQ ID NO: 82 (rehumanized P35H3L1);
s) SEQ ID NO: 77 and SEQ ID NO: 82 (rehumanized P35H4L1);
t) SEQ ID NO: 78 and SEQ ID NO: 82 (rehumanized P35H5L1);
u) SEQ ID NO: 79 and SEQ ID NO: 82 (rehumanized P35H6L1);
v) SEQ ID NO: 80 and SEQ ID NO: 82 (rehumanized P35H7L1);
w) SEQ ID NO: 81 and SEQ ID NO: 82 (rehumanized P35H8L1);
x) SEQ ID NO: 74 and SEQ ID NO: 83 (rehumanized P35H1L2);
y) SEQ ID NO: 75 and SEQ ID NO: 83 (rehumanized P35H2L2);
z) SEQ ID NO: 76 and SEQ ID NO: 83 (rehumanized P35H3L2);
aa) SEQ ID NO: 77 and SEQ ID NO: 83 (rehumanized P35H4L2);
bb) SEQ ID NO: 78 and SEQ ID NO: 83 (rehumanized P35H5L2);
cc) SEQ ID NO: 79 and SEQ ID NO: 83 (rehumanized P35H6L2);
dd) SEQ ID NO: 80 and SEQ ID NO: 83 (rehumanized P35H7L2);
ee) SEQ ID NO: 81 and SEQ ID NO: 83 (rehumanized P35H8L2);
ff) SEQ ID NO: 74 and SEQ ID NO: 84 (rehumanized P35H1L3);
gg) SEQ ID NO: 75 and SEQ ID NO: 84 (rehumanized P35H2L3);
hh) SEQ ID NO: 76 and SEQ ID NO: 84 (rehumanized P35H3L3);
ii) SEQ ID NO: 77 and SEQ ID NO: 84 (rehumanized P35H4L3);
jj) SEQ ID NO: 78 and SEQ ID NO: 84 (rehumanized P35H5L3);
kk) SEQ ID NO: 79 and SEQ ID NO: 84 (rehumanized P35H6L3); and
ll) SEQ ID NO: 80 and SEQ ID NO: 84 (rehumanized P35H7L3), respectively.

13. A recombinant nucleic acid encoding the antibody of claim 12.

14. The recombinant nucleic acid of claim 13, wherein the recombinant nucleic acid comprises any of SEQ ID NOs: 92-108.

15. A host cell or vector comprising the recombinant nucleic acid sequence of claim 13.

16. A method for treating a polysialic acid (polySia) associated cancer in a subject in need thereof, comprising administering to the subject an effective amount of the antibody of claim 12 wherein the antibody specifically binds to polySia, wherein the polySia associated cancer is small cell or non-small cell lung cancer, neuroblastoma, pancreatic cancer, pituitary tumors, Wilm's tumor, rhabdomyosarcoma, glioblastoma, breast cancer, or acute myeloid leukemia.

17. The method of 16, wherein the antibody is administered to the subject separately, sequentially or simultaneously with an additional therapeutic agent.

18. A method for detecting a tumor in a subject in vivo comprising
  (a) administering to the subject an effective amount of an antibody of claim 12, wherein the antibody is configured to localize to a tumor expressing polysialic acid with a high degree of polymerization (high DP polySia) and is labeled with a radioisotope; and
  (b) detecting the presence of a tumor in the subject by detecting radioactive levels emitted by the antibody that are higher than a reference value, wherein
  the subject is diagnosed with or is suspected of having cancer, or
  the radioactive levels emitted by the antibody are detected using positron emission tomography or single photon emission computed tomography.

19. The method of claim 18, further comprising administering to the subject an effective amount of an immunoconjugate comprising the antibody of claim 9 conjugated to a radionuclide.

20. The method of claim 19, wherein the radionuclide is an alpha particle-emitting isotope, a beta particle-emitting isotope, an Auger-emitter, or any combination thereof, wherein the beta particle-emitting isotope is selected from the group consisting of $^{86}$Y, $^{90}$Y, $^{89}$Sr, $^{165}$Dy, $^{186}$Re, $^{188}$Re, $^{177}$Lu, and $^{67}$Cu.

* * * * *

SEQUENCE LISTING

```
<160> NUMBER OF SEQ ID NOS: 112

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Tyr Ile His
1               5

<210> SEQ ID NO 2
<211> LENGTH: 17
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 2

Trp Ile Tyr Pro Gly Ser Gly Asn Thr Lys Tyr Asn Glu Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Lys Phe Ala Met Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Ser Gln Ser Leu Val His Ser Asn Gly Asn Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Gly Thr His Val Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Tyr Tyr Ile His
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Tyr Tyr Ile His
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Tyr Tyr Ile His
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ile Tyr Pro Gly Ser Gly Asn Thr Lys Tyr Asn Glu Lys Phe Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ile Tyr Pro Gly Ser Gly Asn Thr Lys Tyr Asn Glu Lys Phe Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ile Tyr Pro Gly Ser Gly Asn Thr Lys Tyr Asn Glu Lys Phe Lys
1               5                   10                  15

Gly

```
<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ile Tyr Pro Gly Ser Gly Asn Thr Lys Tyr Asn Glu Lys Phe Glu
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Ile Tyr Pro Gly Ser Gly Asn Thr Lys Tyr Asn Gln Lys Phe Gln
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ile Tyr Pro Gly Ser Gly Asn Thr Lys Tyr Ser Gln Lys Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Tyr Pro Gly Ser Gly Asn Thr Lys Tyr Ser Glu Lys Phe Gln
1               5                   10                  15

Gly

<210> SEQ ID NO 17
<211> LENGTH: 340
<212> TYPE: PRT
<213> ORGANISM: Homo sapiens

<400> SEQUENCE: 17

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45
```

```
Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Pro Cys Cys His Pro
                100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
        130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
                260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
        290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Ile Tyr Pro Gly Ser Gly Asn Thr Lys Tyr Ser Gln Lys Phe Lys
1               5                   10                  15

Gly

<210> SEQ ID NO 19
<211> LENGTH: 106
<212> TYPE: PRT
<213> ORGANISM: Homo sapiens
```

<400> SEQUENCE: 19

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ser Ser Gln Ser Leu Val His Ser Asn Gly Lys Thr Tyr Leu Tyr
1               5                   10                  15

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Gln Gly Thr His Val Pro Tyr Ile
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Gln Gly Thr His Glu Pro Tyr Thr
1               5

<210> SEQ ID NO 23
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ile Gln Leu Gln Gln Ser Gly Pro Glu Leu Val Arg Pro Gly Ala
1               5                   10                  15

```
Ser Val Lys Ile Ser Cys Lys Ala Ser Gly Tyr Thr Phe Thr Asp Tyr
             20                  25                  30

Tyr Ile His Trp Val Lys Gln Arg Pro Gly Glu Gly Leu Glu Trp Ile
             35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
            435                 440                 445

<210> SEQ ID NO 24
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Gly Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 25
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

```
Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 26
<211> LENGTH: 447
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 26

```
Gln Ile Gln Leu Val Gln Ser Gly Pro Glu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Ser Gly Asn Thr Lys Tyr Asn Glu Lys Phe
    50                  55                  60

Lys Gly Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 27
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Val Val Met Thr Gln Ser Pro Leu Ser Leu Pro Val Thr Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 28
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30
```

Asn Gly Asn Thr Tyr Leu Tyr Trp Tyr Leu Gln Lys Pro Gly Gln Ser
            35                  40                  45

Pro Lys Pro Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                 85                  90                  95

Thr His Val Pro Tyr Thr Phe Gly Gln Gly Thr Arg Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 29
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ile Gln Leu Gln Gln Ser Gly Pro Glu Val Val Lys Pro Gly Ala
 1               5                  10                  15

Ser Val Lys Ile Ser Cys Lys Ala Ser Gly Tyr Thr Phe Thr Arg Tyr
                 20                  25                  30

Tyr Ile His Trp Val Lys Gln Arg Pro Gly Gln Gly Leu Glu Trp Ile
             35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Tyr Ile His Trp Val Lys Gln Arg Pro Gly Gln Gly Leu Glu Trp Ile
        35                  40                  45

Gly Ser Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys

```
                    85                  90                  95

Ala Arg Gly Gly Lys Phe Ala Met Asp Tyr Trp Gly Gln Gly Thr Leu
                100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asn Tyr
                20                  25                  30

Tyr Ile His Trp Val Met Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
        50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
                100                 105                 110

Val Thr Val Ser Ser
        115

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Tyr Ile His Trp Val Lys Gln Arg Pro Gly Gln Gly Leu Glu Trp Ile
            35                  40                  45

Gly Cys Ile Tyr Pro Gly Ser Gly Asn Thr Lys Tyr Asn Glu Lys Phe
        50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
                100                 105                 110

Val Thr Val Ser Ser
        115
```

```
<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Met Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
        50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser
        115

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asn Tyr
                20                  25                  30

Tyr Ile His Trp Val Lys Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
        50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser
        115

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Cys Ile Tyr Pro Gly Ser Gly Asn Thr Lys Tyr Asn Glu Lys Phe
50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
                100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
50                  55                  60

Glu Gly Lys Ala Thr Leu Thr Val Asp Thr Ser Ala Ser Thr Ala His
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
                100                 105                 110

Val Thr Val Ser Ser
        115

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

```
Pro Lys Pro Leu Ile Tyr Arg Val Ser Asn Arg Phe Ser Gly Val Pro
        50                  55                  60

Cys Arg Phe Ser Gly Ser Gly Ser Gly Thr Asp Phe Thr Leu Lys Ile
 65                  70                  75                  80

Ser Arg Val Glu Thr Glu Asp Val Gly Val Tyr Phe Cys Phe Gln Gly
                 85                  90                  95

Thr His Val Pro Tyr Ile Phe Gly Gln Gly Thr Arg Leu Glu Ile Lys
                100                 105                 110

Arg

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ile Gln Leu Gln Gln Ser Gly Pro Glu Val Val Lys Pro Gly Ala
 1               5                  10                  15

Ser Val Lys Ile Ser Cys Lys Ala Ser Gly Tyr Thr Phe Thr Asp Tyr
                 20                  25                  30

Tyr Ile His Trp Val Lys Gln Arg Pro Gly Gln Gly Leu Glu Trp Ile
             35                  40                  45

Gly Cys Ile Tyr Pro Gly Ser Gly Asn Thr Lys Tyr Asn Glu Lys Phe
 50                  55                  60

Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
                100                 105                 110

Val Thr Val Ser Ser
            115

<210> SEQ ID NO 39
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
                 20                  25                  30

Asn Gly Asn Thr Tyr Leu Tyr Trp Tyr Leu Gln Lys Pro Gly Gln Ser
             35                  40                  45

Pro Lys Pro Leu Ile Tyr Arg Val Ser Asn Arg Phe Ser Cys Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                 85                  90                  95
```

```
Thr His Val Pro Tyr Thr Phe Gly Gln Gly Thr Arg Leu Glu Ile Lys
            100                 105                 110

Arg

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Cys Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser
        115

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Gly Lys Thr Tyr Leu Tyr Trp Tyr Leu Gln Lys Pro Gly Gln Ser
            35                  40                  45

Pro Lys Pro Leu Ile Tyr Arg Val Ser Asn Arg Phe Ser Cys Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gln Gly Thr Arg Leu Glu Ile Lys
            100                 105                 110

Arg

<210> SEQ ID NO 42
<211> LENGTH: 117
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 42

Gln Ile Gln Leu Gln Gln Ser Gly Pro Glu Val Val Lys Pro Gly Ala
1               5                   10                  15

Ser Val Lys Ile Ser Cys Lys Ala Ser Ala Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser
        115

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Cys Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gln Gly
                85                  90                  95

Thr His Val Pro Tyr Thr Phe Gly Gln Gly Thr Arg Leu Glu Ile Lys
            100                 105                 110

Arg

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
```

```
                    20                  25                  30

Asn Gly Asn Thr Tyr Leu Tyr Trp Tyr Leu Gln Lys Pro Gly Lys Ser
            35                  40                  45

Pro Lys Pro Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Lys Asp Val Gly Val Tyr Phe Cys Phe Gln Gly
                85                  90                  95

Thr His Val Pro Tyr Thr Phe Gly Gln Gly Thr Arg Leu Glu Ile Lys
                100                 105                 110

Arg

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Val Val Met Thr Gln Ser Pro Leu Ser Leu Pro Val Thr Leu Gly
1               5                   10                  15

Gln Pro Val Ser Ile Ser Cys Arg Ser Ser Gln Ser Leu Val His Ser
                20                  25                  30

Asn Gly Asn Thr Tyr Leu Tyr Trp Tyr Leu Gln Lys Pro Gly Gln Ser
            35                  40                  45

Pro Lys Pro Leu Ile Tyr Arg Val Ser Asn Arg Phe Ser Gly Val Pro
        50                  55                  60

Cys Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Glu Pro Tyr Thr Phe Gly Gln Gly Thr Arg Leu Glu Ile Lys
                100                 105                 110

Arg

<210> SEQ ID NO 46
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Val Ser Thr Ala Tyr
65                  70                  75                  80
```

```
Met Glu Leu Ser Ser Leu Thr Ser Glu Asp Asn Ala Val Tyr Phe Cys
                 85                  90                  95

Ala Arg Gly Gly Lys Phe Ala Met Asp Tyr Trp Gly Gln Gly Thr Leu
            100                 105                 110

Val Thr Val Ser Ser
            115
```

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Cys Arg Tyr Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gln Gly Thr Arg Leu Glu Ile Lys
            100                 105                 110

Arg
```

<210> SEQ ID NO 48
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
```

```
            130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
                275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
                435                 440                 445

<210> SEQ ID NO 49
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Gly Asn Thr Tyr Leu Tyr Trp Tyr Leu Gln Lys Pro Gly Gln Ser
            35                  40                  45
```

```
Pro Lys Pro Leu Ile Tyr Arg Val Ser Asn Arg Phe Ser Gly Val Pro
    50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Phe Cys Phe Gln Gly
                85                  90                  95

Thr His Val Pro Tyr Thr Phe Gly Gln Gly Thr Arg Leu Glu Ile Lys
            100             105             110

Arg Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
130             135                 140

Tyr Pro Arg Glu Ala Lys Val Gln Trp Lys Val Asp Asn Ala Leu Gln
145             150                 155                 160

Ser Gly Asn Ser Gln Glu Ser Val Thr Glu Gln Asp Ser Lys Asp Ser
                165             170                 175

Thr Tyr Ser Leu Ser Ser Thr Leu Thr Leu Ser Lys Ala Asp Tyr Glu
            180             185                 190

Lys His Lys Val Tyr Ala Cys Glu Val Thr His Gln Gly Leu Ser Ser
            195             200             205

Pro Val Thr Lys Ser Phe Asn Arg Gly Glu Cys Thr Ser Gly Gly Gly
        210             215                 220

Gly Ser Gly Gly Gly Gly Ser Gly Gly Gly Gly Ser Gln Val Gln Leu
225             230             235                 240

Val Gln Ser Gly Gly Gly Val Val Gln Pro Gly Arg Ser Leu Arg Leu
            245             250                 255

Ser Cys Lys Ala Ser Gly Tyr Thr Phe Thr Arg Tyr Thr Met His Trp
        260             265             270

Val Arg Gln Ala Pro Gly Lys Cys Leu Glu Trp Ile Gly Tyr Ile Asn
        275             280             285

Pro Ser Arg Gly Tyr Thr Asn Tyr Asn Gln Lys Phe Lys Asp Arg Phe
    290             295             300

Thr Ile Ser Arg Asp Asn Ser Lys Asn Thr Ala Phe Leu Gln Met Asp
305             310             315                 320

Ser Leu Arg Pro Glu Asp Thr Gly Val Tyr Phe Cys Ala Arg Tyr Tyr
            325             330             335

Asp Asp His Tyr Ser Leu Asp Tyr Trp Gly Gln Gly Thr Pro Val Thr
            340             345             350

Val Ser Ser Gly Gly Gly Gly Ser Gly Gly Gly Gly Ser Gly Gly Gly
            355             360             365

Gly Ser Gly Gly Gly Gly Ser Gly Gly Gly Gly Ser Gly Gly Gly Gly
    370             375             380

Ser Asp Ile Gln Met Thr Gln Ser Pro Ser Ser Leu Ser Ala Ser Val
385             390             395                 400

Gly Asp Arg Val Thr Ile Thr Cys Ser Ala Ser Ser Ser Val Ser Tyr
            405             410             415

Met Asn Trp Tyr Gln Gln Thr Pro Gly Lys Ala Pro Lys Arg Trp Ile
            420             425             430

Tyr Asp Thr Ser Lys Leu Ala Ser Gly Val Pro Ser Arg Phe Ser Gly
            435             440             445

Ser Gly Ser Gly Thr Asp Tyr Thr Phe Thr Ile Ser Ser Leu Gln Pro
    450             455             460

Glu Asp Ile Ala Thr Tyr Tyr Cys Gln Gln Trp Ser Ser Asn Pro Phe
```

```
            465                 470                 475                 480
        Thr Phe Gly Cys Gly Thr Lys Leu Gln Ile Thr Arg
                        485                 490

<210> SEQ ID NO 50
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Ser Gly Gly Gly
    210                 215                 220

Gly Ser Gly Gly Gly Ser Gly Gly Gly Ser Gln Val Gln Leu
225                 230                 235                 240

Val Gln Ser Gly Gly Val Val Gln Pro Gly Arg Ser Leu Arg Leu
            245                 250                 255

Ser Cys Lys Ala Ser Gly Tyr Thr Phe Thr Arg Tyr Thr Met His Trp
        260                 265                 270

Val Arg Gln Ala Pro Gly Lys Gly Leu Glu Trp Ile Gly Tyr Ile Asn
    275                 280                 285

Pro Ser Arg Gly Tyr Thr Asn Tyr Asn Gln Lys Phe Lys Asp Arg Phe
    290                 295                 300

Thr Ile Ser Arg Asp Asn Ser Lys Asn Thr Ala Phe Leu Gln Met Asp
305                 310                 315                 320

Ser Leu Arg Pro Glu Asp Thr Gly Val Tyr Phe Cys Ala Arg Tyr Tyr
                325                 330                 335
```

Asp Asp His Tyr Ser Leu Asp Tyr Trp Gly Gln Gly Thr Pro Val Thr
                340                 345                 350

Val Ser Ser Gly Gly Gly Gly Ser Gly Gly Gly Gly Ser Gly Gly Gly
        355                 360                 365

Gly Ser Gly Gly Gly Ser Gly Gly Gly Gly Ser Gly Gly Gly Gly
370                 375                 380

Ser Asp Ile Gln Met Thr Gln Ser Pro Ser Ser Leu Ser Ala Ser Val
385                 390                 395                 400

Gly Asp Arg Val Thr Ile Thr Cys Ser Ala Ser Ser Ser Val Ser Tyr
                405                 410                 415

Met Asn Trp Tyr Gln Gln Thr Pro Gly Lys Ala Pro Lys Arg Trp Ile
                420                 425                 430

Tyr Asp Thr Ser Lys Leu Ala Ser Gly Val Pro Ser Arg Phe Ser Gly
                435                 440                 445

Ser Gly Ser Gly Thr Asp Tyr Thr Phe Thr Ile Ser Ser Leu Gln Pro
        450                 455                 460

Glu Asp Ile Ala Thr Tyr Tyr Cys Gln Gln Trp Ser Ser Asn Pro Phe
465                 470                 475                 480

Thr Phe Gly Gln Gly Thr Lys Leu Gln Ile Thr Arg
                485                 490

<210> SEQ ID NO 51
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
    50                  55                  60

Glu Gly Lys Ala Thr Leu Thr Val Asp Thr Ser Ala Ser Thr Ala His
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
    195                 200                 205

```
Thr Lys Val Asp Lys Arg Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Ala Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Ala Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 52
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val His Ser
            20                  25                  30
Asn Gly Asn Thr Tyr Leu Tyr Trp Tyr Leu Gln Lys Pro Gly Gln Ser
        35                  40                  45
Pro Lys Pro Leu Ile Tyr Arg Val Ser Asn Arg Phe Ser Gly Val Pro
    50                  55                  60
Cys Arg Phe Ser Gly Ser Gly Ser Gly Thr Asp Phe Thr Leu Lys Ile
65                  70                  75                  80
Ser Arg Val Glu Thr Glu Asp Val Gly Val Tyr Phe Cys Phe Gln Gly
                85                  90                  95
Thr His Val Pro Tyr Ile Phe Gly Gln Gly Thr Arg Leu Glu Ile Lys
            100                 105                 110
Arg Thr Val Ala Ala Pro Ser Val Phe Ile Phe Pro Pro Ser Asp Glu
```

```
            115                 120                 125
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Thr Ser Gly Gly Gly
        210                 215                 220

Gly Ser Gly Gly Gly Gly Ser Gly Gly Gly Ser Gln Val Gln Leu
225                 230                 235                 240

Val Gln Ser Gly Gly Gly Val Val Gln Pro Gly Arg Ser Leu Arg Leu
            245                 250                 255

Ser Cys Lys Ala Ser Gly Tyr Thr Phe Thr Arg Tyr Thr Met His Trp
        260                 265                 270

Val Arg Gln Ala Pro Gly Lys Cys Leu Glu Trp Ile Gly Tyr Ile Asn
            275                 280                 285

Pro Ser Arg Gly Tyr Thr Asn Tyr Asn Gln Lys Phe Lys Asp Arg Phe
        290                 295                 300

Thr Ile Ser Arg Asp Asn Ser Lys Asn Thr Ala Phe Leu Gln Met Asp
305                 310                 315                 320

Ser Leu Arg Pro Glu Asp Thr Gly Val Tyr Phe Cys Ala Arg Tyr Tyr
            325                 330                 335

Asp Asp His Tyr Ser Leu Asp Tyr Trp Gly Gln Gly Thr Pro Val Thr
        340                 345                 350

Val Ser Ser Gly Gly Gly Gly Ser Gly Gly Gly Gly Ser Gly Gly Gly
            355                 360                 365

Gly Ser Gly Gly Gly Gly Ser Gly Gly Gly Ser Gly Gly Gly Gly
        370                 375                 380

Ser Asp Ile Gln Met Thr Gln Ser Pro Ser Ser Leu Ser Ala Ser Val
385                 390                 395                 400

Gly Asp Arg Val Thr Ile Thr Cys Ser Ala Ser Ser Ser Val Ser Tyr
            405                 410                 415

Met Asn Trp Tyr Gln Gln Thr Pro Gly Lys Ala Pro Lys Arg Trp Ile
        420                 425                 430

Tyr Asp Thr Ser Lys Leu Ala Ser Gly Val Pro Ser Arg Phe Ser Gly
            435                 440                 445

Ser Gly Ser Gly Thr Asp Tyr Thr Phe Thr Ile Ser Ser Leu Gln Pro
        450                 455                 460

Glu Asp Ile Ala Thr Tyr Tyr Cys Gln Gln Trp Ser Ser Asn Pro Phe
465                 470                 475                 480

Thr Phe Gly Cys Gly Thr Lys Leu Gln Ile Thr Arg
            485                 490
```

<210> SEQ ID NO 53
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Val Ser Thr Ala Tyr
65                  70                  75                  80

Met Glu Leu Ser Ser Leu Thr Ser Glu Asp Asn Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

```
                        405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 54
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Cys Arg Tyr Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Ser Gly Gly Gly
    210                 215                 220

Gly Ser Gly Gly Gly Gly Ser Gly Gly Gly Ser Gln Val Gln Leu
225                 230                 235                 240

Val Gln Ser Gly Gly Gly Val Val Gln Pro Gly Arg Ser Leu Arg Leu
                245                 250                 255

Ser Cys Lys Ala Ser Gly Tyr Thr Phe Thr Arg Tyr Thr Met His Trp
            260                 265                 270

Val Arg Gln Ala Pro Gly Lys Cys Leu Glu Trp Ile Gly Tyr Ile Asn
        275                 280                 285

Pro Ser Arg Gly Tyr Thr Asn Tyr Asn Gln Lys Phe Lys Asp Arg Phe
    290                 295                 300

Thr Ile Ser Arg Asp Asn Ser Lys Asn Thr Ala Phe Leu Gln Met Asp
305                 310                 315                 320
```

```
Ser Leu Arg Pro Glu Asp Thr Gly Val Tyr Phe Cys Ala Arg Tyr Tyr
            325                 330                 335

Asp Asp His Tyr Ser Leu Asp Tyr Trp Gly Gln Gly Thr Pro Val Thr
        340                 345                 350

Val Ser Ser Gly Gly Gly Gly Ser Gly Gly Gly Ser Gly Gly Gly Gly
        355                 360                 365

Gly Ser Gly Gly Gly Gly Ser Gly Gly Gly Ser Gly Gly Gly Gly
    370                 375                 380

Ser Asp Ile Gln Met Thr Gln Ser Pro Ser Ser Leu Ser Ala Ser Val
385                 390                 395                 400

Gly Asp Arg Val Thr Ile Thr Cys Ser Ala Ser Ser Val Ser Tyr
                405                 410                 415

Met Asn Trp Tyr Gln Gln Thr Pro Gly Lys Ala Pro Lys Arg Trp Ile
                420                 425                 430

Tyr Asp Thr Ser Lys Leu Ala Ser Gly Val Pro Ser Arg Phe Ser Gly
            435                 440                 445

Ser Gly Ser Gly Thr Asp Tyr Thr Phe Thr Ile Ser Ser Leu Gln Pro
    450                 455                 460

Glu Asp Ile Ala Thr Tyr Tyr Cys Gln Gln Trp Ser Ser Asn Pro Phe
465                 470                 475                 480

Thr Phe Gly Cys Gly Thr Lys Leu Gln Ile Thr Arg
                485                 490

<210> SEQ ID NO 55
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asn Tyr
                20                  25                  30

Tyr Ile His Trp Val Met Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
        50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 56
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Arg Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
```

```
            100                 105                 110
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Ala Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 57
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ile Gln Leu Gln Gln Ser Gly Pro Glu Val Val Lys Pro Gly Ala
1               5                   10                  15
```

```
Ser Val Lys Ile Ser Cys Lys Ala Ser Gly Tyr Thr Phe Thr Arg Tyr
            20                  25                  30

Tyr Ile His Trp Val Met Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
 50                  55                  60

Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
```

<210> SEQ ID NO 58
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Arg Tyr
                20                  25                  30

Tyr Ile His Trp Val Lys Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
    195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
    275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 59
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 60
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

```
                180             185             190
Lys His Lys Val Tyr Ala Cys Glu Val Thr His Gln Gly Leu Ser Ser
            195             200             205

Pro Val Thr Lys Ser Phe Asn Arg Gly Glu Cys Thr Ser Gly Gly Gly
            210             215             220

Gly Ser Gly Gly Gly Ser Gly Gly Gly Ser His Val Gln Leu
225             230             235             240

Val Glu Ser Gly Gly Gly Leu Val Gln Pro Gly Gly Ser Leu Arg Leu
                245             250             255

Ser Cys Ala Ala Ser Gly Phe Ser Leu Thr Asp Tyr Gly Val His Trp
            260             265             270

Val Arg Gln Ala Pro Gly Lys Gly Leu Glu Trp Leu Gly Val Ile Trp
            275             280             285

Ser Gly Gly Gly Thr Ala Tyr Asn Thr Ala Leu Ile Ser Arg Phe Thr
            290             295             300

Ile Ser Arg Asp Asn Ser Lys Asn Thr Leu Tyr Leu Gln Met Asn Ser
305             310             315             320

Leu Arg Ala Glu Asp Thr Ala Val Tyr Tyr Cys Ala Arg Arg Gly Ser
                325             330             335

Tyr Pro Tyr Asn Tyr Phe Asp Ala Trp Gly Cys Gly Thr Leu Val Thr
            340             345             350

Val Ser Ser Gly Gly Gly Gly Ser Gly Gly Gly Gly Ser Gly Gly Gly
            355             360             365

Gly Ser Gly Gly Gly Ser Gly Gly Gly Gly Ser Gly Gly Gly Gly
            370             375             380

Ser Gln Ala Val Val Thr Gln Glu Pro Ser Leu Thr Val Ser Pro Gly
385             390             395             400

Gly Thr Val Thr Leu Thr Cys Gly Ser Ser Thr Gly Ala Val Thr Ala
                405             410             415

Ser Asn Tyr Ala Asn Trp Val Gln Gln Lys Pro Gly Gln Cys Pro Arg
            420             425             430

Gly Leu Ile Gly Gly His Asn Asn Arg Pro Pro Gly Val Pro Ala Arg
            435             440             445

Phe Ser Gly Ser Leu Leu Gly Gly Lys Ala Ala Leu Thr Leu Leu Gly
            450             455             460

Ala Gln Pro Glu Asp Glu Ala Glu Tyr Tyr Cys Ala Leu Trp Tyr Ser
465             470             475             480

Asp His Trp Val Ile Gly Gly Gly Thr Lys Leu Thr Val Leu Gly
                485             490             495

<210> SEQ ID NO 61
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Ile Gln Leu Gln Gln Ser Gly Pro Glu Val Val Lys Pro Gly Ala
1               5               10              15

Ser Val Lys Ile Ser Cys Lys Ala Ser Gly Tyr Thr Phe Thr Gly Tyr
            20              25              30

Tyr Ile His Trp Val Lys Gln Arg Pro Gly Gln Gly Leu Glu Trp Ile
            35              40              45
```

```
Gly Ser Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
                100                 105                 110

Val Thr Val Ser Ser Gly Gly Gly Ser Gly Gly Gly Ser Gly
             115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
                180                 185                 190

Ser Gly Val Pro Asp Arg Phe Ser Gly Ser Gly Ser Gly Thr Asp Phe
                195                 200                 205

Thr Leu Lys Ile Ser Arg Val Glu Ala Glu Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 62
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ile Gln Leu Gln Gln Ser Gly Pro Glu Val Val Lys Pro Gly Ala
  1               5                  10                  15

Ser Val Lys Ile Ser Cys Lys Ala Ser Gly Tyr Thr Phe Thr Asn Tyr
                 20                  25                  30

Tyr Ile His Trp Val Met Gln Arg Pro Gly Gln Gly Leu Glu Trp Ile
                 35                  40                  45

Gly Arg Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
                100                 105                 110

Val Thr Val Ser Ser Gly Gly Gly Gly Ser Gly Gly Gly Gly Ser Gly
             115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160
```

```
Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
            245

<210> SEQ ID NO 63
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Tyr Ile His Trp Val Lys Gln Arg Pro Gly Gln Gly Leu Glu Trp Ile
        35                  40                  45

Gly Cys Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
            245
```

```
<210> SEQ ID NO 64
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Met Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
        50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 65
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asn Tyr
                20                  25                  30

Tyr Ile His Trp Val Lys Gln Arg Pro Gly Gln Gly Leu Glu Trp Ile
            35                  40                  45

Gly Arg Ile Tyr Pro Gly Ser Gly Asn Thr Lys Tyr Asn Glu Lys Phe
```

```
                50                  55                  60
Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                    85                  90                  95

Ala Arg Gly Gly Lys Phe Ala Met Asp Tyr Trp Gly Gln Gly Thr Leu
                100                 105                 110

Val Thr Val Ser Ser Gly Gly Gly Ser Gly Gly Gly Ser Gly
            115                 120                 125

Gly Gly Gly Ser Asp Val Val Met Thr Gln Ser Pro Leu Ser Leu Pro
130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
                180                 185                 190

Ser Gly Val Pro Asp Arg Phe Ser Gly Ser Gly Ser Gly Thr Asp Phe
                195                 200                 205

Thr Leu Lys Ile Ser Arg Val Glu Ala Glu Asp Val Gly Val Tyr Phe
                210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 66
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Ile Gln Leu Gln Gln Ser Gly Pro Glu Val Val Lys Pro Gly Ala
  1               5                  10                  15

Ser Val Lys Ile Ser Cys Lys Ala Ser Gly Tyr Thr Phe Thr Asn Tyr
                 20                  25                  30

Tyr Ile His Trp Val Lys Gln Arg Pro Gly Gln Gly Leu Glu Trp Ile
             35                  40                  45

Gly Cys Ile Tyr Pro Gly Ser Gly Asn Thr Lys Tyr Asn Glu Lys Phe
 50                  55                  60

Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                    85                  90                  95

Ala Arg Gly Gly Lys Phe Ala Met Asp Tyr Trp Gly Gln Gly Thr Leu
                100                 105                 110

Val Thr Val Ser Ser Gly Gly Gly Gly Ser Gly Gly Gly Gly Ser Gly
            115                 120                 125

Gly Gly Gly Ser Asp Val Val Met Thr Gln Ser Pro Leu Ser Leu Pro
130                 135                 140

Val Thr Leu Gly Gln Pro Ala Ser Ile Ser Cys Arg Ser Ser Gln Ser
145                 150                 155                 160
```

```
Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 67
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Glu Gly Lys Ala Thr Leu Thr Val Asp Thr Ser Ala Ser Thr Ala His
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Gly Val Pro Cys Arg Phe Ser Gly Ser Gly Ser Gly Thr Asp Phe
        195                 200                 205

Thr Leu Lys Ile Ser Arg Val Glu Thr Glu Asp Val Gly Val Tyr Phe
    210                 215                 220

Cys Phe Gln Gly Thr His Val Pro Tyr Ile Phe Gly Gln Gly Thr Arg
225                 230                 235                 240

Leu Glu Ile Lys Arg
                245

<210> SEQ ID NO 68
```

```
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68
```

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Cys Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Cys Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
                245

```
<210> SEQ ID NO 69
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69
```

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Cys Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

```
Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Asp Val Val Met Thr Gln Ser Pro Leu Ser Leu Pro
130                 135                 140

Val Thr Leu Gly Gln Pro Ala Ser Ile Ser Cys Arg Ser Ser Gln Ser
145                 150                 155                 160

Leu Val His Ser Asn Gly Lys Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Cys Val Pro Asp Arg Phe Ser Gly Ser Gly Ser Gly Thr Asp Phe
            195                 200                 205

Thr Leu Lys Ile Ser Arg Val Glu Ala Glu Asp Val Gly Val Tyr Phe
            210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 70
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ile Gln Leu Gln Gln Ser Gly Pro Glu Val Val Lys Pro Gly Ala
 1               5                  10                  15

Ser Val Lys Ile Ser Cys Lys Ala Ser Ala Tyr Thr Phe Thr Asp Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Val Asp Thr Ser Ala Ser Thr Ala Tyr
 65                  70                  75                  80

Met Glu Leu Ser Ser Leu Thr Ser Glu Asp Thr Ala Val Tyr Phe Cys
                 85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Asp Val Val Met Thr Gln Ser Pro Leu Ser Leu Pro
130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
```

165                 170                 175
Pro Gly Gln Ser Pro Lys Pro Leu Ile Tyr Arg Val Ser Asn Arg Phe
                180                 185                 190

Ser Gly Val Pro Cys Arg Phe Ser Gly Ser Gly Ser Gly Thr Asp Phe
            195                 200                 205

Thr Leu Lys Ile Ser Arg Val Glu Ala Glu Asp Val Gly Val Tyr Phe
        210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 71
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Lys Ser Pro Lys Pro Leu Ile Tyr Arg Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Lys Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 72
<211> LENGTH: 245

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Asp Val Val Met Thr Gln Ser Pro Leu Ser Leu Pro
130                 135                 140

Val Thr Leu Gly Gln Pro Val Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Gly Val Pro Cys Arg Phe Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Phe Gln Gly Thr His Glu Pro Tyr Thr Phe Gly Gln Gly Thr Arg
225                 230                 235                 240

Leu Glu Ile Lys Arg
                245

<210> SEQ ID NO 73
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60
```

```
Lys Gly Lys Ala Thr Leu Thr Val Asp Thr Ser Val Ser Thr Ala Tyr
 65                  70                  75                  80

Met Glu Leu Ser Ser Leu Thr Ser Glu Asp Asn Ala Val Tyr Phe Cys
                 85                  90                  95

Ala Arg Gly Gly Lys Phe Ala Met Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Val Val Met Thr Gln Ser Pro Leu Ser Leu Pro
    130                 135                 140

Val Thr Leu Gly Gln Pro Ala Ser Ile Ser Cys Arg Ser Ser Gln Ser
145                 150                 155                 160

Leu Val His Ser Asn Gly Asn Thr Tyr Leu Tyr Trp Tyr Leu Gln Lys
                165                 170                 175

Pro Gly Gln Ser Pro Lys Pro Leu Ile Tyr Arg Val Ser Asn Arg Phe
            180                 185                 190

Ser Gly Val Pro Cys Arg Tyr Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Phe Gln Gly Thr His Val Pro Tyr Thr Phe Gly Gln Gly Thr Arg
225                 230                 235                 240

Leu Glu Ile Lys Arg
                245

<210> SEQ ID NO 74
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Ile Gln Leu Gln Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Tyr Ile His Trp Val Lys Gln Ala Pro Gly Gln Arg Leu Glu Trp Ile
            35                  40                  45

Gly Trp Ile Tyr Pro Gly Ser Gly Asn Thr Lys Tyr Asn Gln Lys Phe
        50                  55                  60

Gln Gly Arg Val Thr Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 75
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Gln Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Arg Gln Ala Pro Gly Gln Arg Leu Glu Trp Met
        35                  40                  45

Gly Trp Ile Tyr Pro Gly Ser Gly Asn Thr Lys Tyr Ser Gln Lys Phe
    50                  55                  60

Gln Gly Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
```

```
            85                  90                  95
Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 76
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76
```

-continued

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Arg Gln Ala Pro Gly Gln Arg Leu Glu Trp Met
            35                  40                  45

Gly Trp Ile Tyr Pro Gly Ser Gly Asn Thr Lys Tyr Ser Glu Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Phe Cys
            85                  90                  95

Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu

His Asn His Tyr Thr Gln Lys Ser Leu Ser Leu Ser Pro Gly Lys
            435                 440                 445

<210> SEQ ID NO 77
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Gln Ser Gly Pro Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Arg Gln Ala Pro Gly Gln Arg Leu Glu Trp Ile
        35                  40                  45

Gly Trp Ile Tyr Pro Gly Ser Gly Asn Thr Lys Tyr Ser Gln Lys Phe
    50                  55                  60

Gln Gly Lys Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

```
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 78
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Ser Gly Asn Thr Lys Tyr Ser Gln Lys Phe
    50                  55                  60

Lys Gly Arg Ala Thr Leu Thr Arg Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

-continued

Pro Glu Val Thr Cys Val Val Asp Val Ser His Glu Asp Pro Glu
        260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 79
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Ile Gln Leu Gln Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Arg Gln Ala Pro Gly Gln Arg Leu Glu Trp Ile
            35                  40                  45

Gly Trp Ile Tyr Pro Gly Ser Gly Asn Thr Lys Tyr Ser Gln Lys Phe
        50                  55                  60

Gln Gly Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser 165                 170                 175
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 80
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Ile Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Arg Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Gly Gly Lys Phe Ala Met Asp Tyr Trp Gly Gln Gly Thr Ser
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 81
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Gln Val Gln Leu Val Gln Ser Gly Ala Glu Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Arg Gln Ala Pro Gly Gln Arg Leu Glu Trp Ile
            35                  40                  45

Gly Trp Ile Tyr Pro Gly Ser Gly Asn Thr Lys Tyr Asn Glu Lys Phe
50                      55                  60

Lys Gly Arg Val Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Phe Ala Met Asp Tyr Trp Gly Gln Gly Thr Ser
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                     140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 82
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Gln Gln Arg Pro Gly Gln Ser
        35                  40                  45

Pro Arg Arg Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 83
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Tyr Trp Tyr Gln Gln Arg Pro Gly Gln Ser
        35                  40                  45
```

```
Pro Arg Pro Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Arg Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215
```

<210> SEQ ID NO 84
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Gly Asn Thr Tyr Leu Tyr Trp Phe Gln Gln Arg Pro Gly Gln Ser
            35                  40                  45

Pro Arg Pro Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Arg Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 85
<211> LENGTH: 384
<212> TYPE: PRT
<213> ORGANISM: Homo sapiens

<400> SEQUENCE: 85

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
```

```
                    340                 345                 350
Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
        370                 375                 380

<210> SEQ ID NO 86
<211> LENGTH: 330
<212> TYPE: PRT
<213> ORGANISM: Homo sapiens

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 87
<211> LENGTH: 326
<212> TYPE: PRT
<213> ORGANISM: Homo sapiens

<400> SEQUENCE: 87

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 88
<211> LENGTH: 377
<212> TYPE: PRT
<213> ORGANISM: Homo sapiens

<400> SEQUENCE: 88

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 89
<211> LENGTH: 452
<212> TYPE: PRT
<213> ORGANISM: Homo sapiens

<400> SEQUENCE: 89
```

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
            50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
            130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
                180                 185                 190

Ser Met Phe Thr Cys Arg Val Asp His Arg Gly Leu Thr Phe Gln Gln
            195                 200                 205

Asn Ala Ser Ser Met Cys Val Pro Asp Gln Asp Thr Ala Ile Arg Val
            210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
                260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
            290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415
```

```
Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
            450

<210> SEQ ID NO 90
<211> LENGTH: 327
<212> TYPE: PRT
<213> ORGANISM: Homo sapiens

<400> SEQUENCE: 90

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 91
<211> LENGTH: 353
<212> TYPE: PRT
<213> ORGANISM: Homo sapiens

<400> SEQUENCE: 91

```
Ala Ser Pro Thr Ser Pro Lys Val Phe Pro Leu Ser Leu Cys Ser Thr
 1               5                  10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr
```

<210> SEQ ID NO 92

<211> LENGTH: 1344
<212> TYPE: DNA
<213> ORGANISM: Homo sapiens

<400> SEQUENCE: 92

```
cagatccagc tgcagcagtc tggacccgag gtcgtgaagc ctggcgcctc cgtgaagatc      60
tcctgcaagg cctccggcta caccttcacc gactactaca tccactgggt caagcagcgg     120
ccaggccagg gcctggaatg gatcggctgg atctatcccg gctccggcaa caccaagtac     180
aacgagaagt tcaagggcaa ggccaccctg accgtgaca cctctgcctc caccgcctac     240
atggaactgt cctccctgac ctccgaggat accgccgtgt acttctgtgc cagaggcggc     300
aagttcgcca tggactattg gggccagggc accctcgtga ccgtgtctag cgcttctacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggccgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga gagttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atga                                           1344
```

<210> SEQ ID NO 93
<211> LENGTH: 1344
<212> TYPE: DNA
<213> ORGANISM: Homo sapiens

<400> SEQUENCE: 93

```
cagatccagc tggtgcagtc tggacccgag gtcgtgaagc ctggcgcctc cgtgaagatc      60
tcctgcaagg cctccggcta caccttcacc gactactaca tccactgggt gcgacaggcc     120
cctggacagg gcctggaatg gatcggctgg atctaccctg gctccggcaa caccaagtac     180
aacgagaagt tcaagggcag agccaccctg accgtgaca cctctgcctc caccgcctac     240
atggaactgt cctccctgcg gagcgaggat accgccgtgt acttctgtgc cagaggcggc     300
aagttcgcca tggactattg gggccagggc accctcgtga ccgtgtctag cgcttctacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggccgtcc tacagtcctc aggactctac     540
tccctcagca gcgtggtgac cgtgccctcc agcagcttgg gcacccagac ctacatctgc     600
```

-continued

```
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atga                                         1344
```

<210> SEQ ID NO 94
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

```
gacgtcgtga tgacacagtc ccctctgtcc ctgcctgtga ccctgggcga tcaggcctcc    60
atctcctgca gatcctccca gtccctggtg cactccaacg gcaacaccta cctgtactgg   120
tatctgcaga agcccggcca gtcccccaag ccctgatct acagagtgtc caaccggttc   180
tccggcgtgc ccgacagatt ctccggctct ggctctggca ccgacttcac cctgaagatc   240
tcccgggtgg aagccgagga cgtgggcgtg tacttctgtt ttcaaggcac ccacgtgccc   300
tacaccttcg gcggaggcac ccggctggaa atcaagagaa ccgtggccgc tcccctccgtg   360 ttcatcttcc caccttccga cgagcagctg aagtccggca ccgcttctgt cgtgtgcctg   420
ctgaacaact ctaccccccg cgaggccaag gtgcagtgga aggtggacaa cgccctgcag   480
tccggcaact cccaggaatc cgtgaccgag caggactcca aggacagcac ctactccctg   540
tcctccaccc tgaccctgtc caaggccgac tacgagaagc acaaggtgta cgcctgcgaa   600
gtgacccacc agggcctgtc tagccccgtg accaagtctt tcaaccgggg cgagtgctag   660
```

<210> SEQ ID NO 95
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
gacgtcgtga tgacacagtc ccctctgtcc ctgcctgtga cccctgggaca gcctgcctcc    60 atctcctgca gatcctccca gtccctggtg cactccaacg gcaacaccta cctgtactgg   120
tatctgcaga agcccggcca gtcccccaag ccctgatct acagagtgtc caaccggttc   180
tccggcgtgc ccgacagatt ctccggctct ggctctggca ccgacttcac cctgaagatc   240
```

```
tcccgggtgg aagccgagga cgtgggcgtg tacttctgtt ttcaaggcac ccacgtgccc      300
tacaccttcg gccagggcac ccggctggaa atcaagagaa ccgtggccgc tccctccgtg      360
ttcatcttcc caccttccga cgagcagctg aagtccggca ccgcttctgt cgtgtgcctg      420
ctgaacaact tctaccccg cgaggccaag gtgcagtgga aggtggacaa cgccctgcag       480
tccggcaact cccaggaatc cgtgaccgag caggactcca aggacagcac ctactccctg      540
tcctccaccc tgaccctgtc caaggccgac tacgagaagc acaaggtgta cgcctgcgaa      600
gtgacccacc agggcctgtc tagccccgtg accaagtctt tcaaccgggg cgagtgctag     660
```

<210> SEQ ID NO 96
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
cagatccagc tgcagcagtc tggacccgag gtcgtgaagc ctggcgcctc cgtgaagatc      60
tcctgcaagg cctccggcta caccttcacc gactactaca tccactgggt caagcagcgg     120
ccaggccagg gcctggaatg gatcggctgg atctatcccg gctccggcaa caccaagtac     180
aacgagaagt tcaagggcaa ggccaccctg accgtggaca cctctgcctc caccgcctac     240
atggaactgt cctccctgac ctccgaggat accgccgtgt acttctgtgc cagaggcggc     300
aagttcgcca tggactattg gggccagggc accctcgtga ccgtgtctag cgcttctacc     360
aagggcccct ctgtgtttcc tctggccccc tccagcaagt ccacctctgg tggaacagcc     420
gccctgggct gcctcgtgaa ggactacttt cccgagcccg tgaccgtgtc ctggaactct     480
ggcgctctga cctctggcgt gcacaccttc cctgctgtgc tgcagtctag cggcctgtac     540
tccctgtcct ccgtcgtgac agtgcccctcc agctctctgg gcacccagac ctacatctgc     600
aacgtgaacc acaagccctc caataccaag gtggacaagc gggtggaacc caagtcctgc     660
gacaagaccc acacctgtcc cccttgtcct gcccctgaac tgctgggcgg accttccgtg     720
ttcctgttcc cccaaagcc caaggacacc ctgatgatct cccggacccc cgaagtgacc     780
tgcgtggtgg tggatgtgtc ccacgaggac cctgaagtga agttcaattg gtacgtggac     840
ggcgtggaag tgcacaacgc caagaccaag cctagagagg aacagtacgc ctccacctac     900
cgggtggtgt ccgtgctgac agtgctgcac caggactggc tgaacggcaa agagtacaag     960
tgcgccgtgt ccaacaaggc cctgcctgcc cccatcgaaa agaccatctc caaggccaag    1020
ggccagcccc gggaacccca ggtgtacaca ctgccccta gcagggacga gctgaccaag    1080
aaccaggtgt ccctgacctg tctcgtgaaa ggcttctacc cctccgatat cgccgtggaa    1140
tgggagtcca acggccagcc tgagaacaac tacaagacca cccccctgt gctggactcc    1200 gacggctcat tcttcctgta cagcaagctg accgtggaca gtccggtg cagcagggc      1260 aacgtgttct cctgctccgt gatgcacgag gccctgcaca accactacac ccagaagtcc    1320
ctgtccctga cccccggcaa atga                                           1344
```

<210> SEQ ID NO 97
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
gacgtcgtga tgacacagtc ccctctgtcc ctgcctgtga ccctgggaca gcctgcctcc      60
atctcctgca gatcctccca gtccctggtg cactccaacg gcaacaccta cctgtactgg    120
tatctgcaga agcccggcca gtcccccaag cccctgatct acagagtgtc caaccggttc    180
tccggcgtgc ccgacagatt ctccggctct ggctctggca ccgacttcac cctgaagatc    240
tcccgggtgg aagccgagga cgtgggcgtg tacttctgtt ttcaaggcac ccacgtgccc    300
tacaccttcg gccagggcac ccggctggaa atcaagagaa ccgtggccgc tccctccgtg    360
ttcatcttcc caccttccga cgagcagctg aagtccggca ccgcttctgt cgtgtgcctg    420
ctgaacaact tctaccccg  cgaggccaag gtgcagtgga aggtggacaa cgccctgcag    480
tccggcaact cccaggaatc cgtgaccgag caggactcca aggacagcac ctactccctg    540
tcctccaccc tgaccctgtc caaggccgac tacgagaagc acaaggtgta cgcctgcgaa    600
gtgacccacc agggcctgtc tagccccgtg accaagtctt tcaaccgggg cgagtgcact    660
agtggcggcg gaggatctgg cggaggtgga agcggagggg gaggatctca ggtgcagctg    720
gtgcagagcg gagccggagt ggtgcagcct ggcagatccc tgagactgtc ctgcaaggcc    780
tccggctaca ccttcacccg gtacaccatg cactgggtgc gacaggcccc tggcaagtgc    840
ctggaatgga tcggctacat caaccccctc cggggctaca ccaactacaa ccagaagttc    900
aaggaccggt tcaccatctc ccgggacaac tccaagaaca ccgcctttct gcagatggac    960
tccctgcggc ctgaggatac cggcgtgtac ttctgcgccc ggtactacga cgaccactac   1020
tccctggact actggggcca gggaaccct  gtgacagtgt catctggtgg cggaggaagt   1080
gggggaggcg gatcaggtgg tggtggatca ggcgggggag gttcagggg  tggcggttct   1140
gggggagggg gctctgatat tcagatgact cagagcccct tccagcctga gcgcctccgtg  1200
ggagatcgcg tgacaattac ctgctctgcc tcctcctccg tgtcttacat gaattggtat   1260
cagcagaccc ctgggaaggc tcctaagcgg tggatctacg acacctccaa gctggcctct   1320
ggcgtgccca gcaggttttc tggctccggc agcggcacag attatacctt caccatcagc   1380
tccctgcagc cagaagatat cgctacctat tattgtcagc agtggcctc  caacccttc   1440
accttcggct gcggcacaaa gctgcagatc acaagatag                          1479
```

<210> SEQ ID NO 98
<211> LENGTH: 1485
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
gacgtcgtga tgacacagtc ccctctgtcc ctgcctgtga ccctgggaca gcctgcctcc      60
atctcctgca gatcctccca gtccctggtg cactccaacg gcaacaccta cctgtactgg    120
tatctgcaga agcccggcca gtcccccaag cccctgatct acagagtgtc caaccggttc    180
tccggcgtgc ccgacagatt ctccggctct ggctctggca ccgacttcac cctgaagatc    240
tcccgggtgg aagccgagga cgtgggcgtg tacttctgtt ttcaaggcac ccacgtgccc    300
tacaccttcg gccagggcac ccggctggaa atcaagagaa ccgtggccgc tccctccgtg    360
ttcatcttcc caccttccga cgagcagctg aagtccggca ccgcttctgt cgtgtgcctg    420
ctgaacaact tctaccccg  cgaggccaag gtgcagtgga aggtggacaa cgccctgcag    480
```

| | | |
|---|---|---|
| tccggcaact cccaggaatc cgtgaccgag caggactcca aggacagcac ctactccctg | 540 |
| tcctccaccc tgaccctgtc caaggccgac tacgagaagc acaaggtgta cgcctgcgaa | 600 |
| gtgacccacc agggcctgtc tagccccgtg accaagtctt tcaaccgggg cgagtgcact | 660 |
| agtggcggcg gaggatctgg cggaggtgga agtgggggag cggatctca ggtgcagctg | 720 |
| gtgcagagtg gtggcggagt ggtgcagcct ggcagatccc tgagactgtc ttgcaaggcc | 780 |
| agcggctaca ccttcacccg gtacaccatg cactgggtgc gacaggcccc tggcaagggc | 840 |
| ctggaatgga tcggctacat caaccccctcc cggggctaca ccaactacaa ccagaagttc | 900 |
| aaggaccggt tcaccatcag ccgggacaac tccaagaaca ccgcctttct gcagatggac | 960 |
| tccctgcggc ctgaggatac cggcgtgtac ttttgcgccc ggtactacga cgaccactac | 1020 |
| agcctggact actgggccca gggaacccct gtgacagtgt ctagcggagg gggaggttca | 1080 |
| ggtggcggtg gatcagggg cggaggaagt ggcgggggag gtagtggtgg tggtggaagc | 1140 |
| ggaggtggcg gctccgatat ccagatgacc cagtccccct ccagcctgtc tgcctctgtg | 1200 |
| ggagacagag tgacaattac atgctccgcc agctccagcg tgtcctacat gaattggtat | 1260 |
| cagcagaccc ctggcaaggc tcccaagcgg tggatctacg acacctccaa gctggcctcc | 1320 |
| ggcgtgccct ccagatttc tggcagcggc tccggcacag actataccct tacaatcagc | 1380 |
| tccctgcagc ccgaagatat cgccacctac tactgccagc agtggcctc caaccccttc | 1440 |
| accttcggcc agggcacaaa gctgcagatc accagatagt ctaga | 1485 |

<210> SEQ ID NO 99
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

| | | |
|---|---|---|
| cagatccagc tgcagcagtc tggacccgag gtcgtgaagc ctggcgcctc cgtgaagatc | 60 |
| tcctgcaagg cctccggcta caccttcacc gactactaca tccactgggt caagcagcgg | 120 |
| ccaggccagg gcctggaatg gatcggctgg atctatcccg gctccggcaa caccaagtac | 180 |
| aacgagaagt tcgagggcaa ggccaccctg accgtggaca cctctgcctc caccgcccac | 240 |
| atggaactgt cctccctgac ctccgaggat accgccgtgt acttctgtgc cagaggcggc | 300 |
| aagttcgcca tggactattg gggccagggc accctcgtga ccgtgtctag cgcctccacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggccgtcc tacagtcctc aggactctac | 540 |
| tccctcagca gcgtggtgac agtgccctcc agctctctgg gcacccagac ctacatctgc | 600 |
| aacgtgaacc acaagccctc caataccaag gtggacaagg gggtggaacc caagtcctgc | 660 |
| gacaagaccc acacctgtcc cccttgtcct gcccctgaac tgctgggcgg accttccgtg | 720 |
| ttcctgttcc cccaaagcc caaggacacc ctgatgatct cccggacccc cgaagtgacc | 780 |
| tgcgtggtgg tggatgtgtc cacgaggac cctgaagtga agttcaattg gtacgtggac | 840 |
| ggcgtggaag tgcacaacgc caagaccaag cctagagagg aacagtacgc ctccacctac | 900 |
| cgggtggtgt ccgtgctgac agtgctgcac caggactggc tgaacggcaa agagtacaag | 960 |
| tgcgccgtgt ccaacaaggc cctgcctgcc cccatcgaaa agaccatctc caaggccaag | 1020 |

```
ggccagcccc gggaacccca ggtgtacaca ctgcccccta gcagggacga gctgaccaag   1080
aaccaggtgt ccctgacctg tctcgtgaaa ggcttctacc cctccgatat cgccgtggaa   1140
tgggagtcca acggccagcc tgagaacaac tacaagacca ccccccctgt gctggactcc   1200
gacggctcat tcttcctgta cagcaagctg accgtggaca gtcccggtg gcagcagggc    1260 aacgtgttct cctgctccgt gatgcacgag gccctgcaca accactacac ccagaagtcc   1320
ctgtccctga gccccggcaa atga                                          1344
```

<210> SEQ ID NO 100
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gacgtcgtga tgacacagtc ccctctgtcc ctgcctgtga ccctgggaca gcctgcctcc     60
atctcctgca gatcctccca gtccctggtg cactccaacg gcaacaccta cctgtactgg    120
tatctgcaga agcccggcca gtcccccaag cccctgatct acagagtgtc caaccggttc    180
tccggcgtgc cctgcagatt ctccggctct ggctctggca ccgacttcac cctgaagatc    240
tcccgggtgg aaaccgagga cgtgggcgtg tacttctgtt ttcaaggcac ccacgtgccc    300
tacatcttcg gccagggcac ccggctggaa atcaagcgga ccgtggccgc tccctccgtg    360
ttcatcttcc caccttccga cgagcagctg aagtccggca ccgcttctgt cgtgtgcctg    420
ctgaacaact tctaccccg cgaggccaag gtgcagtgga aggtggacaa cgccctgcag    480
tccggcaact cccaggaatc cgtgaccgag caggactcca aggacagcac ctactccctg    540
tcctccaccc tgaccctgtc caaggccgac tacgagaagc acaaggtgta cgcctgcgaa    600
gtgacccacc agggcctgtc tagccccgtg accaagtctt tcaaccgggg cgagtgcact    660
agtggcggcg gaggatctgg cggaggtgga agcggagggg gaggatctca ggtgcagctg    720
gtgcagagcg gagcggagt ggtgcagcct ggcagatccc tgagactgtc ctgcaaggcc    780
tccggctaca ccttcacccg gtacaccatg cactgggtgc gacaggcccc tggcaagtgc    840
ctggaatgga tcggctacat caaccccctcc cggggctaca ccaactacaa ccagaagttc    900
aaggaccggt tcaccatctc ccgggacaac tccaagaaca ccgcctttct gcagatggac    960
tccctgcggc ctgaggatac cgccgtgtac ttctgcgccc ggtactacga cgaccactac   1020
tccctggact actggggcca gggaacccct gtgacagtgt catctggtgg cggaggaagt   1080
gggggaggcg gatcaggtg tggtggatca ggcgggggag gttcaggggg tggcggttct   1140 ggggagggg gctctgatat tcagatgact cagagcccctt ccagcctgag cgcctccgtg   1200
ggagatcgcg tgacaattac ctgctctgcc tcctcctccg tgtcttacat gaattggtat   1260
cagcagaccc ctgggaaggc tcctaagcgg tggatctacg acacctccaa gctggcctct   1320
ggcgtgccca gcaggttttc tggctccggc agcggcacag attataccttt caccatcagc   1380 tccctgcagc cagaagatat cgctacctat tattgtcagc agtggtcctc caacccttc   1440 accttcggct gcggcacaaa gctgcagatc acaagatag                         1479
```

<210> SEQ ID NO 101
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
cagatccagc tgcagcagtc tggacccgag gtcgtgaagc ctggcgcctc cgtgaagatc      60
tcctgcaagg cctccggcta caccttcacc gactactaca tccactgggt caagcagcgg     120
ccaggccagg gctggaatg gatcggctgg atctatcccg gctccggcaa caccaagtac      180
aacgagaagt tcaagggcaa ggccaccctg accgtggaca cctctgtctc caccgcctac    240
atggaactgt cctccctgac ctccgaggat aacgccgtgt acttctgtgc cagaggcggc    300
aagttcgcca tggactattg gggccagggc accctcgtga ccgtgtctag cgcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggccgtcc tacagtcctc aggactctac    540
tccctcagca gcgtggtgac agtgccctcc agctctctgg gcacccagac ctacatctgc    600
aacgtgaacc acaagccctc caataccaag gtggacaagc gggtggaacc caagtcctgc    660
gacaagaccc acacctgtcc cccttgtcct gcccctgaac tgctgggcgg accttccgtg    720
ttcctgttcc ccccaaagcc caaggacacc ctgatgatct cccggacccc cgaagtgacc    780
tgcgtggtgg tggatgtgtc ccacgaggac cctgaagtga agttcaattg gtacgtggac    840
ggcgtggaag tgcacaacgc caagaccaag cctagagagg aacagtacgc ctccacctac    900
cgggtggtgt ccgtgctgac agtgctgcac caggactggc tgaacggcaa agagtacaag    960
tgcgccgtgt ccaacaaggc cctgcctgcc ccatcgaaa agaccatctc caaggccaag    1020
ggccagcccc gggaacccca ggtgtacaca ctgcccccta gcagggacga gctgaccaag   1080
aaccaggtgt ccctgacctg tctcgtgaaa ggcttctacc cctccgatat cgccgtggaa   1140
tgggagtcca acggccagcc tgagaacaac tacaagacca ccccccctgt gctggactcc   1200
gacggctcat tcttcctgta cagcaagctg accgtggaca gtcccggtg cagcagggc     1260
aacgtgttct cctgctccgt gatgcacgag gccctgcaca accactacac ccagaagtcc   1320
ctgtccctga gccccggcaa atga                                          1344
```

<210> SEQ ID NO 102
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
gacgtcgtga tgacacagtc ccctctgtcc ctgcctgtga ccctgggaca gcctgcctcc      60
atctcctgca gatcctccca gtccctggtg cactccaacg gcaacaccta cctgtactgg    120
tatctgcaga agcccggcca gtcccccaag cccctgatct acagagtgtc caaccggttc    180
tccggcgtgc cctgcagata ctccggctct ggctctggca ccgacttcac cctgaagatc    240
tcccgggtgg aagccgagga cgtgggcgtg tacttctgtt ttcaaggcac ccacgtgccc    300
tacaccttcg gccagggcac ccggctggaa atcaagcgga ccgtggccgc tccctccgtg    360
ttcatcttcc caccttccga cgagcagctg aagtccggca ccgcttctgt cgtgtgcctg    420
ctgaacaact tctaccccc gcgaggccaag gtgcagtgga aggtggacaa cgccctgcag    480
```

```
tccggcaact cccaggaatc cgtgaccgag caggactcca aggacagcac ctactccctg    540
tcctccaccc tgaccctgtc caaggccgac tacgagaagc acaaggtgta cgcctgcgaa    600
gtgacccacc agggcctgtc tagccccgtg accaagtctt tcaaccgggg cgagtgcact    660
agtggcggcg gaggatctgg cggaggtgga agcggagggg gaggatctca ggtgcagctg    720
gtgcagagcg gaggcggagt ggtgcagcct ggcagatccc tgagactgtc ctgcaaggcc    780
tccggctaca ccttcacccg gtacaccatg cactgggtgc acaggcccc tgcaagtgc     840 ctggaatgga tcggctacat caaccccctcc cggggctaca ccaactacaa ccagaagttc    900
aaggaccggt tcaccatctc ccgggacaac tccaagaaca ccgcctttct gcagatggac    960
tccctgcggc ctgaggatac cggcgtgtac ttctgcgccc ggtactacga cgaccactac   1020
tccctggact actggggcca gggaaccccct gtgacagtgt catctggtgg cggaggaagt   1080
gggggaggcg gatcaggtgg tggtggatca ggcggggag gttcagggg tggcggttct    1140 gggggagggg gctctgatat tcagatgact cagagccctt ccagcctgag cgcctccgtg   1200
ggagatcgcg tgacaattac ctgctctgcc tcctcctccg tgtcttacat gaattggtat   1260
cagcagaccc ctgggaaggc tcctaagcgg tggatctacg acacctccaa gctggcctct   1320
ggcgtgccca gcaggttttc tggctccggc agcggcacag attataccttt caccatcagc   1380 tccctgcagc cagaagatat cgctacctat tattgtcagc agtggtcctc caacccttc    1440 accttcggct gcggcacaaa gctgcagatc acaagatag                          1479
```

<210> SEQ ID NO 103
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
ccgccaccgg cccagatcca gctgcagcag tctggaccg aggtcgtgaa gcctggcgcc     60
tccgtgaaga tctcctgcaa ggcctccggc tacaccttca ccaactacta catccactgg   120
gtcatgcagc ggccaggcca gggcctggaa tggatcggcc ggatctatcc cggctccggc   180
aacaccaagt acaacgagaa gttcaagggc aaggccaccc tgaccgtgga cacctctgcc   240
tccaccgcct acatggaact gtcctccctg acctccgagg ataccgccgt gtacttctgt   300
gccagaggcg gcaagttcgc catggactat tggggccagg gcaccctcgt gaccgtgtct   360
agcgcctcca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tccggccgt cctacagtcc   540 tcaggactct actccctcag cagcgtggtg acagtgccct ccagctctct gggcacccag   600
acctacatct gcaacgtgaa ccacaagccc tccaatacca aggtggacaa gcgggtggaa   660
cccaagtcct gcgacaagac ccacacctgt cccccttgtc ctgccccga actgctgggc   720 ggaccttccg tgttcctgtt ccccccaaag cccaaggaca ccctgatgat ctcccggacc   780
cccgaagtga cctgcgtggt ggtggatgtg tcccacgagg accctgaagt gaagttcaat   840
tggtacgtgg acggcgtgga agtgcacaac gccaagacca gcctagaga ggaacagtac   900 gcctccacct accgggtggt gtccgtgctg acagtgctgc accaggactg gctgaacggc   960
aaagagtaca gtgcgccgt gtccaacaag gccctgcctg cccccatcga aaagaccatc   1020
```

| | |
|---|---|
| tccaaggcca agggccagcc ccgggaaccc caggtgtaca cactgccccc tagcagggac | 1080 |
| gagctgacca agaaccaggt gtccctgacc tgtctcgtga aaggcttcta ccctccgat | 1140 |
| atcgccgtgg aatgggagtc aacggccag cctgagaaca actacaagac cacccccct | 1200 |
| gtgctggact ccgacggctc attcttcctg tacagcaagc tgaccgtgga caagtcccgg | 1260 |
| tggcagcagg gcaacgtgtt ctcctgctcc gtgatgcacg aggccctgca aaccactac | 1320 |
| acccagaagt ccctgtccct gagccccggc aaatga | 1356 |

<210> SEQ ID NO 104
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

| | |
|---|---|
| cagatccagc tgcagcagtc tggacccgag gtcgtgaagc ctggcgcctc cgttaagatc | 60 |
| tcctgcaagg cctccggcta caccttcacc aactactaca tccactgggt caagcagcgg | 120 |
| ccaggccaag gctggaatg gatcggccgg atctatcccg ctccggcaa caccaagtac | 180 |
| aacgagaagt tcaagggcaa ggccaccctg accgtgaca cctctgcctc caccgcctac | 240 |
| atgaactgt cctccctgac ctccgaggat accgccgtgt acttctgtgc cagaggcggc | 300 |
| aagttcgcca tggactattg gggccagggc accctcgtga ccgtgtctag cgcctccacc | 360 |
| aagggcccat cggtcttccc cctggcaccc tcctccaaga gcacctctgg ggcacagcg | 420 |
| gccctgggct gcctggtcaa ggactacttc cccgaaccgg tgacggtgtc gtggaactca | 480 |
| ggcgccctga ccagcggcgt gcacaccttc cggccgtcc tacagtcctc aggactctac | 540 |
| tccctcagca gcgtggtgac agtgccctcc agctctctgg gcacccagac ctacatctgc | 600 |
| aacgtgaacc acaagccctc caataccaag gtggacaagc gggtggaacc caagtcctgc | 660 |
| gacaagaccc acacctgtcc cccttgtcct gcccctgaac tgctgggcgg accttccgtg | 720 |
| ttcctgttcc ccccaaagcc caaggacacc ctgatgatct cccggacccc cgaagtgacc | 780 |
| tgcgtggtgg tggatgtgtc ccacgaggac cctgaagtga agttcaattg gtacgtggac | 840 |
| ggcgtggaag tgcacaacgc caagaccaag cctagagagg aacagtacgc ctccacctac | 900 |
| cgggtggtgt ccgtgctgac agtgctgcac caggactggc tgaacggcaa agagtacaag | 960 |
| tgcgccgtgt ccaacaaggc cctgcctgcc cccatcgaaa agaccatctc caaggccaag | 1020 |
| ggccagcccc gggaacccca ggtgtacaca ctgccccta gcagggacga gctgaccaag | 1080 |
| aaccaggtgt ccctgacctg tctcgtgaaa ggcttctacc cctccgatat cgccgtggaa | 1140 |
| tgggagtcca acggccagcc tgagaacaac tacaagacca ccccctgt gctggactcc | 1200 |
| gacggctcat tcttcctgta cagcaagctg accgtggaca gtcccggtg gcagcagggc | 1260 |
| aacgtgttct cctgctccgt gatgcacgag gccctgcaca accactacac ccagaagtcc | 1320 |
| ctgtccctga gccccggcaa atga | 1344 |

<210> SEQ ID NO 105
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
cagatccagc tgcagcagtc tggacccgag gtcgtgaagc ctggcgcctc cgtgaagatc      60
tcctgcaagg cctccggcta caccttcacc cggtactaca tccactgggt catgcagcgg     120
ccaggccagg gcctggaatg gatcggccgg atctatcccg gctccggcaa caccaagtac     180
aacgagaagt tcaagggcaa ggccaccctg accgtggaca cctctgcctc caccgcctac     240
atggaactgt cctccctgac ctccgaggat accgccgtgt acttctgtgc cagaggcggc     300
aagttcgcca tggactattg gggccagggc accctcgtga ccgtgtctag cgcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggccgtcc tacagtcctc aggactctac     540
tccctcagca gcgtggtgac agtgccctcc agctctctgg gcacccagac ctacatctgc     600
aacgtgaacc acaagccctc caataccaag gtggacaagc gggtggaacc caagtcctgc     660
gacaagaccc acacctgtcc ccttgtcct gccctgaac tgctgggcgg accttccgtg     720
ttcctgttcc ccccaaagcc caaggacacc ctgatgatct cccggacccc cgaagtgacc     780
tgcgtggtgg tggatgtgtc ccacgaggac cctgaagtga agttcaattg gtacgtggac     840
ggcgtggaag tgcacaacgc caagaccaag cctagagagg aacagtacgc ctccacctac     900
cgggtggtgt ccgtgctgac agtgctgcac caggactggc tgaacggcaa agagtacaag     960
tgcgccgtgt ccaacaaggc cctgcctgcc cccatcgaaa agaccatctc caaggccaag    1020
ggccagcccc gggaacccca ggtgtacaca ctgccccta gcagggacga gctgaccaag    1080
aaccaggtgt ccctgacctg tctcgtgaaa ggcttctacc cctccgatat cgccgtggaa    1140
tgggagtcca acggccagcc tgagaacaac tacaagacca ccccccctgt gctggactcc    1200
gacggctcat tcttcctgta cagcaagctg accgtggaca gtccggtg gcagcagggc    1260 aacgtgttct cctgctccgt gatgcacgag gccctgcaca accactacac ccagaagtcc    1320
ctgtccctga gccccggcaa atga                                           1344
```

<210> SEQ ID NO 106
<211> LENGTH: 1344
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 106

```
cagatccagc tgcagcagtc tggacccgag gtcgtgaagc ctggcgcctc cgttaagatc      60
tcctgcaagg cctccggcta caccttcacc cggtactaca tccactgggt caagcagcgg     120
ccaggccaag gcctggaatg gatcggccgg atctatcccg gctccggcaa caccaagtac     180
aacgagaagt tcaagggcaa ggccaccctg accgtggaca cctctgcctc caccgcctac     240
atggaactgt cctccctgac ctccgaggat accgccgtgt acttctgtgc cagaggcggc     300
aagttcgcca tggactattg gggccagggc accctcgtga ccgtgtctag cgcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggccgtcc tacagtcctc aggactctac     540
tccctcagca gcgtggtgac agtgccctcc agctctctgg gcacccagac ctacatctgc     600
aacgtgaacc acaagccctc caataccaag gtggacaagc gggtggaacc caagtcctgc     660
```

```
gacaagaccc acacctgtcc cccttgtcct gccctgaac tgctgggcgg accttccgtg    720
ttcctgttcc ccccaaagcc caaggacacc ctgatgatct cccggacccc cgaagtgacc    780
tgcgtggtgg tggatgtgtc ccacgaggac cctgaagtga agttcaattg gtacgtggac    840
ggcgtggaag tgcacaacgc caagaccaag cctagagagg aacagtacgc ctccacctac    900
cgggtggtgt ccgtgctgac agtgctgcac caggactggc tgaacggcaa agagtacaag    960
tgcgccgtgt ccaacaaggc cctgcctgcc cccatcgaaa agaccatctc caaggccaag   1020
ggccagcccc gggaaccca ggtgtacaca ctgcccccta gcaggacga gctgaccaag   1080 aaccaggtgt ccctgacctg tctcgtgaaa ggcttctacc cctccgatat cgccgtggaa   1140
tgggagtcca acggccagcc tgagaacaac tacaagacca cccccctgt gctggactcc   1200 gacggctcat tcttcctgta cagcaagctg accgtggaca gtccggtg gcagcagggc   1260 aacgtgttct cctgctccgt gatgcacgag gccctgcaca accactacac ccagaagtcc   1320
ctgtccctga gccccggcaa atga                                          1344
```

<210> SEQ ID NO 107
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
cagatccagc tgcagcagtc tggacccgag gtcgtgaagc ctggcgcctc cgtgaagatc     60
tcctgcaagg cctccggcta caccttcacc gactactaca tccactgggt caagcagcgg    120
ccaggccagg gcctggaatg gatcggctgg atctatcccg gctccggcaa caccaagtac    180
aacgagaagt tcaagggcaa ggccaccctg accgtgaca cctctgcctc caccgcctac    240
atggaactgt cctccctgac ctccgaggat accgccgtgt acttctgtgc cagaggcggc    300
aagttcgcca tggactattg gggccagggc accctcgtga ccgtgtctag cgcttctacc    360
aagggcccct ctgtgtttcc tctggccccc tccagcaagt ccacctctgg tggaacagcc    420
gccctgggct gcctcgtgaa ggactacttt cccgagcccg tgaccgtgtc ctggaactct    480
ggcgctctga cctctggcgt gcacaccttc cctgctgtgc tgcagtctag cggcctgtac    540
tccctgtcct ccgtcgtgac agtgccctcc agctctctgg gcacccagac ctacatctgc    600
aacgtgaacc acaagccctc caataccaag gtggacaagc gggtggaacc caagtcctgc    660
gacaagaccc acacctgtcc cccttgtcct gccctgaac tgctgggcgg accttccgtg    720
ttcctgttcc ccccaaagcc caaggacacc ctgatgatct cccggacccc cgaagtgacc    780
tgcgtggtgg tggatgtgtc ccacgaggac cctgaagtga agttcaattg gtacgtggac    840
ggcgtggaag tgcacaacgc caagaccaag cctagagagg aacagtacgc ctccacctac    900
cgggtggtgt ccgtgctgac agtgctgcac caggactggc tgaacggcaa agagtacaag    960
tgcgccgtgt ccaacaaggc cctgcctgcc cccatcgaaa agaccatctc caaggccaag   1020
ggccagcccc gggaaccca ggtgtacaca ctgcccccta gcaggacga gctgaccaag   1080 aaccaggtgt ccctgacctg tctcgtgaaa ggcttctacc cctccgatat cgccgtggaa   1140
tgggagtcca acggccagcc tgagaacaac tacaagacca cccccctgt gctggactcc   1200 gacggctcat tcttcctgta cagcaagctg accgtggaca gtccggtg gcagcagggc   1260 aacgtgttct cctgctccgt gatgcacgag gccctgcaca accactacac ccagaagtcc   1320
```

```
ctgtccctga gccccggcaa atga                                           1344
```

<210> SEQ ID NO 108
<211> LENGTH: 1489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

```
gacgtcgtga tgacacagtc ccctctgtcc ctgcctgtga ccctgggaca gcctgcctcc     60
atctcctgca gatcctccca gtccctggtg cactccaacg gcaacaccta cctgtactgg    120
tatctgcaga agcccggcca gtcccccaag cccctgatct acagagtgtc caaccggttc    180
tccggcgtgc ccgacagatt ctccggctct ggctctggca ccgacttcac cctgaagatc    240
tcccgggtgg aagccgagga cgtgggcgtg tacttctgtt ttcaaggcac ccacgtgccc    300
tacaccttcg gccagggcac ccggctggaa atcaagagaa ccgtggccgc tcccteegtg    360
ttcatcttcc cacctteega cgagcagctg aagteeggea cegettetgt egtgtgcctg    420
ctgaacaact ctaccccccg cgaggccaag gtgcagtgga aggtggacaa cgccctgcag    480
tccggcaact cccaggaatc cgtgaccgag caggactcca aggacagcac ctactccctg    540
tcctccaccc tgaccctgtc caaggccgac tacgagaagc acaaggtgta cgcctgcgaa    600
gtgacccacc agggcctgtc tagccccgtg accaagtctt tcaaccgggg cgagtgcact    660
agtggcggcg gaggatctgg cggaggtgga agtgggggag gcggatctca gtgcagctg     720
gtggaaagcg gaggcggcct ggtgcagcct gggggatctc tgagactgtc ttgtgccgcc    780
agcggcttct ccctgaccga ttatggcgtg cactgggtgc acaggcccc tggcaaagga    840
ctggaatggc tgggagtgat ttggagtggc ggaggcaccg cctacaacac cgccctgatc    900
tcccggttca ccatcagccg ggacaactcc aagaacaccc tgtacctgca gatgaactcc    960
ctgcgggccg aggacaccgc tgtgtactac tgcgccagac ggggctccta ccctacaac    1020
tacttcgacg cttggggctg cggcaccctc gtgacagtgt ctagcggagg gggaggttct   1080
gggggcggag gttcaggtgg tggtggttcc gggggtggtg gctctggtgg cggtggttct   1140
ggcggtggcg gatctcaggc tgtcgtgacc caggaaccca gcctgactgt gtctcctggc   1200
ggaaccgtga ccctgacctg cggatcttct accggcgctg tgaccgccag caactacgcc   1260
aattgggtgc agcagaaacc tggacagtgc cctagaggcc tgatcggcgg ccacaacaac   1320
agacctccag gcgtgccagc ccggttctct ggatctctgc tgggcggaaa ggccgctctg   1380
acactgctgg gtgctcagcc tgaggacgag gccgagtact actgtgccct gtggtactcc   1440
gaccactggg tcatcggagg cgggaccaag ctgaccgtgc tgggatagt                1489
```

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Gly Gly Gly Gly Ser
1               5
```

```
<210> SEQ ID NO 110
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(75)
<223> OTHER INFORMATION: This sequence may encompass 1-15 "Gly Gly Gly
      Gly Ser" repeating units

<400> SEQUENCE: 110

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Ser
65                  70                  75

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 111

His His His His His His
1               5

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gly Gly Gly Gly Ser Gly Gly Gly Gly Ser Gly Gly Gly Gly Ser
1               5                   10                  15
```